(12) United States Patent
Thede et al.

(10) Patent No.: US 12,338,250 B2
(45) Date of Patent: Jun. 24, 2025

(54) METHODS OF PREPARING MACROCYCLIC INDOLES

(71) Applicants: The Broad Institute, Inc., Cambridge, MA (US); Bayer Aktiengesellschaft, Leverkusen (DE)

(72) Inventors: Kai Thede, Leverkusen (DE); Sven Wittrock, Leverkusen (DE); Anne Mengel, Leverkusen (DE); David McKinney, Cambridge, MA (US); Christopher Lemke, Cambridge, MA (US); Steven J. Ferrara, Cambridge, MA (US); Laura Furst, Cambridge, MA (US); Guo Wei, Cambridge, MA (US); Patrick R. McCarren, Cambridge, MA (US)

(73) Assignees: The Broad Institute, Inc., Cambridge, MA (US); Bayer Aktiengesellschaft, Leverkusen (DE)

( * ) Notice: Subject to any disclaimer, the term of this patent is extended or adjusted under 35 U.S.C. 154(b) by 751 days.

(21) Appl. No.: 17/612,019

(22) PCT Filed: May 15, 2020

(86) PCT No.: PCT/US2020/033067
§ 371 (c)(1),
(2) Date: Nov. 17, 2021

(87) PCT Pub. No.: WO2020/236556
PCT Pub. Date: Nov. 26, 2020

(65) Prior Publication Data
US 2022/0289762 A1 Sep. 15, 2022

Related U.S. Application Data

(60) Provisional application No. 62/849,515, filed on May 17, 2019.

(51) Int. Cl.
*C07D 498/16* (2006.01)
*C07D 403/04* (2006.01)

(52) U.S. Cl.
CPC ......... *C07D 498/16* (2013.01); *C07D 403/04* (2013.01)

(58) Field of Classification Search
CPC ............................ C07D 498/16; C07D 403/04
See application file for complete search history.

(56) References Cited

U.S. PATENT DOCUMENTS

| | | | |
|---|---|---|---|
| 10,981,932 B2 | 4/2021 | Johannes et al. |
| 11,286,263 B2 | 3/2022 | Ferrara et al. |
| 11,401,278 B2 | 8/2022 | Furst et al. |
| 11,440,923 B2 | 9/2022 | Thede et al. |
| 11,447,504 B2 | 9/2022 | Thede et al. |
| 11,478,451 B1 | 10/2022 | Thede et al. |
| 11,492,358 B1 | 11/2022 | Johannes et al. |
| 11,891,404 B2 | 2/2024 | Thede et al. |
| 12,152,041 B2 | 11/2024 | Ferrara et al. |
| 2015/0336925 A1 | 11/2015 | Lee et al. |
| 2016/0106731 A1 | 4/2016 | Lee et al. |
| 2017/0305926 A1 | 10/2017 | Hird et al. |
| 2020/0087322 A1 | 3/2020 | Johannes et al. |
| 2021/0079018 A1 | 3/2021 | Ferrara et al. |
| 2021/0253598 A1 | 8/2021 | Thede et al. |
| 2021/0269456 A1 | 9/2021 | Thede et al. |
| 2021/0277022 A1 | 9/2021 | Thede et al. |
| 2021/0292341 A1 | 9/2021 | Furst et al. |
| 2022/0281891 A1 | 9/2022 | Ferrara et al. |
| 2022/0289762 A1 | 9/2022 | Thede et al. |
| 2023/0112244 A1 | 4/2023 | Thede et al. |

FOREIGN PATENT DOCUMENTS

| | | | |
|---|---|---|---|
| WO | WO-2008/130970 A1 | 10/2008 |
| WO | WO-2008/131000 A2 | 10/2008 |
| WO | WO-2014/047427 A2 | 3/2014 |

(Continued)

OTHER PUBLICATIONS

Adams et al., "The Bcl-2 apoptotic switch in cancer development and therapy," Oncogene, 26:1324-1337 (2007).
Beroukhim et al., "The Landscape of Somatic Copy-Number Alteration Across Human Cancers," Nature, 463(7283):899-905 (2010).
Glaser et al., "Anti-apoptotic Mcl-1 is essential for the development and sustained growth of acute myeloid leukemia," Genes Dev, 26:120-125 (2012).
Hanahan et al., "Hallmarks of Cancer: The Next Generation," Cell 144(5):646-674 (2011).
International Preliminary Report on Patentability for International Application No. PCT/EP2017/000629 dated Nov. 20, 2018.
International Preliminary Report on Patentability for International Application No. PCT/EP2018/081370 dated May 19, 2020.

(Continued)

*Primary Examiner* — Jeffrey S Lundgren
*Assistant Examiner* — W. Justin Youngblood
(74) *Attorney, Agent, or Firm* — Foley Hoag LLP; David P. Halstead; David S. Surry

(57) ABSTRACT

The present invention relates to methods of preparing substituted indole derivatives of general formula (I):

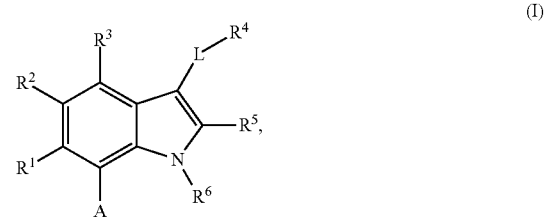

in which $R^1$, $R^2$, $R^3$, $R^4$, $R^5$, $R^6$, A and L are as defined herein, and intermediate compounds useful for preparing said compounds. These compounds are useful for manufacturing pharmaceutical compositions for the treatment or prophylaxis of diseases, in particular of hyperproliferative disorders, as a sole agent or in combination with other active ingredients.

20 Claims, No Drawings

(56) References Cited

FOREIGN PATENT DOCUMENTS

| WO | WO-2015/031608 A1 | 3/2015 |
|---|---|---|
| WO | WO-2015/148854 A1 | 10/2015 |
| WO | WO-2017/152076 A1 | 9/2017 |
| WO | WO-2017/182625 A1 | 10/2017 |
| WO | WO-2017/198341 A1 | 11/2017 |
| WO | WO-2018/098534 A1 | 6/2018 |
| WO | WO-2019/096905 A1 | 5/2019 |
| WO | WO-2019/096907 A1 | 5/2019 |
| WO | WO-2019/096909 A1 | 5/2019 |
| WO | WO-2019/096911 A1 | 5/2019 |
| WO | WO-2019/096914 A1 | 5/2019 |
| WO | WO-2019/096922 A1 | 5/2019 |
| WO | WO-2020/151738 A1 | 7/2020 |
| WO | WO-2020/236556 A1 | 11/2020 |

OTHER PUBLICATIONS

International Preliminary Report on Patentability for International Application No. PCT/EP2018/081374 dated May 19, 2020.
International Preliminary Report on Patentability for International Application No. PCT/EP2018/081378 dated May 19, 2020.
International Preliminary Report on Patentability for International Application No. PCT/EP2018/081381 dated May 19, 2020.
International Preliminary Report on Patentability for International Application No. PCT/EP2018/081388 dated May 19, 2020.
International Preliminary Report on Patentability for International Application No. PCT/EP2018/081406 dated May 19, 2020.
International Search Report and Written Opinion for International Application No. PCT/EP2017/000629 dated Sep. 6, 2019.
International Search Report and Written Opinion for International Application No. PCT/EP2018/081370 dated Feb. 13, 2019.
International Search Report and Written Opinion for International Application No. PCT/EP2018/081374 dated Feb. 13, 2019.
International Search Report and Written Opinion for International Application No. PCT/EP2018/081378 dated Jan. 9, 2019.
International Search Report and Written Opinion for International Application No. PCT/EP2018/081381 dated Jan. 15, 2019.
International Search Report and Written Opinion for International Application No. PCT/EP2018/081388 dated Feb. 14, 2019.
International Search Report and Written Opinion for International Application No. PCT/EP2018/081406 dated Feb. 11, 2019.
International Search Report and Written Opinion for International Application No. PCT/US2020/033067 mailed Jul. 19, 2020.
Korsmeyer, "BCL-2 Gene Family and the Regulation of Programmed Cell Death," Cancer Res Suppl, 59(7):1693s-1700s (1999).
Pelz et al., "Discovery of 2-Indole-acylsulfonamide Myeloid Cell Leukemia 1 (Mcl-1) Inhibitors Using Fragment-Based Methods," Journal of Medicinal Chemistry, 59(5): 2054-2066 (2016).
Wertz et al., "Sensitivity to antitubulin chemotherapeutics is regulated by MCL1 and FBW7," Nature, 471:110-114 (2011).
Zhang et al., "Research progress of GSK-3 inhibitors," Progress in Chemistry, 19(4): 614-623 (2007).
Zhou et al., "MCL1 transgenic mice exhibit a high incidence of B-cell lymphoma manifested as a spectrum of histologic subtypes," Blood, 97(12):3902-3909 (2001).
Extended European Search Report for Application No. 20808660.3 dated Apr. 24, 2023.

METHODS OF PREPARING MACROCYCLIC INDOLES

CROSS-REFERENCE TO RELATED APPLICATIONS

This application is the U.S. national phase of International Application No. PCT/US2020/033067, filed May 15, 2020, which claims the benefit of U.S. Provisional Patent Application No. 62/849,515, filed May 17, 2019, the entire contents of each of which are incorporated herein by reference.

BACKGROUND

Macrocyclic indole derivatives of general formula (I) inhibit the antiapoptotic activity of Myeloid cell leukemia-1 (MCL-1) by inhibiting its interaction with proapoptotic proteins. Apoptosis, also called programmed cell death, is a natural process which allows a damaged or unwanted cell to die in a controlled manner. Deregulation of this process leads to unrestrained cell proliferation and is thus a hallmark of cancer.

MCL-1 is the largest anti-apoptotic member of the BCl-2 family of proteins that control apoptosis. MCL-1 has been identified as an important therapeutic target in cancer. MCL-1 is highly expressed in a variety of human cancers and amplification of the MCL-1 locus is one of the most frequent somatic genetic events in human cancer, further pointing to its centrality in the pathogenesis of malignancy. Its expression has been linked to deregulated anti-apoptotic pathways in cancer, thus leading to increased cancer cell survival, tumor development and resistance to anticancer therapies. MCL-1 protein has been shown to mediate survival in models of acute myeloid leukemia, lymphomas and multiple myeloma. In malignant cells, apoptotic signaling is often deregulated, leading to uncontrolled growth and therapeutic resistance. One key resistance mechanism to apoptosis is to upregulate or genetically amplify MCL-1. As no inhibitors have shown efficacy in the clinic yet, there is still a need for further MCL-1 inhibitors to be provided.

Synthesis of MCL-1 inhibitors of formula (I) require a lengthy series of chemical reactions that can be time and cost intensive to perform. Several routes to these compounds rely on heavy metal catalysis which can have negative environmental impact. Thus, a need exists for more efficient and clean preparations of compounds of formula (I).

SUMMARY

The present disclosure relates in part to the synthesis of compounds of formula (I) using a concise and convergent macrocyclic ring closing strategy, providing late stage intermediates for the completion of formula (I) compound preparation.

Accordingly, in some embodiments, the present disclosure provides a method for preparing a compound of Formula (I):

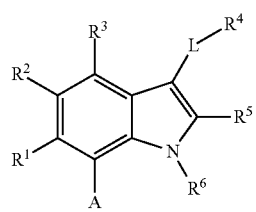

(I)

wherein
A is

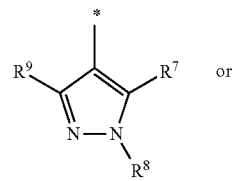

(A1)

or

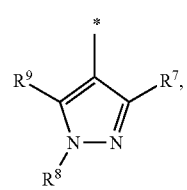

(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a ($C_1$-$C_3$-alkyl)-S(O)— group, a ($C_1$-$C_3$-alkyl)-S(O)$_2$— group, a $C_1$-$C_3$-haloalkoxy group, a $C_1$-$C_3$-haloalkylthio group and a $C_3$-$C_8$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_8$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$;

m is 2, 3, or 4;

$R^5$ is selected from a COOH group, a COO($C_1$-$C_6$-alkyl) group, a group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

—$R^6$-$R^7$— is $^{\#}$—(CH$_2$)$_n$—(B)$_t$—CR$^{22}$R$^{23}$—$^{\#\#}$,
wherein # is the point of attachment with the indole nitrogen atom and ## is the point of attachment with the pyrazole carbon atom bearing the $R^7$ substituent; and wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

n is 2, 3, 4, 5, or 6;
t is 1;
where the integers selected for variables n and t, together with the methylene group CR$^{22}$R$^{23}$ and the other non-variable atoms of the pyrazole and the indole moiety result in forming a 9-membered to 13-membered ring independently from the selection of variable A1 or A2;
B is —O—;
$R^8$ is selected from a hydrogen atom,
- a $C_1$-$C_6$-alkyl group, which is unsubstituted or substituted with one or more substituents independently selected from.
  - a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a NR$^{20}$R$^{21}$ group;
- a $C_1$-$C_3$-haloalkyl group,
- a $C_3$-$C_6$-cycloalkyl group and
- a $C_1$-$C_6$-alkyl group in which one or two not directly adjacent carbon atoms are independently replaced by a heteroatom selected from —O— and —NH—;

$R^9$ is selected from a hydrogen atom,
- a $C_1$-$C_4$-alkyl group,
- a $C_1$-$C_3$-hydroxyalkyl group,
- a $C_1$-$C_4$-haloalkyl group,
- a $C_1$-$C_4$-haloalkyl-NH—C(O)—O—($C_1$-$C_3$-alkylene)- group,
- a $C_2$-$C_6$-haloalkenyl group,
- a $C_1$-$C_6$-alkyl-O— group,
- a $C_1$-$C_4$-haloalkoxy group,
- a $C_1$-$C_6$-alkyl-O—($C_1$-$C_3$-alkylene)- group,
- a ($C_3$-$C_7$)-cycloalkyl group,
- a ($C_3$-$C_7$)-cycloalkyl-O—($C_1$-$C_3$-alkylene)- group,
- a phenyl-O—($C_1$-$C_3$-alkylene)- group,
- a phenyl-($C_1$-$C_3$-alkylene)-O—($C_1$-$C_3$-alkylene)- group,
- a $R^{18}$-(phenylene)-($C_1$-$C_3$-alkylene)-O—($C_1$-$C_3$-alkylene)- group,
- a $R^{18}$-(phenylene)-O—($C_1$-$C_3$-alkylene)- group,
- a $R^{18}$-(phenylene)-(heteroarylene)-O—($C_1$-$C_3$-alkylene)- group,
- a ($R^{18}$)-(heterocycloalkylene)-($C_1$-$C_3$-alkylene)- group,
- a ($R^{18}$)-(heterocycloalkylene)-(phenylene)-O—($C_1$-$C_3$-alkylene)- group,
- a (heterocycloalkenyl)-(phenylene)-O—($C_1$-$C_3$-alkylene)- group,
- a ($R^{18}$)-(heteroarylene)-($C_1$-$C_3$-alkylene)-O—($C_1$-$C_3$-alkylene)- group,
- a ($R^{18}$)-(heteroarylene)-(phenylene)-O—($C_1$-$C_3$-alkylene)- group,
- a ($R^{19}$)—S(O)$_2$-(phenylene)-O—($C_1$-$C_3$-alkylene)- group,
- a ($R^{19}$)—S(O)$_2$—NH-(phenylene)-O—($C_1$-$C_3$-alkylene)- group,
- a ($R^{19}$)—S(O)$_2$—NH-(phenylene)-O—($C_1$-$C_3$-alkylene)- group,
- a ($R^{19}$)—S(O)$_2$—N($C_1$-$C_6$-alkyl)-(phenylene)-O—($C_1$-$C_3$-alkylene)- group,
- a ($R^{19}$)—S(O)$_2$-(heterocycloalkylene)-(phenylene)-O—($C_1$-$C_3$-alkylene)- group,
- a ($R^{18}$)-(heterocycloalkylene)-(heteroarylene)-O—($C_1$-$C_3$-alkylene)- group,
- a ($R^{19}$)-(heteroarylene)-O—($C_1$-$C_3$-alkylene)- group,
- a ($R^{18}$)-(heteroarylene)-O—($C_1$-$C_3$-alkylene)- group,
- a ($R^{19}$)—S(O)$_2$-(heteroarylene)-O—($C_1$-$C_3$-alkylene)- group,
- a ($R^{19}$)—S(O)$_2$-(heterocycloalkylene)-(heteroarylene)-O—($C_1$-$C_3$-alkylene)- group,
- a NR$^{20}$R$^{21}$—($C_1$-$C_3$-alkylene)- group,
- a ($C_1$-$C_3$-alkyl)-NH—($C_1$-$C_3$-alkylene)- group,
- a ($C_1$-$C_3$-haloalkyl)-($C_1$-$C_3$-alkylene)-NH—($C_1$-$C_3$-alkylene)- group,
- a ($C_1$-$C_3$-haloalkyl)-NH—($C_1$-$C_3$-alkylene)- group,
- a ($C_1$-$C_3$-alkyl)-NH—C(O)—($C_1$-$C_3$-alkylene)- group,
- a ($C_1$-$C_3$-alkyl)-NR$^{15}$—C(O)—($C_1$-$C_3$-alkylene)- group,
- a ($C_1$-$C_3$-alkyl)-C(O)—NH—($C_1$-$C_3$-alkylene)- group,
- a ($C_1$-$C_3$-alkyl)-C(O)—NR$^{15}$—($C_1$-$C_3$-alkylene)- group,
- a group and a group,
where the phenyl ring is unsubstituted or substituted with a halogen atom, a hydroxy group or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxy group, a $C_1$-$C_3$-alkyl group and a $C_1$-$C_3$-alkoxy group,
or $R^8$ and $R^9$ together form a 5-membered or 6-membered ring optionally comprising one or two heteroatoms independently selected from —O— and —NR$^{14}$—;

$R^{14}$ is a hydrogen atom or a $C_1$-$C_3$-alkyl group;

$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_8$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}OC(O)$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a NR$^{20}$R$^{21}$ group; $R^{20}$ and $R^{21}$ are each independently selected from a hydrogen atom and a $C_1$-$C_6$-alkyl group;

$R^{22}$ is independently selected from,
a halogen atom,
a $C_1$-$C_6$-alkyl group
  which is unsubstituted or substituted with one or more substituents selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group;
a $C_1$-$C_3$-alkyl-C(O)— group,
a $C_3$-$C_6$-cycloalkyl group,
an aryl group,
a heterocycloalkyl group and
a heteroaryl group;
  whereby any heterocycloalkyl group of $R^{22}$ may optionally be itself further substituted with a $C_1$-$C_3$-alkyl group or one or two halogen atoms;

$R^{23}$ is a hydrogen atom;

comprising contacting a compound of formula (IIA) when A is A1, or formula (IIB) when A is A2:

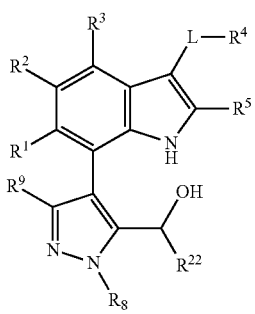

(IIA)

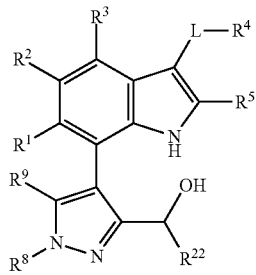

(IIB)

with a di-functionalized alkane

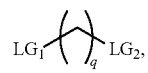

wherein
variables $R^1$, $R^2$, $R^3$, $R^4$, $R^8$, $R^9$, and $R^{22}$ are as defined above,
$R^5$ is selected from a COO($C_1$-$C_6$-alkyl) group, a

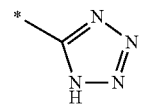

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

q is 2, 3, 4, 5, or 6, and

LG$^1$ and LG$^2$ are each independently halo or sulfonate.

DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, preferably 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, preferably with one, two or three substituents.

The terms "oxo", "an oxo group" or "an oxo substituent" mean a doubly attached oxygen atom =O. Oxo may be attached to atoms of suitable valency, for example to a saturated carbon atom or to a sulfur atom. For example, but without limitation, one oxo group can be attached to a carbon atom, resulting in the formation of a carbonyl group C(=O), or two oxo groups can be attached to one sulfur atom, resulting in the formation of a sulfonyl group —S(=O)$_2$.

The term "ring substituent" means a substituent attached to an aromatic or nonaromatic ring which replaces an available hydrogen atom on the ring.

Should a composite substituent be composed of more than one part, e.g., ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of."

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings:

The term "halogen atom" means a fluorine, chlorine, bromine or iodine atom, preferably a fluorine, chlorine or bromine atom.

The term "$C_1$-$C_8$-alkyl-" means a linear or branched, saturated hydrocarbon group having 1, 2, 3, 4, 5, 6, 7 or 8 carbon atoms, e.g., a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-, n-heptyl-, 5-methylhexyl-, 4-methylhexyl-, 2-methylhexyl-, 1-methylhexyl-, 2-ethylpentyl-, 1-ethylpentyl-, 3,3-dimethylpentyl-, 2,2-dimethylpentyl-, 1,1-dimethylpentyl-, 2,3-dimethylpentyl-, 1,3-dimethylpentyl-, 1,2-dimethylpentyl-, n-octyl-, 6-methylheptyl-, 4-methylheptyl-, 2-methylheptyl-, 1-methylheptyl-, 2-ethylhexyl-, 1-ethylhexyl-, 3,3-dimethylhexyl-, 2,2-dimethylhexyl-, 1,1-dimethylhexyl-, 2,3-dimethylhexyl-, 1,3-dimethylhexyl-, 1,2-dimethylhexyl-group, or an isomer thereof. Preferably, said group has 1, 2, 3, 4, 5 or 6 carbon atoms ("$C_1$-$C_6$-alkyl-"), e.g., a methyl-, ethyl-, n-propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl- or 1,2-dimethylbutyl group, or an isomer thereof. More preferably, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or tert-butyl- group, 1, 2 or 3 carbon atoms ("$C_1$-$C_3$-alkyl-"), e.g., a methyl-, ethyl-, n-propyl- or iso-propyl group, or 1 or 2 carbon atoms ("$C_1$-$C_2$-alkyl-"), e.g., a methyl group, an ethyl group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_2$-$C_6$-alkylene" means a linear or branched, saturated, divalent hydrocarbon chain (or "tether") having 2, 3, 4, 5 or 6 carbon atoms, e.g., —CH$_2$—CH$_2$— ("ethylene" or "$C_2$-alkylene"), —CH$_2$—CH$_2$—CH$_2$—, —C(H)(CH$_3$)—CH$_2$— or —C(CH$_3$)$_2$— ("propylene" or "$C_3$-alkylene"), or, for example —CH$_2$—C(H)(CH$_3$)—CH$_2$—, —CH$_2$—C(CH$_3$)$_2$—, —CH$_2$—CH$_2$—CH$_2$—CH$_2$— ("butylene" or "$C_4$-alkylene"), "$C_5$-alkylene", e.g., —CH$_2$—CH$_2$—CH$_2$—CH$_2$—CH$_2$— ("n-pentylene"), or "—$C_6$-alkylene-", e.g., —CH$_2$—CH$_2$—CH$_2$—CH$_2$—CH$_2$—CH$_2$— ("n-hexylene") or a —C(CH$_3$)$_2$—C(CH$_3$)$_2$ group.

The term "hydroxy-($C_1$-$C_6$-alkyl)-" means a linear or branched, saturated, hydrocarbon group in which one or more hydrogen atoms of a "$C_1$-$C_6$-alkyl-" as defined supra are each replaced by a hydroxy group, e.g., a hydroxymethyl-, 1-hydroxyethyl-, 2-hydroxyethyl-, 1,2-dihydroxyethyl-, 3-hydroxypropyl-, 2-hydroxypropyl-, 2,3-dihydroxypropyl-, 1,3-dihydroxypropan-2-yl-, 3-hydroxy-2-methylpropyl-, 2-hydroxy-2-methyl-propyl-, or a 1-hydroxy-2-methyl-propyl- group. In certain preferred embodiments, the hydroxyalkyl group means a linear or branched, saturated, monovalent hydrocarbon group has 1, 2 or 3 carbon atoms in which 1 hydrogen atom is replaced with a hydroxy group e.g. a hydroxymethyl-, 1-hydroxyethyl-, 2-hydroxyethyl-, 3-hydroxypropyl-, 2-hydroxypropyl-, 1-hydroxypropyl-, 2-hydroxy-2-methyl-ethyl group.

The term "$C_1$-$C_6$-haloalkyl" means a linear or branched, saturated, monovalent hydrocarbon group in which the term "$C_1$-$C_6$-alkyl" is as defined supra and in which one or more of the hydrogen atoms are replaced, identically or differently, with a halogen atom. Preferably, said halogen atom is a fluorine atom. Said $C_1$-$C_6$-haloalkyl, preferably a $C_1$-$C_3$-haloalkyl group is, for example, fluoromethyl-, difluoromethyl-, trifluoromethyl-, 2-fluoroethyl-, 2,2-difluoroethyl-, 2,2,2-trifluoroethyl-, pentafluoroethyl-, 3,3,3-trifluoropropyl- or a 1,3-difluoropropan-2-yl group.

The term "$C_1$-$C_6$-alkoxy" means a linear or branched, saturated, monovalent group of formula ($C_1$-$C_6$-alkyl)-O—, in which the term "$C_1$-$C_6$-alkyl" group is as defined supra, e.g. methoxy-, ethoxy-, n-propoxy-, isopropoxy-, n-butoxy-, sec-butoxy-, isobutoxy-, tert-butoxy-, pentyloxy-, isopentyloxy- or a n-hexyloxy group, or an isomer thereof.

The term "$C_1$-$C_6$-alkylthio" or "$C_1$-$C_6$-thioalkyl" means a linear or branched, saturated, monovalent group of formula ($C_1$-$C_6$-alkyl)-S—, in which the term "$C_1$-$C_6$-alkyl" is as defined supra, e.g. methylthio-, ethylthio-, n-propylthio-, isopropylthio-, n-butylthio-, sec-butylthio-, isobutylthio-, tert-butylthio-, pentylthio-, isopentylthio- or a n-hexylthio group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Preferably, said halogen atom in "$C_1$-$C_6$-haloalkoxy-" is fluorine, resulting in a group referred to herein as "$C_1$-$C_6$-fluoroalkoxy-". Representative $C_1$-$C_6$-fluoroalkoxy groups include, for example, —$OCF_3$, —$OCHF_2$, —$OCH_2F$, —$OCF_2CF_3$ and —$OCH_2CF_3$.

The term "$C_1$-$C_6$-haloalkylthio" or "$C_1$-$C_6$-halothioalkyl" or "$C_1$-$C_6$-haloalkyl-S—" means a linear or branched, saturated, monovalent $C_1$-$C_6$-alkylthio group, as defined supra, in which one or more of the hydrogen atoms is replaced, identically or differently, with a halogen atom. Preferably, said halogen atom in "$C_1$-$C_6$-haloalkylthio-" is fluorine.

The term "$C_2$-$C_6$-alkenyl-" means a linear or branched, monovalent hydrocarbon group, which contains one or more double bonds and which has 2, 3, 4, 5 or 6 carbon atoms, preferably 2, 3 or 4 carbon atoms ("$C_2$-$C_4$-alkenyl-") or 2 or 3 carbon atoms ("$C_2$-$C_3$-alkenyl-"), it being understood that in the case in which said alkenyl- group contains more than one double bond, then said double bonds may be isolated from, or conjugated with, each other. Representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (Z)-2-methylpent-3-enyl-, (E)-2-methylpent-3-enyl-, (E)-1-methylpent-3-enyl-, (E)-4-methylpent-2-enyl-, (Z)-1-methylpent-3-enyl-, (Z)-4-methylpent-2-enyl-, (Z)-3-methylpent-2-enyl-, (E)-3-methylpent-2-enyl-, (E)-2-methylpent-2-enyl-, (E)-1-methylpent-2-enyl-, (Z)-2-methylpent-2-enyl-, (Z)-1-methylpent-2-enyl-, (Z)-4-methylpent-1-enyl-, (E)-4-methylpent-1-enyl-, (E)-3-methylpent-1-enyl-, (E)-2-methylpent-1-enyl-, (Z)-3-methylpent-1-enyl-, (Z)-2-methylpent-1-enyl-, (Z)-1-methylpent-1-enyl-, (E)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and a 1-(1,1-dimethylethyl-) ethenyl group. Preferably, said group is a ethenyl- or prop-2-enyl group.

The same definitions can be applied should the alkenyl group be placed within a chain as a bivalent "$C_1$-$C_6$-alkenylene" moiety. All names as mentioned above then will bear a "ene" added to their end, thus e.g., a "pentenyl" becomes a bivalent "pentenylene" group.

The term "$C_2$-$C_6$-haloalkenyl-" means a linear or branched hydrocarbon group in which one or more of the hydrogen atoms of a "$C_2$-$C_6$-alkenyl-" as defined supra are each replaced, identically or differently, by a halogen atom. Preferably, said halogen atom is fluorine, resulting in a group referred herein as "$C_2$-$C_6$-fluoroalkenyl-". Representative $C_2$-$C_6$-fluoroalkenyl- groups include, for example, —$CH=CF_2$, —$CF=CH_2$, —$CF=CF_2$, —$C(CH_3)=CF_2$, —$CH=C(F)$—$CH_3$, —$CH_2$—$CF=CF_2$ and —$CF_2$—$CH=CH_2$.

The term "$C_2$-$C_6$-alkynyl-" means a linear or branched, monovalent hydrocarbon group which contains one or more triple bonds and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl- groups include, for example, an ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and 3,3-dimethylbut-1-ynyl- group. Preferably, said alkynyl- group is ethynyl-, prop-1-ynyl- or prop-2-ynyl group.

The term "$C_3$-$C_{10}$-cycloalkyl-" means a saturated monocyclic or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl- group may be, for example, a monocyclic hydrocarbon ring, e.g., cyclopropyl-, cyclobutyl-, cyclopentyl-, cyclohexyl- or cycloheptyl-, or a bicyclic hydrocarbon ring, such as decalinyl-. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl- group, or said hydrocarbon ring is monocyclic and contains 3, 4, 5 or 6 carbon atoms ("$C_3$-$C_6$-cycloalkyl-"), e.g., a cyclopropyl-, cyclobutyl-, cyclopentyl- or cyclohexyl group. A cycloalkyl group may be optionally substituted as defined at the respective part wherein such term is used.

The term "$C_4$-$C_8$-cycloalkenyl" means a monovalent, mono- or bicyclic hydrocarbon ring which contains 4, 5, 6, 7 or 8 carbon atoms and one double bond. Preferably, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., cyclobutenyl-, cyclopentenyl-, cyclohexenyl-, cycloheptenyl- or a cyclooctenyl group, or a bicyclic hydrocarbon ring, e.g., a bicyclo[2.2.1]hept-2-enyl- or a bicyclo[2.2.2]oct-2-enyl group.

The term "4- to 10-membered heterocycloalkyl-" means a saturated mono- or bicyclic hydrocarbon ring which contains 3, 4, 5, 6, 7, 8 or 9 carbon atoms and which contains 1, 2, 3 or 4 heteroatoms which may be identical or different, said heteroatoms preferably selected from oxygen, nitrogen or sulfur and wherein carbon atoms and heteroatoms add up to 4, 5, 6, 7, 8, 9 or 10 ring atoms in total, it being possible for said heterocycloalkyl- group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, said "4- to 10-membered heterocycloalkyl-" group is monocyclic and contains 3, 4, 5 or 6 carbon atoms and one or two of the above-mentioned heteroatoms, adding up to 4, 5, 6 or 7 ring atoms in total (a "4- to 7-membered monocyclic heterocycloalkyl-"), or contains 3, 4 or 5 carbon atoms and one or two of the above-mentioned heteroatoms, adding up to 4, 5 or 6 ring atoms in total (a "4- to 6-membered monocyclic heterocycloalkyl-"), or contains 3, 4 or 5 carbon atoms and one or two of the above-mentioned heteroatoms, adding up to 5 or 6 ring atoms in total (a "5- to 6-membered monocyclic heterocycloalkyl-"); it being possible for said heterocycloalkyl- group to be attached to the rest of the molecule via any one of the carbon atoms or the nitrogen atoms, if present.

Exemplarily, without being limited thereto, said "4- to 7-membered monocyclic heterocycloalkyl-", can be a 4-membered ring, a "4-membered heterocycloalkyl-" group, such as azetidinyl- or an oxetanyl group; or a 5-membered ring, a "5-membered heterocycloalkyl-" group, such as a tetrahydrofuranyl-, dioxolinyl-, pyrrolidinyl-, imidazolidinyl-, pyrazolidinyl- or a pyrrolinyl group; or a 6-membered ring, a "6-membered heterocycloalkyl-" group, such as a tetrahydropyranyl-, piperidinyl-, morpholinyl-, 3-oxomorpholin-4-yl, dithianyl-, thiomorpholinyl- or a piperazinyl group; or a 7-membered ring, a "7-membered heterocycloalkyl-" group, such as an azepanyl-, diazepanyl- or an oxazepanyl group, for example. The heterocycloalkyl groups may be one or more times substituted with $C_1$-$C_3$-alkyl, $C_1$-$C_3$-alkoxy, hydroxy, halogen or a carbonyl group.

The term "5- to 7-membered heterocycloalkenyl" means a monocyclic, unsaturated, non-aromatic heterocycle with 5, 6, or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, a 4H-pyranyl-, 3,6-dihydro-2H-pyran-4-yl-, 2H-pyranyl-, dihydropyridinyl-, tetrahydropyridinyl-, 2-oxopyridin-1 (2H)-yl-, 2,5-dihydro-1H-pyrrolyl-, [1,3]dioxolyl-, 4H-[1,3,4]thiadiazinyl-, 2,5-dihydrofuranyl-, 2,3-dihydrofuranyl-, 2,5-dihydrothiophenyl-, 2,3-dihydrothiophenyl-, 4,5-dihydrooxazolyl- or a 4H-[1,4]thiazinyl- group. Those heterocycloalkenyl groups may be substituted with a hydroxy group or a methoxy group.

The term "fused heterocycloalkyl" or "heterobicycloalkyl-" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom. Said fused heterocycloalkyl or "heterobicycloalkyl-" group may be, for example, an azabicyclo[3.3.0]octyl-, azabicyclo[4.3.0]nonyl-, diazabicyclo[4.3.0]nonyl-, oxazabicyclo[4.3.0]nonyl-, thiazabicyclo[4.3.0]nonyl- or a azabicyclo[4.4.0]decyl group.

The term "aryl" means a phenyl-, naphthyl-, 5,6-dihydronaphthyl-, 7,8-dihydronaphthyl-, 5,6,7,8-tetrahydronaphthyl-, an indanyl-, or an indenyl group, which is unsubstituted or substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, preferably halogen, $C_1$-$C_3$-alkyl, $C_1$-$C_3$-haloalkyl, $C_1$-$C_3$-alkoxy, and $C_1$-$C_3$-haloalkoxy.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms and which contains 1, 2, 3 or 4 heteroatoms which may be identical or different, said heteroatoms being selected from oxygen, nitrogen and sulfur. Said heteroaryl- group can be a 5-membered heteroaryl group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or a tetrazolyl group; or a 6-membered heteroaryl group, such as, for example, a pyridyl-, pyridazinyl-, pyrimidyl-, pyrazinyl- or a triazinyl group; or a benzo-fused 5-membered heteroaryl- group, such as, for example, a benzofuranyl-, benzothienyl-, benzoxazolyl-, benzisoxazolyl-, benzimidazolyl-, benzothiazolyl-, benzotriazolyl-, indazolyl-, indolyl- or a isoindolyl group; or a benzo-fused 6-membered heteroaryl group, such as, for example, a quinolinyl-, quinazolinyl-, isoquinolinyl-, cinnolinyl-, phthalazinyl- or quinoxalinyl-; or another bicyclic group, such as, for example, indolizinyl-, purinyl- or a pteridinyl group; or a tricyclic heteroaryl- group, such as, for example, a carbazolyl-, acridinyl- or a phenazinyl group Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur ("5- to 6-membered monocyclic heteroaryl-"), such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or a triazinyl group.

In general and unless otherwise mentioned, said heteroaryl- groups include all the possible isomeric forms thereof, e.g., the positional isomers thereof. Thus, for some illustrative non-restricting examples, the term pyridyl-includes pyridin-2-yl-, pyridin-3-yl- and pyridin-4-yl-; the term thienyl-includes thien-2-yl- and thien-3-yl-. Furthermore, said heteroaryl- groups can be attached to the rest of the molecule via any one of the carbon atoms, or, if applicable, a nitrogen atom, e.g., pyrrol-1-yl-, pyrazol-1-yl- or imidazol-1-yl-.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl-includes pyridin-2-yl-, pyridin-3-yl- and pyridin-4-yl-; or the term thienyl-includes thien-2-yl- and thien-3-yl-.

Preferably, the heteroaryl group is a pyridyl group or pyrimidyl group or an imidazolyl group, including a hydroxy substitution of the pyridyl group leading e.g. to a 2-hydroxy-pyridyl group which is the tautomeric form to a 2-oxo-2 (1H)-pyridyl group.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$; in the case of "$C_1$-$C_6$-haloalkyl-" or "$C_1$-$C_6$-haloalkoxy-" even more preferably $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_4$, $C_2$-$C_5$; preferably $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl- group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

As used herein, the term "formula (II)" refers to either or both of compounds of formulas (IIA) and (IIB):

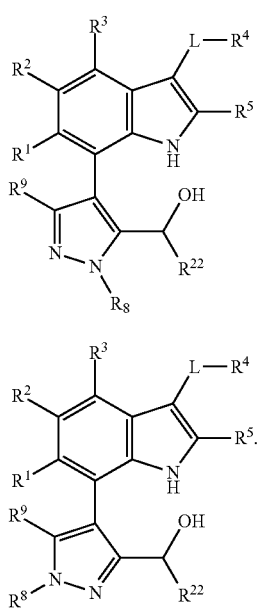

As used herein, the term "leaving group" refers to an atom or a group of atoms that is displaced in a chemical reaction as stable species taking with it the bonding electrons, e.g., typically forming an anion. Preferably, a leaving group is selected from: halo, preferably a chloro, bromo iodo, or (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl)sulfonyl]oxy-, [(4-isopropylphenyl)sulfonyl]oxy-, [(2,4,6-triisopropylphenyl)sulfonyl]oxy-, [(2,4,6-trimethylphenyl)sulfonyl]oxy-, [(4-tert-butylphenyl)sulfonyl]oxy-, (phenylsulfonyl)oxy- and a [(4-methoxyphenyl)sulfonyl]oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are descibed for example in T. W. Greene and P. G. M. Wuts in *Protective Groups in Organic Synthesis*, 4$^{th}$ edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc. and to give compounds which are not inherently unstable. For example, any carbon atom will be bonded to two, three, or four other atoms, consistent with the four valence electrons of carbon.

It is possible for the compounds of general formula (I) to exist as isotopic variants. The invention therefore includes one or more isotopic variant(s) of the compounds of general formula (I), particularly deuterium-containing compounds of general formula (I). The invention also includes all suitable isotopic variations of a compound of the invention. The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70 (1), 217-235, 1998.

An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}$H (deuterium), $^{3}$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Accordingly, recitation of "hydrogen" or "H" should be understood to encompass $^{1}$H (protium), $^{2}$H (deuterium) and $^{3}$H (tritium) unless otherwise specified. Certain isotopic variations of a compound of the invention, for example, those in which one or more radioactive isotopes such as $^{3}$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}$H or $^{14}$C, are incorporated are useful, e.g., in drug and/or substrate tissue distribution studies. These isotopes are particularly preferred for the ease of their incorporation and detectability. Positron-emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Preferably, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19 (3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Preferably, the deuterium atom(s) of deuterium-containing compound(s) of general formula (I) is/are attached to a carbon atom and/or is/are located at those positions of the compound of general formula. (I), which are sites of attack for metabolizing enzymes such as e.g., cytochrome P$_{450}$.

For example, in some embodiments, the present invention concerns a deuterium-containing compound of general formula (I), e.g.:

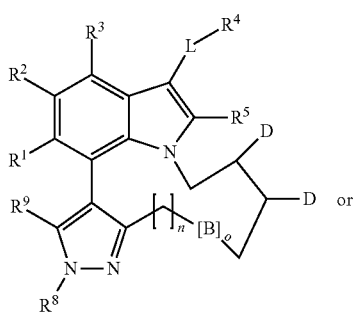

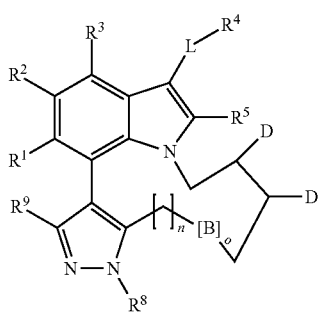

Such deuterium-containing compounds can be prepared by methods well-known to the person skilled in the art. Preferably, such deuterium-containing compounds can be prepared from the corresponding olefins, which are available by methods known to the person skilled in the art, such as ring closing metathesis reactions, as discussed e.g., in the general description of the synthesis of compounds of general formula (I), infra, in the context of Schemes 2c and 2j, respectively.

Where the plural form of the word compounds, salts, polymorphs, hydrates, solvates and the like, is used herein, this is taken to mean also a single compound, salt, polymorph, isomer, hydrate, solvate or the like. The terms "a" or "an," as used in herein means one or more.

By "stable compound' or "stable structure" is meant a compound that is sufficiently robust to survive isolation to a useful degree of purity from a reaction mixture and formulation into an efficacious therapeutic agent.

Compounds of the present invention are typically chiral merely as a result of restricted rotation around at least one single bond, which is due to limited conformational flexibility of their macrocyclic core as a whole or even of open chain precursors. Hence, compounds of the present invention as well as the corresponding macrocyclic intermediates can exist as atropisomers. Atropisomers represent a subclass of conformers which arise from restricted rotation around a single bond. The conformers (called atropisomers) can be isolated as separated species (IUPAC Gold book, http://goldbook.iupac.org/A00511.html; Pure and Appl. Chem., 2009, 68, 2193-2222). This induced chirality belongs to the axial type of chirality. The compounds of the present invention furthermore optionally contain one or more asymmetric centers, depending upon the location and nature of the various substituents desired. It is possible that one or more asymmetric carbon atoms are present in the (R) or(S) configuration, which can result in racemic mixtures in the case of a single asymmetric center, and in diastereomeric mixtures in the case of multiple asymmetric centers. Hence, compounds of the present invention featuring the above-mentioned atropisomerism and an additional asymmetric centre can also exist as diasteromeric mixtures as described supra.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one isomer (enantiomer) displays the desired biological activity and the second isomer (enantiomer) is inactive, the preferred isomer is the one which produces the more desirable biological activity. Should one isomer (enantiomer/diastereomer) display better activity than the other isomer (enantiomer/diastreromer) the preferred isomer is the one which produces the better biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

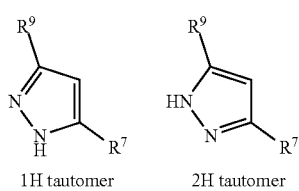

1H tautomer    2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

Certain embodiments of the invention include the compounds of formula (I) and a tautomer, an N-oxide, or a salt thereof, or a salt of a tautomer, or a salt of an N-oxide, or a mixture of same. Some embodiments of the invention include the compounds of formula (I) and a tautomer, or a salt thereof, or a salt of a tautomer, or a mixture of same. Certain embodiments of the invention provide the compounds of formula (I) and salts thereof, more specifically an amine salt, or an organic acid salt, more preferably a diethylamine salt, an acetic acid salt or a citric acid salt.

The present invention also includes useful forms of the compounds of the present invention, such as metabolites, hydrates, solvates, prodrugs and salts, in particular pharmaceutically acceptable salts and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemihydrate, (semihydrate), monohydrate, sesquihydrate, dihydrate, trihydrate, tetrahydrate, pentahydrate etc, solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, preferably any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19. It includes any physiologically acceptable salt as referred to below.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, and nitric acid or with an organic acid, such as formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)-benzoic acid, camphoric acid, cinnamic acid, cyclopentanepropionic acid, digluconic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonate acid, itaconic acid, sulfamic acid, trifluoromethanesulfonic acid, dodecylsulfuric acid, ethansulfonic acid, benzenesulfonic acid, para-toluenesulfonic acid, methansulfonic acid, 2-naphthalenesulfonic acid, naphthalenedisulfonic acid, camphorsulfonic acid acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, hemisulfuric acid and thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base and 1-amino-2,3,4-butanetriol.

Additionally, the compounds according to the invention may form salts with a quaternary ammonium ion obtainable, e.g., by quaternisation of a basic nitrogen-containing group with agents such as lower alkylhalides, such as alkylchlorides, e.g. methylchloride, ethylchloride, propylchloride and butylchloride; such as alkylbromides, e.g. methylbromide, ethylbromide, propylbromide and butylbromide; and such as alkyliodides; e.g. methyliodide, ethyliodide, propyliodide and butyliodide; dialkylsulfates such as dimethylsulfate, diethylsulfate, dibutylsulfate and diamylsulfates, long chain halides such as e.g. decylchloride, laurylchloride, myristylchloride and stearylchloride, decylbromide, laurylbromide, myristylbromide and stearylbromide, decyliodide, laurylioiodide, myristyliodide and stearyliodide, aralkylhalides such as benzylchloride, benzylbromide, benzyliodide and phenethylbromides and others. Examples of suitable quaternary ammonium ions are tetramethylammonium, tetraethylammonium, tetra(n-propyl) ammonium, tetra(n-butyl) ammonium, or N-benzyl-N,N,N-trimethylammonium.

The present invention includes all possible salts of the compounds of the present invention as single salts, or as any mixture of said salts, in any ratio.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

Methods of Preparation

In some embodiments, the present disclosure provides a method for preparing a compound of Formula (I):

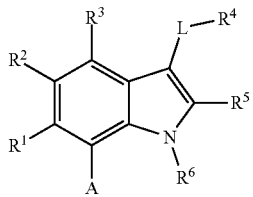

(I)

wherein
A is

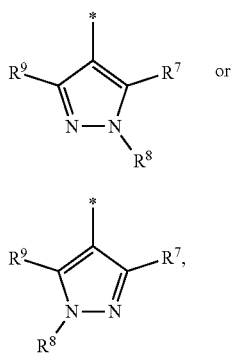

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a ($C_1$-$C_3$-alkyl)-S(O)— group, a ($C_1$-$C_3$-alkyl)-S(O)$_2$— group, a $C_1$-$C_3$-haloalkoxy group, a $C_1$-$C_3$-haloalkylthio group and a $C_3$-$C_8$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$;

m is 2, 3, or 4;

$R^5$ is selected from a COOH group, a COO($C_1$-$C_6$-alkyl) group, a

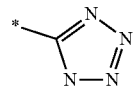

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

—$R^6$-$R^7$— is $^{\#}$—(CH$_2$)$_n$—(B)$_t$—CR$^{22}$R$^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —CH$_2$— groups may be unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

n is 2, 3, 4, 5, or 6;

t is 1;

where the integers selected for variables n and t, together with the methylene group CR$^{22}$R$^{23}$ and the other non-variable atoms of the pyrazole and the indole moiety result in forming a 9-membered to 13-membered ring independently from the selection of variable A1 or A2;

B is —O—;

$R^8$ is selected from a hydrogen atom,
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a NR$^{20}$R$^{21}$ group;
a $C_1$-$C_3$-haloalkyl group,
a $C_3$-$C_6$-cycloalkyl group and
a $C_1$-$C_6$-alkyl group in which one or two not directly adjacent carbon atoms are independently replaced by a heteroatom selected from —O— and —NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group, a $(C_3-C_7)$-cycloalkyl group,
a $(C_3-C_7)$-cycloalkyl-O—$(C_1-C_3$-alkylene)- group,
a phenyl-O—$(C_1-C_3$-alkylene)- group,
a phenyl-$(C_1-C_3$-alkylene)-O—$(C_1-C_3$-alkylene)- group,
a $R^{18}$-(phenylene)-$(C_1-C_3$-alkylene)-O—$(C_1-C_3$-alkylene)- group,
a $R^{18}$-(phenylene)-O—$(C_1-C_3$-alkylene)- group,
a $R^{18}$-(phenylene)-(heteroarylene)-O—$(C_1-C_3$-alkylene)- group,
a $(R^{18})$-(heterocycloalkylene)-$(C_1-C_3$-alkylene)- group,
a $(R^{18})$-(heterocycloalkylene)-(phenylene)-O—$(C_1-C_3$-alkylene)- group,
a (heterocycloalkenyl)-(phenylene)-O—$(C_1-C_3$-alkylene)- group,
a $(R^{18})$-(heteroarylene)-$(C_1-C_3$-alkylene)-O—$(C_1-C_3$-alkylene)- group,
a $(R^{18})$-(heteroarylene)-(phenylene)-O—$(C_1-C_3$-alkylene)- group,
a $(R^{19})$—S(O)$_2$-(phenylene)-O—$(C_1-C_3$-alkylene)- group,
a $(R^{19})$—S(O)$_2$—NH-(phenylene)-O—$(C_1-C_3$-alkylene)- group,
a $(R^{19})$—S(O)$_2$—NH-(phenylene)-O—$(C_1-C_3$-alkylene)- group,
a $(R^{19})$—S(O)$_2$—N($C_1-C_6$-alkyl)-(phenylene)-O—$(C_1-C_3$-alkylene)- group,
a $(R^{19})$—S(O)$_2$-(heterocycloalkylene)-(phenylene)-O—$(C_1-C_3$-alkylene)- group,
a $(R^{18})$-(heterocycloalkylene)-(heteroarylene)-O—$(C_1-C_3$-alkylene)- group,
a $(R^{19})$-(heteroarylene)-O—$(C_1-C_3$-alkylene)- group,
a $(R^{18})$-(heteroarylene)-O—$(C_1-C_3$-alkylene)- group,
a $(R^{19})$—S(O)$_2$-(heteroarylene)-O—$(C_1-C_3$-alkylene)- group,
a $(R^{19})$—S(O)$_2$-(heterocycloalkylene)-(heteroarylene)-O—$(C_1-C_3$-alkylene)- group,
a $NR^{20}R^{21}$—$(C_1-C_3$-alkylene)- group,
a $(C_1-C_3$-alkyl)-NH—$(C_1-C_3$-alkylene)- group,
a $(C_1-C_3$-haloalkyl)-$(C_1-C_3$-alkylene)-NH—$(C_1-C_3$-alkylene)- group,
a $(C_1-C_3$-haloalkyl)-NH—$(C_1-C_3$-alkylene)- group,
a $(C_1-C_3$-alkyl)-NH—C(O)—$(C_1-C_3$-alkylene)- group,
a $(C_1-C_3$-alkyl)-NR$^{15}$—C(O)—$(C_1-C_3$-alkylene)- group,
a $(C_1-C_3$-alkyl)-C(O)—NH—$(C_1-C_3$-alkylene)- group,
a $(C_1-C_3$-alkyl)-C(O)—NR$^{15}$—$(C_1-C_3$-alkylene)- group,
a

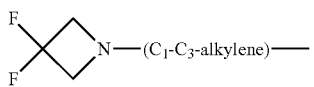

group and a

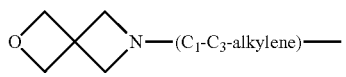

group, where the phenyl ring is unsubstituted or substituted with a halogen atom, a hydroxy group or a $C_1-C_3$-alkoxy group and the heterocycloalkyl group is unsubstituted or substituted with an oxo (=O) group or is unsubstituted or substituted with one or more substituents independently selected from a halogen atom, a hydroxy group, a $C_1-C_3$-alkyl group and a $C_1-C_3$-alkoxy group, or $R^8$ and $R^9$ together form a 5-membered or 6-membered ring optionally comprising one or two heteroatoms independently selected from —O— and —NR$^{14}$—;

$R^{14}$ is a hydrogen atom or a $C_1-C_3$-alkyl group;

$R^{16}$ and $R^{17}$ are each independently selected from a hydrogen atom, a $C_1-C_6$-alkyl group, a $C_1-C_6$-haloalkyl group, a $C_1-C_6$-alkoxy group, a $C_3-C_8$-cycloalkyl group, a $C_1-C_3$-alkyl-C(O)— group, a $C_1-C_3$-alkylS(O)$_2$— group and a $C_1-C_3$-alkyl-O—C(=O)— group;

$R^{18}$ is selected from a hydrogen atom, a hydroxy group, a cyano group, a $C_1-C_3$-alkyl group, a $C_1-C_6$-hydroxyalkyl group, a $C_1-C_3$-alkoxy group, a $R^{21}OC(O)$—$(C_1-C_3$-alkylene)- group, a —C(O)OR$^{21}$ group, a —C(O)NR$^{20}$R$^{21}$ group, a ($C_1-C_3$-alkyl)-O—$(C_1-C_3$-alkylene)-C(O)— group, a ($C_1-C_6$-alkyl)-C(O)— group and a $C_3-C_6$-cycloalkyl-C(O)— group;

$R^{19}$ is selected from a $C_1-C_3$-alkyl group, a $C_3-C_6$-cycloalkyl group and a $NR^{20}R^{21}$ group;

$R^{20}$ and $R^{21}$ are each independently selected from a hydrogen atom and a $C_1-C_6$-alkyl group;

$R^{22}$ is independently selected from, a halogen atom, a $C_1-C_6$-alkyl group which is unsubstituted or substituted with one or more substituents selected from a halogen atom, a hydroxy group, a NR$^{16}$R$^{17}$ group, a $C_1-C_3$-alkyl group, a $C_1-C_3$-haloalkyl group, a $C_1-C_3$-hydroxyalkyl group, a $C_1-C_3$-alkoxy group, a $C_1-C_3$-haloalkoxy group, a $C_3-C_6$-cycloalkyl group, a heterocycloalkyl group, an aryl group, a $(R^{18})$-(heterocycloalkylene)-(arylene)-O— group, a (heterocycloalkyl)-(arylene)-O— group, an aryl-O— group, an aryl-$(C_1-C_3$-alkylene)-O— group, a $(R^{19})$—S(O)$_2$-arylene-O— group, a $(R^{19})$S(O)$_2$-heterocycloalkylene-arylene-O— group, an aryl-heteroarylene-O— group, an aryl-heteroarylene-O—$(C_1-C_3$-alkylene)- group, a heterocycloalkyl-$(C_1-C_3$-alkylene)-C(O)— group, a heterocycloalkyl-NH—C(O)— group, an aryl-$(C_1-C_3$-alkylene)-NH—C(O)— group, a heterocycloalkylene-$(C_1-C_3$-alkylene)-S(O)$_2$— group and a heterocycloalkylene-heteroarylene-S(O)$_2$— group;

a $C_1-C_3$-alkyl-C(O)— group, a $C_3-C_6$-cycloalkyl group, an aryl group, a heterocycloalkyl group and a heteroaryl group;

whereby any heterocycloalkyl group of $R^{22}$ may optionally be itself further substituted with a $C_1-C_3$-alkyl group or one or two halogen atoms;

$R^{23}$ is a hydrogen atom;

comprising contacting a compound of formula (IIA) when A is A1, or formula (IIB) when A is A2:

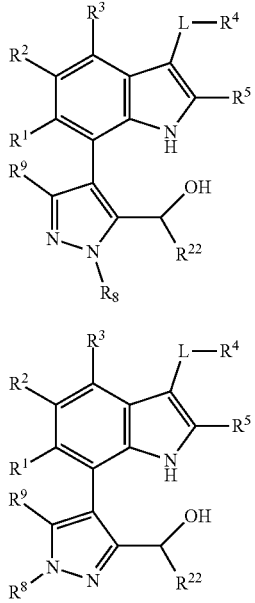

with a di-functionalized alkane

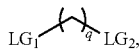

wherein
R⁵ is selected from a COO(C₁-C₆-alkyl) group, a

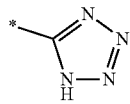

group, a —C(O)—NHS(O)₂(C₁-C₆-alkyl) group, a —C(O)—NHS(O)₂(C₃-C₆-cycloalkyl) group, a —C(O)—NHS(O)₂(aryl) group, a —C(O)—NHS(O)₂(CH₂)ₛNHCO(C₁-C₆-alkyl) group, a —C(O)—NHS(O)₂(CH₂)ₛNHCO(C₃-C₆-cycloalkyl) group and a —C(O)—NHS(O)₂(CH₂)ₛNHCO(aryl) group;
q is 2, 3, 4, 5, or 6, and
LG¹ and LG² are each independently halo or sulfonate.

In some embodiments, the present disclosure provides a method for preparing a compound of Formula (I):

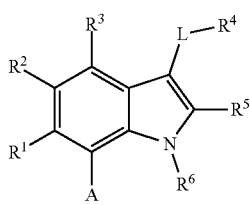

wherein
A is

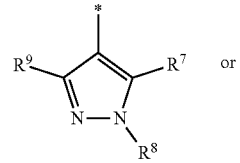

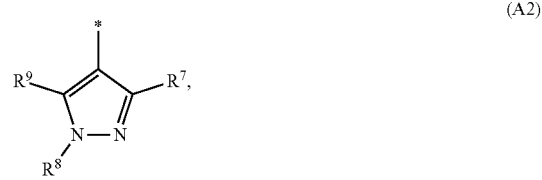

wherein R⁶ and R⁷, together with two carbon atoms of the pyrazole ring, two carbon atoms of the indole moiety and the nitrogen atom to which R⁶ is attached, form a 9-membered to 13-membered ring and * is the point of attachment of these moieties to the indole carbon atom bearing the A substituent;

R¹ and R² are each independently selected from a hydrogen atom, a halogen atom, a cyano group, a C₁-C₃-alkyl group and a C₁-C₃-alkoxy group;

R³ is selected from a hydrogen atom, a halogen atom, a cyano group, a C₁-C₃-alkyl group, a C₁-C₃-haloalkyl group, a C₁-C₃-alkoxy group and a C₃-C₈-cycloalkyl group;

R⁴ is selected from an aryl group and a heteroaryl group, each of which is unsubstituted or substituted with one, two, three; four or five substituents and each substituent is independently selected from a halogen atom, a cyano group, a C₁-C₃-alkyl group, a C₁-C₃-haloalkyl group, a C₁-C₃-alkoxy group and a C₃-C₅-cycloalkyl group;

L is a group —(CH₂)ₘ-E- wherein any CH₂ group is unsubstituted or substituted with one or two substituents and each substituent is independently selected from a halogen atom, a cyano group, a hydroxy group, a C₁-C₃-alkyl group and a C₁-C₃-alkoxy group;

E is a bond, an oxygen atom, a sulfur atom, or a —NR¹⁴— group and constitutes the connecting element to R⁴;

m is 2, 3, or 4;

R⁵ is selected from a COOH group, a COO(C₁-C₆-alkyl) group, and a

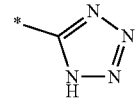

group;
—R⁶-R⁷— is #—(CH₂)ₙ—(B)ₜ—CR²²R²³—##,
wherein # is the point of attachment with the indole nitrogen atom and ## is the point of attachment with the pyrazole carbon atom bearing the R⁷ substituent; and wherein one or more —CH₂— groups may be unsubstituted or substituted with one or more substituents independently selected from a halogen atom, a hydroxy group, a NR¹⁶R¹⁷ group, a C₁-C₃-alkyl group, a C₁-C₃-haloalkyl group, a C₁-C₃-alkoxy group and a C₁-C₃-haloalkoxy group;
n is 2, 3, 4, 5 or 6;

t is 1;
where the integers selected for variables n and t, together with the methylene group $CR^{22}R^{23}$ and the other non-variable atoms of the pyrazole and the indole moiety result in forming a 9-membered to 13-membered ring independently from the selection of variable A1 or A2;
B is —O—;
$R^8$ is selected from a hydrogen atom,
  a $C_1$-$C_6$-alkyl group, which is unsubstituted or substituted with one or more substituents independently selected from
    a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group;
$R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O— group,
  a $C_1$-$C_4$-haloalkoxy group,
  a $C_1$-$C_6$-alkyl-O—($C_1$-$C_3$-alkylene)- group,
  a ($C_1$-$C_3$-alkyl)-NH—($C_1$-$C_3$-alkylene)- group,
  a ($C_3$-$C_7$)-cycloalkyl group and
  a ($C_3$-$C_7$)-cycloalkyl-O—($C_1$-$C_3$-alkylene)- group;
$R^{14}$ is a hydrogen atom or a $C_1$-$C_3$-alkyl group;
$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;
$R^{20}$ and $R^{21}$ are each independently selected from a hydrogen atom and a $C_1$-$C_6$-alkyl group;
$R^{22}$ is independently selected from
  a halogen atom
  a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group and a phenyl group,
  a $C_3$-$C_6$-cycloalkyl group and
  a phenyl group,
  whereby any heterocycloalkyl group of $R^{22}$ may optionally be itself further substituted with a $C_1$-$C_3$-alkyl group or one or two halogen atoms;
$R^{23}$ is a hydrogen atom;
comprising contacting a compound of formula (IIA) when A is A1, or formula (IIB) when A is A2:

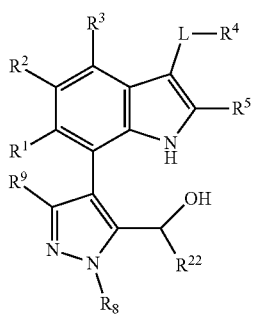

(IIA)

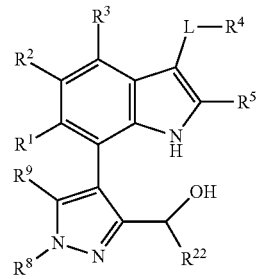

(IIB)

with a di-functionalized alkane

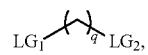

wherein
variables $R^1$, $R^2$, $R^3$, $R^4$, $R^8$, $R^9$, and $R^{22}$ are as defined above,
$R^5$ is a COO($C_1$-$C_6$-alkyl) group or a

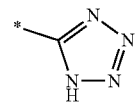

group,
q is 2, 3, 4, 5, and 6, and
$LG^1$ and $LG^2$ are each independently halo or sulfonate.
In some embodiments, the present disclosure provides a method for preparing a compound of Formula (I):

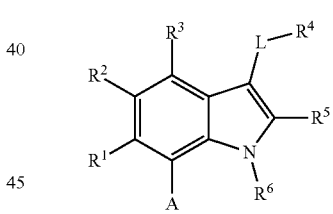

(I)

wherein
A is

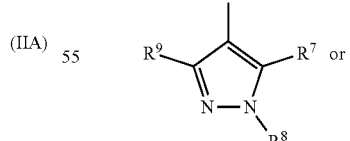

(A1)

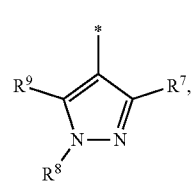

(A2)

wherein $R^6$ and $R^7$, together with two carbon atoms of the pyrazole ring, two carbon atoms of the indole moiety and the nitrogen atom to which $R^6$ is attached, form a 10-membered to 12-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two or three substituents and each substituent is independently selected from a halogen atom and a $C_1$-$C_3$-alkyl group;

L is a group —$(CH_2)_m$-E-;

E is a bond or an oxygen atom and constitutes the connecting element to $R^4$;

m is 2, 3, or 4;

$R^5$ is a COOH group or a COO($C_1$-$C_6$-alkyl) group;

—$R^6$-$R^7$— is $^\#$—$(CH_2)_n$—$(B)_t$—$CR^{22}R^{23}$—$^{\#\#}$, wherein $^\#$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group;

n is 3, 4 or 5;

t is 1;

where the integers selected for variables n and t together with the methylene group $CR^{22}R^{23}$ and the other non-variable atoms of the pyrazole and the indole moiety result in forming a 10-membered to 12-membered ring independently from the selection of variable A1 or A2

B is —O—;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group, a $C_1$-$C_3$-hydroxyalkyl group, a $C_1$-$C_3$-haloalkyl group, a $C_1$-$C_3$-alkyl-O— group, a $C_1$-$C_3$-haloalkoxy group, a $C_1$-$C_3$-alkyl-O—($C_1$-$C_3$-alkylene)- group, a ($C_3$-$C_6$)-cycloalkyl group, a $R^{19}$-(phenylene)-O—($C_1$-$C_3$-alkylene)- group, a $NR^{20}R^{21}$—($C_1$-$C_3$-alkylene)- group and a ($C_1$-$C_3$-alkyl)-NH—($C_1$-$C_3$-alkylene)- group;

$R^{14}$ is a hydrogen atom or a $C_1$-$C_3$-alkyl group;

$R^{16}$ and $R^{17}$ are each independently selected from a hydrogen atom, a $C_1$-$C_6$-alkyl group, a $C_1$-$C_6$-haloalkyl group and a $C_1$-$C_6$-alkoxy group;

$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)OR$^{21}$—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are each independently selected from a hydrogen atom and a $C_1$-$C_3$-alkyl group;

$R^{22}$ is independently selected from a halogen atom, a $C_1$-$C_6$-alkyl group which is unsubstituted or substituted with a group selected from a hydroxy group, $NR^{16}R^{17}$ group, a $C_1$-$C_3$-haloalkyl group, a $C_1$-$C_4$-alkoxy group, a $C_3$-$C_6$-cycloalkyl group, a heterocycloalkyl group and a phenyl group;

a $C_3$-$C_6$-cycloalkyl group, and a phenyl group, whereby any heterocycloalkyl group of $R^{22}$ may optionally be itself further substituted with a $C_1$-$C_3$-alkyl group or one or two halogen atoms;

$R^{23}$ is a hydrogen atom;

comprising contacting a compound of formula (IIA) when A is A1, or formula (IIB) when A is A2:

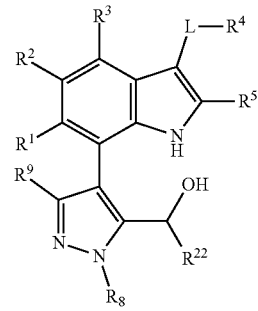

(IIA)

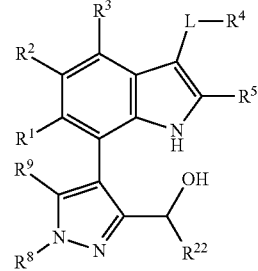

(IIB)

with a di-functionalized alkane

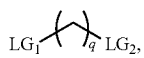

wherein variables $R^1$, $R^2$, $R^3$, $R^4$, $R^8$, $R^9$, and $R^{22}$ are as defined above, $R^5$ is —$CO_2$($C_{1-6}$alkyl), q is 3, 4, or 5, and $LG^1$ and $LG^2$ are each independently halo or sulfonate.

In some embodiments, the present disclosure provides a method for preparing a compound of Formula (I):

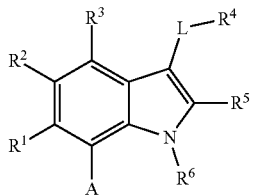
(I)

wherein
A is

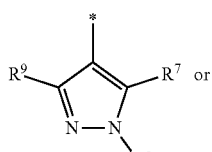
(A1)

or

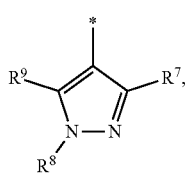
(A2), wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group —$(CH_2)_m$-E-;

E is an oxygen atom and constitutes the connecting element to $R^4$;

m is 3;

$R^5$ is a COOH group or a COO($C_1$-$C_6$-alkyl) group;

—$R^6$-$R^7$— is #—$(CH_2)_n$—(B)$_t$—$CR^{22}R^{23}$—##,
wherein # is the point of attachment with the indole nitrogen atom and ## is the point of attachment with the pyrazole carbon atom bearing the $R^7$ substituent;

n is 4;

t is 1;

where the integers selected for variables n and t together with the methylene group $CR^{22}R^{23}$ and the other non-variable atoms of the pyrazole and the indole moiety result in forming a 11-membered ring independently from the selection of variable A1 or A2;

B is —O—;

$R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group;

$R^{22}$ is independently selected from
a halogen atom,
a $C_3$-$C_6$-cycloalkyl group,
a phenyl group and
a $C_1$-$C_6$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;

whereby any heterocycloalkyl group of $R^{22}$ may optionally itself be further substituted with a $C_1$-$C_3$-alkyl group or one or two halogen atoms;

$R^{23}$ is a hydrogen atom;

comprising contacting a compound of formula (IIA) when A is A1, or formula (IIB) when A is A2:

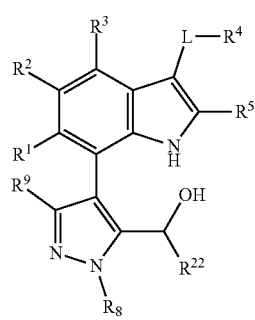
(IIA)

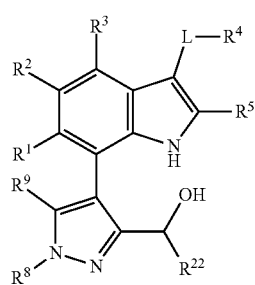
(IIB)

with a di-functionalized alkane

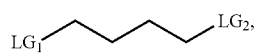

wherein
variables $R^1$, $R^2$, $R^3$, $R^4$, $R^8$, $R^9$, and $R^{22}$ are as defined above, $R^5$ is —$CO_2(C_{1-6}alkyl)$ and $LG^1$ and $LG^2$ are each independently halo or sulfonate.

In some embodiments, the present disclosure provides a method for preparing a compound of Formula (I):

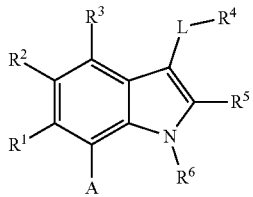

(I)

wherein
A is

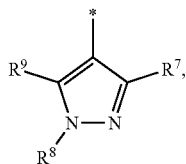

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is selected from a hydrogen atom, a fluorine atom and a chlorine atom;

$R^2$ and $R^3$ are each a hydrogen atom;

$R^4$ is a naphthyl group which is unsubstituted or substituted with a fluorine atom;

L is a group $-(CH_2)_3-O-$;

$R^5$ is a COOH group or a $COO(C_1-C_6$-alkyl) group;

$-R^6-R^7-$ is $^\#-(CH_2)_4-O-CR^{22}R^{23}-^{\#\#}$, wherein $^\#$ is the point of attachment with the indole nitrogen atom and $^{\#\#}$ is the point of attachment with the pyrazole carbon atom bearing the $R^7$ substituent;

$R^8$ is a $C_1-C_3$-alkyl group;

$R^9$ is a $C_1-C_3$-alkyl group;

$R^{22}$ is independently selected from
  a $C_3-C_6$-cycloalkyl group,
  a phenyl group and
  a $C_1-C_5$-alkyl group which is unsubstituted or substituted with a substituent selected from a hydroxy group, a $NR^{16}R^{17}$ group, a $C_1-C_3$-haloalkyl group, a $C_1-C_3$-alkoxy group, a $C_3-C_6$-cycloalkyl group, a heterocycloalkyl group and a phenyl group;
  whereby any heterocycloalkyl group of $R^{22}$ may optionally itself be further substituted with a $C_1-C_3$-alkyl group or one or two halogen atoms;

$R^{23}$ is a hydrogen atom;
comprising contacting a compound of formula (IIB):

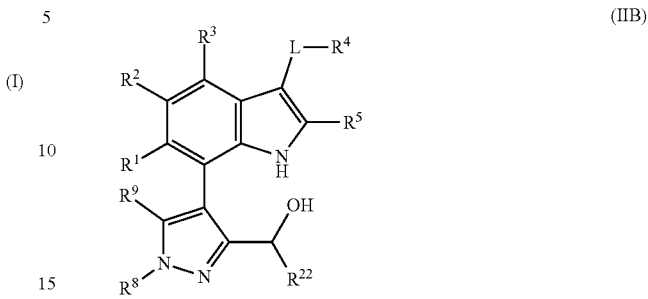

(IIB)

with a di-functionalized alkane

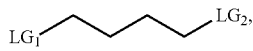

wherein
variables $R^1$, $R^2$, $R^3$, $R^4$, $R^8$, $R^9$, and $R^{22}$ are as defined above,
$R^5$ is $-CO_2(C_{1-6}alkyl)$ and
$LG^1$ and $LG^2$ are each independently halo or sulfonate.

In some embodiments, $R^1$, $R^2$ and $R^3$ are each selected from a hydrogen atom, a halogen atom and a $C_1-C_3$-alkyl group, or a tautomer, an N-oxide, or a salt thereof, or a salt of a tautomer, or a salt of an N-oxide, or a mixture of same.

In some embodiments, $R^1$ and $R^2$ are each independently selected from a hydrogen atom, a halogen atom, a cyano group, a $C_1-C_3$-alkyl group and a $C_1-C_3$-alkoxy group or a tautomer, an N-oxide, or a salt thereof, or a salt of a tautomer, or a salt of an N-oxide, or a mixture of same.

In some embodiments, $R^1$ and $R^2$ are each independently selected from a hydrogen atom and a halogen atom or a tautomer, an N-oxide, or a salt thereof, or a salt of a tautomer, or a salt of an N-oxide, or a mixture of same.

In some embodiments, $R^1$ and $R^2$ are each independently selected from a hydrogen atom, a fluorine atom and a chlorine atom or a tautomer, an N-oxide, or a salt thereof or a salt of a tautomer or a salt of an N-oxide or a mixture of same.

In some embodiments, $R^1$ is selected from a hydrogen atom, fluorine atom and a chlorine atom; and $R^2$ and $R^3$ are each a hydrogen atom; or a tautomer, an N-oxide, or a salt thereof or a salt of a tautomer or a salt of an N-oxide or a mixture of same.

In some embodiments, $R^1$ is a halogen atom or a tautomer, an N-oxide, or a salt thereof, or a salt of a tautomer, or a salt of an N-oxide, or a mixture of same.

In some embodiments, $R^1$ is a chlorine atom or a fluorine atom or a tautomer, an N-oxide, or a salt thereof, or a salt of a tautomer, or a salt of an N-oxide, or a mixture of same.

In some embodiments, $R^1$ is a chlorine atom or a tautomer, an N-oxide, or a salt thereof, or a salt of a tautomer, or a salt of an N-oxide, or a mixture of same.

In some embodiments, $R^3$ is selected from a hydrogen atom, a halogen atom, a cyano group, a $C_1-C_3$-alkyl group, a $C_1-C_3$-haloalkyl group, a $C_1-C_3$-alkoxy group, a $C_1-C_3$-alkylthio group, a $-S(O)-(C_1-C_3$-alkyl) group, a $-S(O)_2-(C_1-C_3$-alkyl) group, a $C_1-C_3$-haloalkoxy group, a $C_1-C_3$-haloalkylthio group and a $C_3-C_5$-cycloalkyl group or a tautomer, an N-oxide, or a salt thereof, or a salt of a tautomer, or a salt of an N-oxide, or a mixture of same.

In some embodiments, $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group or a tautomer, an N-oxide, or a salt thereof, or a salt of a tautomer, or a salt of an N-oxide, or a mixture of same.

In some embodiments, $R^3$ is a hydrogen atom or a tautomer, an N-oxide, or a salt thereof or a salt of a tautomer or a salt of an N-oxide or a mixture of same.

In some embodiments, $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group; or a tautomer, an N-oxide, or a salt thereof or a salt of a tautomer or a salt of an N-oxide or a mixture of same.

In some embodiments, $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group; or a tautomer, an N-oxide, or a salt thereof or a salt of a tautomer or a salt of an N-oxide or a mixture of same.

In other embodiments, $R^4$ is selected from an aryl group and a heteroaryl group, each of which is unsubstituted or substituted with one, two or three substituents and each substituent is independently selected from a halogen atom and a $C_1$-$C_3$-alkyl group; or a tautomer, an N-oxide, or a salt thereof or a salt of a tautomer or a salt of an N-oxide or a mixture of same.

In other embodiments, $R^4$ is selected from an aryl group and a heteroaryl group, each of which is unsubstituted or substituted with one or two substituents and each substituent is independently selected from a halogen atom and a $C_1$-$C_3$-alkyl group or a tautomer, an N-oxide, or a salt thereof or a salt of a tautomer or a salt of an N-oxide or a mixture of same.

In other embodiments, $R^4$ is selected from naphthyl group which is unsubstituted or substituted with a fluorine atom or a chlorine atom or a tautomer, an N-oxide, or a salt thereof, or a salt of a tautomer, or a salt of an N-oxide, or a mixture of same.

In other embodiments, $R^4$ is selected from naphthyl group which is unsubstituted or substituted with a fluorine atom or a tautomer, an N-oxide, or a salt thereof, or a salt of a tautomer, or a salt of an N-oxide, or a mixture of same.

In other embodiments, $R^4$ is selected from naphth-1-yl group and 6-fluoro-naphth-1-yl group or a tautomer, an N-oxide, or a salt thereof, or a salt of a tautomer, or a salt of an N-oxide, or a mixture of same.

In other embodiments, $R^4$ is a naphth-1-yl group or a tautomer, an N-oxide, or a salt thereof, or a salt of a tautomer, or a salt of an N-oxide, or a mixture of same.

In other embodiments, $R^4$ is a 6-fluoro-naphth-1-yl group or a tautomer, an N-oxide, or a salt thereof, or a salt of a tautomer, or a salt of an N-oxide, or a mixture of same.

In other embodiments, L is a group —$(CH_2)_m$-E- which is optionally substituted with one or two substituents and each substituent is independently selected from a halogen atom, a cyano group, a hydroxy group, a $C_1$-$C_3$-alkyl group and a $C_1$-$C_3$-alkoxy group, or two substituents are taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —$NR^{14}$— group or a tautomer, an N-oxide, or a salt thereof, or a salt of a tautomer, or a salt of an N-oxide, or a mixture of same.

In other embodiments, L is a group —$(CH_2)_m$-E- which is optionally substituted with one or two substituents and each substituent is independently selected from a halogen atom, a hydroxy group, a $C_1$-$C_3$-alkyl group and a $C_1$-$C_3$-alkoxy group, or two substituents are taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a —S(O)— group, a —S(O)$_2$— group and a —$NR^{14}$— group, or a tautomer, an N-oxide, or a salt thereof, or a salt of a tautomer, or a salt of an N-oxide, or a mixture of same.

In other embodiments, L is a group —$(CH_2)_m$-E- wherein any $CH_2$ group is unsubstituted or substituted with one or two substituents and each substituent is independently selected from a halogen atom, a cyano group, a hydroxy group, a $C_1$-$C_3$-alkyl group and a $C_1$-$C_3$-alkoxy group or a tautomer, an N-oxide, or a salt thereof, or a salt of a tautomer, or a salt of an N-oxide, or a mixture of same.

In other embodiments, L is a group —$(CH_2)_m$-E- or a tautomer, an N-oxide, or a salt thereof, or a salt of a tautomer, or a salt of an N-oxide, or a mixture of same.

In other embodiments, L is a group —$(CH_2)_m$-E- and m is 2, 3, or 4 or a tautomer, an N-oxide, or a salt thereof, or a salt of a tautomer, or a salt of an N-oxide, or a mixture of same.

In other embodiments, L is a group —$(CH_2)_m$-E- and m is 3 or a tautomer, an N-oxide, or a salt thereof, or a salt of a tautomer, or a salt of an N-oxide, or a mixture of same.

In other embodiments, L is an unsubstituted group —$(CH_2)_m$-E- or a tautomer, an N-oxide, or a salt thereof, or a salt of a tautomer, or a salt of an N-oxide, or a mixture of same.

In other embodiments, L is an unsubstituted group —$(CH_2)_m$-E-, E is oxygen or $NR^{15}$ and m is 3 or a tautomer, an N-oxide, or a salt thereof, or a salt of a tautomer, or a salt of an N-oxide, or a mixture of same.

In other embodiments, L is an unsubstituted group —$(CH_2)_m$-E-, E is oxygen and m is 3, or a tautomer, an N-oxide, or a salt thereof, or a salt of a tautomer, or a salt of an N-oxide, or a mixture of same.

In other embodiments, L is a group —$(CH_2)_3$—O— or a tautomer, an N-oxide, or a salt thereof, or a salt of a tautomer, or a salt of an N-oxide, or a mixture of same.

In further embodiments, E is an oxygen atom, or a tautomer, an N-oxide, or a salt thereof, or a salt of a tautomer, or a salt of an N-oxide, or a mixture of same.

In other embodiments, L is an unsubstituted group —$(CH_2)_m$-E- and E is an oxygen atom or a tautomer, an N-oxide, or a salt thereof, or a salt of a tautomer, or a salt of an N-oxide, or a mixture of same.

In further embodiments, $R^5$ is a COOH group, or a tautomer, an N-oxide, or a salt thereof, or a salt of a tautomer, or a salt of an N-oxide, or a mixture of same.

In further embodiments, $R^5$ is a COO($C_{1-6}$alkyl) group, or a tautomer, an N-oxide, or a salt thereof, or a salt of a tautomer, or a salt of an N-oxide, or a mixture of same. In some embodiments, $R^5$ is a COO($C_{1-3}$alkyl) group, such as COOMe, COOEt, and COOPr, preferably COOEt.

In other embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups are unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group, or a tautomer, an N-oxide, or a salt thereof, or a salt of a tautomer, or a salt of an N-oxide, or a mixture of same.

In further embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups are unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, or a tautomer, an N-oxide, or a salt thereof, or a salt of a tautomer, or a salt of an N-oxide, or a mixture of same.

In further embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups are unsubstituted or substituted with one or more substituents independently selected from a halogen atom, a hydroxy group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, or a tautomer, an N-oxide, or a salt thereof, or a salt of a tautomer, or a salt of an N-oxide, or a mixture of same.

In other embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom or a tautomer, or a salt thereof, or a salt of a tautomer, or a mixture of same.

In other embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups are unsubstituted or substituted with one or more substituents independently selected from a halogen atom or a tautomer, or a salt thereof, or a salt of a tautomer, or a mixture of same.

In other embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent or a tautomer, or a salt thereof, or a salt of a tautomer, or a mixture of same.

In other embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent and wherein one or more —$CH_2$— groups may be unsubstituted or a tautomer, or a salt thereof or a salt of a tautomer or a salt of an N-oxide or a mixture of same.

In other embodiments, —$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent and wherein one or more —$CH_2$— groups are substituted with one or more substituents independently selected from a halogen atom or a tautomer, or a salt thereof or a salt of a tautomer or a salt of an N-oxide or a mixture of same.

In other embodiments, —$R^6$-$R^7$— is $^{\#}$—$(CH_2)_n$—O—$CR^{22}R^{23}$—$^{\#\#}$, or a tautomer, an N-oxide, or a salt thereof, a salt of an N-oxide, or a salt of a tautomer or a mixture of same.

In other embodiments, —$R^6$-$R^7$— is is $^{\#}$—$(CH_2)_4$—O—$CR^{22}R^{23}$—$^{\#\#}$ or a tautomer, an N-oxide, or a salt thereof or a salt of a tautomer, a salt of an N-oxide, or a mixture of same.

In other embodiments, —$R^6$-$R^7$— is selected from $^{\#}$—$(CH_2)_4$—O—$CH(CH_3)$—$^{\#\#}$, $^{\#}$—$(CH_2)_4$—O—CH[$(CH_2)_2$-morpholino]-$^{\#\#}$, $^{\#}$—$(CH_2)_4$—O—CH[$(CH_2)_2$-N-methylpiperazino]-$^{\#\#}$, $^{\#}$—$(CH_2)_4$—O—CH[$(CH_2)_2$-pyrrolidino]-$^{\#\#}$, $^{\#}$—$(CH_2)_4$—O—CH[$(CH_2)_2$-cyclopropyl]-$^{\#\#}$, $^{\#}$—$(CH_2)_4$—O—CH(cyclopropyl)-$^{\#\#}$, $^{\#}$—$(CH_2)_4$—O—CH[$(CH_2)_2$—O—$CH_3$]-$^{\#\#}$, $^{\#}$—$(CH_2)_4$—O—CH[$(CH_2)_2$—OH]-$^{\#\#}$, $^{\#}$—$(CH_2)_4$—O—CH($CH_2CH_3$)—$^{\#\#}$, and $^{\#}$—$(CH_2)_4$—O—CH($CF_3$)—$^{\#\#}$, or a tautomer, or a salt thereof, or a salt of a tautomer, or a mixture of same.

In other embodiments, —$R^6$-$R^7$— is selected from $^{\#}$—$(CH_2)_4$—O—$CH(CH_3)$—$^{\#\#}$, $^{\#}$—$(CH_2)_4$—O—CH[$(CH_2)_2$-morpholino]-$^{\#\#}$, $^{\#}$—$(CH_2)_4$—O—CH(cyclopropyl)-$^{\#\#}$, $^{\#}$—$(CH_2)_4$—O—CH[$(CH_2)_2$—OH]-$^{\#\#}$ $^{\#}$—$(CH_2)_4$—O—CH($CH_2CH_3$)—$^{\#\#}$, and $^{\#}$—$(CH_2)_4$—O—CH($CF_3$)—$^{\#\#}$, or a tautomer, or a salt thereof, or a salt of a tautomer, or a mixture of same.

In other embodiments, —$R^6$-$R^7$— is selected from $^{\#}$—$(CH_2)_4$—O—$CH(CH_3)$—$^{\#\#}$, $^{\#}$—$(CH_2)_4$—O—CH[$(CH_2)_2$-(oxan-4-yl)]-$^{\#\#}$, $^{\#}$—$(CH_2)_4$—O—CH[$(CH_2)_2$-morpholino]-$^{\#\#}$, $^{\#}$—$(CH_2)_4$—O—CH[$(CH_2)_2$-(4-methylpiperazin-1-yl)]-$^{\#\#}$, $^{\#}$—$(CH_2)_4$—O—CH[$(CH_2)_2$-(3,3-difluoropyrrolidin-1-yl)]-$^{\#\#}$, $^{\#}$—$(CH_2)_4$—O—CH[$(CH_2)_2$-(3-fluoroazetidin-1-yl)]-$^{\#\#}$, $^{\#}$—$(CH_2)_4$—O—CH[$(CH_2)_2$-(3,3-difluoroazetidin-1-yl)]-$^{\#\#}$, $^{\#}$—$(CH_2)_4$—O—CH(cyclopropyl)-$^{\#\#}$, $^{\#}$—$(CH_2)_4$—O—CH(phenyl)-$^{\#\#}$, $^{\#}$—$(CH_2)_4$—O—CH($CH_2$-phenyl)-$^{\#\#}$, $^{\#}$—$(CH_2)_4$—O—CH[$(CH_2)_2$-morpholino]-$^{\#\#}$, $^{\#}$—$(CH_2)_4$—O—CH[$(CH_2)_2$—OH]-$^{\#\#}$, $^{\#}$—$(CH_2)_4$—O—$CH_2C(CH_3)_2(OH)$—$^{\#\#}$, $^{\#}$—$(CH_2)_4$—O—$(CH_2)_2C(CH_3)_2(OH)$—$^{\#\#}$, $^{\#}$—$(CH_2)_4$—O—CH[$(CH_2)_2$—$OCH_3$]—$^{\#\#}$, $^{\#}$—$(CH_2)_4$—O—CH[$(CH_2)_2N(CH_3)(OCH_3)$]-$^{\#\#}$, $^{\#}$—$(CH_2)_4$—O—CH[$(CH_2)_2N(CH_3)_2$]—$^{\#\#}$, $^{\#}$—$(CH_2)_4$—O—CH($CH_2CH_3$)—$^{\#\#}$, $^{\#}$—$(CH_2)_4$—O—CH($CF_3$)—$^{\#\#}$, or a tautomer, or a salt thereof, or a salt of a tautomer, or a mixture of same.

In further embodiments, n is 2, 3, 4, 5 or 6; and t is 1 or a tautomer, an N-oxide, or a salt thereof, or a salt of a tautomer, or a salt of an N-oxide, or a mixture of same.

In further embodiments, n is 3, 4 or 5; and t is 1 or a tautomer, an N-oxide, or a salt thereof, or a salt of a tautomer, or a salt of an N-oxide, or a mixture of same.

In further embodiments, n is 4 or 5; and t is 1 or a tautomer, an N-oxide, or a salt thereof, or a salt of a tautomer, or a salt of an N-oxide, or a mixture of same.

In further embodiments, n is 4 and t is 1 or a tautomer, an N-oxide, or a salt thereof, or a salt of a tautomer, or a salt of an N-oxide, or a mixture of same.

In further embodiments, B is an oxygen atom or a tautomer, or a salt thereof, or a salt of a tautomer, or a mixture of same.

In further embodiments, A is A1 or A2, or a tautomer, an N-oxide, or a salt thereof, or a salt of a tautomer, or a salt of an N-oxide, or a mixture of same.

In other embodiments, A is A1, or a tautomer, an N-oxide, or a salt thereof, or a salt of a tautomer, or a salt of an N-oxide, or a mixture of same.

In further embodiments, A is A2, or a tautomer, an N-oxide, or a salt thereof, or a salt of a tautomer, or a salt of an N-oxide, or a mixture of same.

In other embodiments, A is A1 or A2 and the macrocyclic ring is a 9-membered ring, a 10-membered ring, a 11-membered ring, a 12-membered ring, or a 13-membered ring, preferably a 9-membered to 12-membered ring, or a 12-membered to a 13-membered ring, more preferably a 10-membered to 11-membered ring, or a tautomer, an N-oxide, or a salt thereof, or a salt of a tautomer, or a salt of an N-oxide, or a mixture of same.

In other embodiments, A is A1 or A2, which together with the indole moiety and the $R^6$—$R^7$ form a 9-membered macrocyclic ring, a 10-membered macrocyclic ring or a 11-membered macrocyclic ring or a tautomer, an N-oxide, or a salt thereof, or a salt of a tautomer, or a salt of an N-oxide, or a mixture of same.

In other embodiments, A is A1 or A2, which together with the indole moiety and the $R^6$—$R^7$ form a 9-membered macrocyclic ring, a 10-membered macrocyclic ring, a 11-membered macrocyclic ring or a 12-membered macrocyclic ring or a tautomer, an N-oxide, or a salt thereof, or a salt of a tautomer, or a salt of an N-oxide, or a mixture of same.

In other embodiments, A is A1, which together with the indole moiety and the $R^6$—$R^7$ form a 9-membered macrocyclic ring, a 10-membered macrocyclic ring or a 11-membered macrocyclic ring or a tautomer, or a salt thereof, or a salt of a tautomer, or a mixture of same.

In yet other embodiments, A is A1, which together with the indole moiety and the $R^6$—$R^7$ form a 9-membered macrocyclic ring, a 10-membered macrocyclic ring, a 11-membered macrocyclic ring or a 12-membered macrocyclic ring or a tautomer, an N-oxide, or a salt thereof, or a salt of a tautomer, or a salt of an N-oxide, or a mixture of same.

In yet other embodiments, A is A2, which together with the indole moiety and the $R^6$—$R^7$ form a 9-membered macrocyclic ring, a 10-membered macrocyclic ring or a 11-membered macrocyclic ring or a tautomer, or a salt thereof, or a salt of a tautomer, or a mixture of same.

In yet other embodiments, A is A2, which together with the indole moiety and the $R^6$—$R^7$ form a 9-membered macrocyclic ring, a 10-membered macrocyclic ring, a 11-membered macrocyclic ring or a 12-membered macrocyclic ring or a tautomer, an N-oxide, or a salt thereof, or a salt of a tautomer, or a salt of an N-oxide, or a mixture of same.

In yet other embodiments, A is A1 or A2, which together with the indole moiety and the $R^6$—$R^7$ form a 10-membered macrocyclic ring or a 11-membered macrocyclic ring or a tautomer, an N-oxide, or a salt thereof, or a salt of a tautomer, or a salt of an N-oxide, or a mixture of same.

In yet other embodiments, A is A1 or A2, which together with the indole moiety and the $R^6$—$R^7$ form a 11-membered macrocyclic ring or a tautomer, an N-oxide, or a salt thereof, or a salt of a tautomer, or a salt of an N-oxide, or a mixture of same.

In yet other embodiments, A is A1 or A2 and $R^8$ and $R^9$ are independently selected from $C_1$-$C_3$-alkyl, preferably methyl or ethyl or a tautomer, an N-oxide, or a salt thereof, or a salt of a tautomer, or a salt of an N-oxide, or a mixture of same.

In yet other embodiments, A is A1 and $R^8$ and $R^9$ are independently selected from $C_1$-$C_3$-alkyl, preferably methyl or ethyl or a tautomer, an N-oxide, or a salt thereof, or a salt of a tautomer, or a salt of an N-oxide, or a mixture of same.

In still other embodiments, A is A2 and $R^8$ and $R^9$ are independently selected from $C_1$-$C_3$-alkyl, preferably from methyl or ethyl or a tautomer, an N-oxide, or a salt thereof, or a salt of a tautomer, or a salt of an N-oxide, or a mixture of same.

In further embodiments, $R^8$ is selected from
a hydrogen atom,
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group;
a $C_1$-$C_3$-haloalkyl group,
a $C_3$-$C_6$-cycloalkyl group and
a $C_1$-$C_6$-alkyl group in which one or two not directly adjacent carbon atoms are
independently replaced by a hetero atom selected from —O— and —NH—, or a tautomer, an N-oxide, or a salt thereof or a salt of a tautomer or a salt of an N-oxide or a mixture of same.

In further embodiments, $R^8$ is selected from
a hydrogen atom,
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy
group, a $C_3$-$C_6$-cycloalkyl group, a heterocycloalkyl group and a $NR^{20}R^{21}$ group, or a tautomer, an N-oxide, or a salt thereof, or a salt of a tautomer, or a salt of an N-oxide, or a mixture of same.

In further embodiments, $R^8$ is selected from a hydrogen atom, a $C_1$-$C_4$-alkyl group, which is unsubstituted or substituted with one or more substituents
independently selected from a halogen atom, a hydroxy group, a $C_3$-$C_6$-cycloalkyl
group and a heterocycloalkyl group; or a tautomer, an N-oxide, or a salt thereof or a salt of a tautomer or a salt of an N-oxide or a mixture of same.

In further embodiments, $R^8$ is a $C_1$-$C_6$-alkyl group or a tautomer, an N-oxide, or a salt thereof, or a salt of a tautomer, or a salt of an N-oxide, or a mixture of same.

In further embodiments, $R^8$ is a methyl group or a tautomer, an N-oxide, or a salt thereof, or a salt of a tautomer, or a salt of an N-oxide, or a mixture of same.

In further embodiments, $R^8$ is selected from a hydrogen atom and a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group or a tautomer, or a salt thereof, or a salt of a tautomer, or a mixture of same.

In further embodiments, $R^8$ is a $C_1$-$C_3$-alkyl group; or a tautomer, or a salt thereof, or a salt of a tautomer, or a mixture of same.

In further embodiments, $R^9$ is selected from a hydrogen atom,
a $C_1$-$C_4$-alkyl group,
a $C_1$-$C_3$-hydroxyalkyl group,
a $C_1$-$C_4$-haloalkyl group, a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{19}$-phenyl-($C_1$-$C_3$-alkylene)-O—($C_1$-$C_3$-alkylene)- group,
a $R^{19}$-phenylene-O—($C_1$-$C_3$-alkylene)- group,
a $R^{19}$-phenyl-heteroaryl-O—($C_1$-$C_3$-alkylene) group,
a ($R^{19}$)-(heterocycloalkyl)-($C_1$-$C_3$-alkylene)- group,
a ($R^{19}$)-(heterocycloalkylene)-(phenylene)-O—($C_1$-$C_3$-alkylene)- group,
a (heterocycloalkenylene)-(phenylene)-O—($C_1$-$C_3$-alkylene)- group,
a ($R^{19}$)-(heteroaryl-($C_1$-$C_3$-alkylene)-O—($C_1$-$C_3$-alkylene)- group,
a ($R^{19}$)-(heteroaryl)-(phenylene)-O—($C_1$-$C_3$-alkylene)- group,
a ($R^{20}$)—S(O)$_2$-(phenylene)-O—($C_1$-$C_3$-alkylene)- group,
a ($R^{20}$)—S(O)$_2$—NH-(phenylene)-O—($C_1$-$C_3$-alkylene)- group,
a ($R^{20}$)—S(O)$_2$—NH-(phenylene)-O—($C_1$-$C_3$-alkylene)- group,
a ($R^{20}$)—S(O)$_2$—N($C_1$-$C_6$-alkyl)-(phenylene)-O—($C_1$-$C_3$-alkylene)- group,
a ($R^{20}$)—S(O)$_2$-(heterocycloalkylene)-(phenylene)-O—($C_1$-$C_3$-alkylene)- group,
a ($R^{19}$)-(heterocycloalkylene)-(heteroarylene)-O—($C_1$-$C_3$-alkylen)- group,
a ($R^{20}$)-(heteroarylene)-O—($C_1$-$C_3$-alkylene)- group,
a ($R^{19}$)-(heteroarylene)-O—($C_1$-$C_3$-alkylene)- group,
a ($R^{20}$)—S(O)$_2$-(heteroarylene)-O—($C_1$-$C_3$-alkylene)- group,
a ($R^{20}$)—S(O)$_2$-(heterocycloalkylene)-(heteroarylene)-O—($C_1$-$C_3$-alkylene)- group,
a $NR^{20}R^{21}$_($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—$NR^{15}$—($C_1$-$C_3$-alkylene)- group,
a

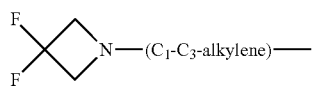

group and a

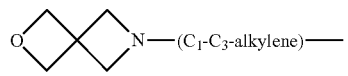

group, where the phenyl ring is optionally substituted with a halogen atom, a hydroxy group, or a $C_1$-$C_3$-alkoxy group and
the heterocycloalkyl group is optionally substituted with an oxo (=O) group or is optionally substituted with one or more substituents independently selected from a halogen atom and a $C_1$-$C_3$-alkyl group, or a tautomer, an N-oxide, or a salt thereof, or a salt of a tautomer, or a salt of an N-oxide, or a mixture of same.

In further embodiments, $R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group and
a ($C_3$-$C_7$)-cycloalkyl-O—($C_1$-$C_3$-alkylene)- group;
and where
$R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)$OR^{21}$—($C_1$-$C_3$-alkylene)- group, a —C(O)$OR^{21}$ group, a —C(O)$NR^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;
where $R^{19}$ is selected from a $C_1$-$C_3$-alkyl group, a $C_3$-$C_6$-cycloalkyl group and a $NR^{20}R^{21}$ group
where $R^{20}$ and $R^{21}$ are independently selected from a hydrogen atom or a $C_1$-$C_6$-alkyl group;
or a tautomer, an N-oxide, or a salt thereof, or a salt of a tautomer, or a salt of an N-oxide, or a mixture of same.

In further embodiments,
$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group and
a ($C_3$-$C_7$)-cycloalkyl-O—($C_1$-$C_3$-alkylene)- group;
or a tautomer, an N-oxide, or a salt thereof, or a salt of a tautomer, or a salt of an N-oxide, or a mixture of same.

In further embodiments,
$R^9$ is a $C_1$-$C_4$-alkyl group,
a $C_1$-$C_3$-hydroxyalkyl group,
a $C_1$-$C_3$-haloalkyl group,
a $C_1$-$C_3$-alkyl-O— group,
a $C_1$-$C_3$-haloalkoxy group,
a $C_1$-$C_3$-alkyl-O—($C_1$-$C_3$-alkylene)- group,
a ($C_3$-$C_6$)-cycloalkyl group,
a $R^{19}$-(phenylene)-O—($C_1$-$C_3$-alkylene)- group,
a $NR^{20}R^{21}$—($C_1$-$C_3$-alkylene)- group and
a ($C_1$-$C_3$-alkyl)-NH—($C_1$-$C_3$-alkylene)- group;
or a tautomer, an N-oxide, or a salt thereof, or a salt of a tautomer, or a salt of an N-oxide, or a mixture of same.

In further embodiments, $R^9$ is a $C_1$-$C_4$-alkyl group or a tautomer, or a salt thereof, or a salt of a tautomer, or a mixture of same.

In further embodiments, $R^9$ is a $C_1$-$C_3$-alkyl group or a tautomer, or a salt thereof, or a salt of a tautomer, or a mixture of same.

In further embodiments, $R^9$ is an ethyl group or a tautomer, or a salt thereof, or a salt of a tautomer, or a mixture of same.

In further embodiments, $R^8$ and $R^9$ together form a 5-membered ring or a 6-membered ring optionally comprising one or two heteroatoms independently selected from —O— and —$NR^{14}$—; or a tautomer, an N-oxide, or a salt thereof, or a salt of a tautomer, or a salt of an N-oxide, or a mixture of same.

In yet further embodiments, $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group; or a tautomer, or a salt thereof, or a salt of a tautomer, or a mixture of same.

In yet further embodiments, $R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group; or a tautomer, or a salt thereof, or a salt of a tautomer, or a mixture of same.

In yet further embodiments, $R^{16}$ and $R^{17}$ are each independently selected from a hydrogen atom, a $C_1$-$C_6$-alkyl group, a $C_1$-$C_6$-haloalkyl group and a $C_1$-$C_6$-alkoxy group; or a tautomer, or a salt thereof, or a salt of a tautomer, or a mixture of same.

In yet further embodiments, $R^{16}$ and $R^{17}$ are each independently selected from a hydrogen atom, a $C_1$-$C_6$-alkyl group, and a $C_1$-$C_6$-haloalkyl group; or a tautomer, or a salt thereof, or a salt of a tautomer, or a mixture of same.

In yet further embodiments, $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group; or a tautomer, or a salt thereof, or a salt of a tautomer, or a mixture of same.

In yet further embodiments, $R^{18}$ is selected from a hydrogen atom, a hydroxy group, a cyano group, a $C_1$-$C_3$-alkyl group, a $C_1$-$C_6$-hydroxyalkyl group, a $C_1$-$C_3$-alkoxy group, a C(O)O$R^{21}$—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_3$-alkyl)-C(O)— group and a $C_3$-$C_6$-cycloalkyl-C(O)— group or a tautomer, or a salt thereof, or a salt of a tautomer, or a mixture of same.

In yet further embodiments, $R^{19}$ is selected from a $C_1$-$C_3$-alkyl group, a $C_3$-$C_6$-cycloalkyl group and a $NR^{20}R^{21}$ group or a tautomer, or a salt thereof, or a salt of a tautomer, or a mixture of same.

In yet further embodiments, $R^{20}$ and $R^{21}$ are each independently selected from a hydrogen atom and a $C_1$-$C_6$-alkyl group; or a tautomer, an N-oxide, or a salt thereof, or a salt of a tautomer, or a salt of an N-oxide, or a mixture of same.

In yet further embodiments, $R^{20}$ and $R^{21}$ are each independently selected from a hydrogen atom and a $C_1$-$C_3$-alkyl group; or a tautomer, an N-oxide, or a salt thereof, or a salt of a tautomer, or a salt of an N-oxide, or a mixture of same.

In yet further embodiments, $R^{22}$ is independently selected from
a halogen atom
a $C_1$-$C_6$-alkyl group
which is unsubstituted or substituted with one or more substituents selected from a halogen atom, a hydroxy group, $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group;
a $C_1$-$C_3$-alkylene-C(O)— group,
a $C_3$-$C_6$-cycloalkyl group, and
an aryl group;
whereby any heterocycloalkyl group of $R^{22}$ may optionally be itself further substituted with a $C_1$-$C_3$-alkyl group or one or two halogen atoms;
or a tautomer, an N-oxide, or a salt thereof, or a salt of a tautomer, or a salt of an N-oxide, or a mixture of same.

In yet further embodiments, $R^{22}$ is independently selected from
a halogen atom
a $C_1$-$C_6$-alkyl group
which is unsubstituted or substituted with one or more substituents selected from a halogen atom, a hydroxy group, $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$— heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group and a heterocycloalkylene-heteroarylene-S(O)$_2$— group; and
a $C_1$-$C_3$-alkylene-C(O)— group,
or a tautomer, an N-oxide, or a salt thereof, or a salt of a tautomer, or a salt of an N-oxide, or a mixture of same.

In yet further embodiments, $R^{22}$ is independently selected from
a halogen atom,
a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group and a phenyl group,
a $C_3$-$C_6$-cycloalkyl group,
a phenyl group and
a heterocycloalkyl group, and
a heteroaryl group;

whereby any heterocycloalkyl group of $R^{22}$ may optionally be itself further substituted with a $C_1$-$C_3$-alkyl group or one or two halogen atoms;
or a tautomer, an N-oxide, or a salt thereof, or a salt of a tautomer, or a salt of an N-oxide, or a mixture of same.

In further embodiments, $R^{22}$ is independently selected from
a halogen atom
a $C_1$-$C_6$-alkyl group which is unsubstituted or substituted with one or more substituents selected from a halogen atom, a hydroxy group, $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group,
a $C_3$-$C_6$-cycloalkyl group,
a heterocycloalkyl group,
a phenyl group, and
a heteroaryl group
or a tautomer, an N-oxide, or a salt thereof, or a salt of a tautomer, or a salt of an N-oxide, or a mixture of same.

In further embodiments, $R^{22}$ is independently selected from
a halogen atom,
a $C_1$-$C_4$-alkyl group which is unsubstituted or substituted with a group selected from a hydroxy group, $NR^{16}R^{17}$ group, a $C_1$-$C_3$-haloalkyl group, a $C_1$-$C_4$-alkoxy group, a $C_3$-$C_6$-cycloalkyl group, a heterocycloalkyl group and a phenyl group;
a $C_3$-$C_6$-cycloalkyl group,
a phenyl group,
a heteroaryl group, and
a heterocycloalkyl group;
whereby any heterocycloalkyl group of $R^{22}$ may optionally be itself further substituted with a $C_1$-$C_3$-alkyl group or one or two halogen atoms; or a tautomer, an N-oxide, or a salt thereof, or a salt of a tautomer, or a salt of an N-oxide, or a mixture of same.

In further embodiments, $R^{22}$ is independently selected from
a halogen atom,
a $C_1$-$C_4$-alkyl group which is unsubstituted or substituted with a group selected from a hydroxy group, $NR^{16}R^{17}$ group, a $C_1$-$C_4$-alkoxy group, a $C_3$-$C_6$-cycloalkyl group, a heterocycloalkyl group and a phenyl group;
a phenyl group,
a heteroaryl group
a $C_3$-$C_6$-cycloalkyl group, and
a heterocycloalkyl group,
or a tautomer, an N-oxide, or a salt thereof, or a salt of a tautomer, or a salt of an N-oxide, or a mixture of same.

In further embodiments, $R^{22}$ is independently selected from
a halogen atom,
a $C_3$-$C_6$-cycloalkyl group,
a phenyl group, and
a $C_1$-$C_5$-alkyl group which is unsubstituted or substituted with one or more substituents selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group and a phenyl group;
whereby any heterocycloalkyl group of $R^{22}$ may optionally itself be further substituted with a $C_1$-$C_3$-alkyl group or one or two halogen atoms; or a tautomer, an N-oxide, or a salt thereof, or a salt of a tautomer, or a salt of an N-oxide, or a mixture of same.

In further embodiments, $R^{22}$ is independently selected from
a halogen atom,
a phenyl group,
a $C_3$-$C_6$-cycloalkyl group, and
a $C_1$-$C_3$-alkyl group which is unsubstituted or substituted with one or more substituents selected from a hydroxy group, $NR^{17}R^{18}$ group, a $C_1$-$C_3$-haloalkyl group, a $C_1$-$C_3$-alkoxy group, a $C_3$-$C_6$-cycloalkyl group, a heterocycloalkyl group and a phenyl group;
or a tautomer, or a salt thereof, or a salt of a tautomer, or a mixture of same.

In yet further embodiments, $R^{22}$ is independently selected from
a $C_3$-$C_6$-cycloalkyl group,
a phenyl group, and
a $C_1$-$C_5$-alkyl group which is unsubstituted or substituted with a substituent selected from
a hydroxy group, a $NR^{16}R^{17}$ group, a $C_1$-$C_3$-haloalkyl group, a $C_1$-$C_3$-alkoxy group,
a $C_3$-$C_6$-cycloalkyl group, a heterocycloalkyl group and a phenyl group;
whereby any heterocycloalkyl group of $R^{22}$ may optionally itself be further substituted with a $C_1$-$C_3$-alkyl group or one or two halogen atoms; or a tautomer, or a salt thereof, or a salt of a tautomer, or a mixture of same.

In yet further embodiments, $R^{22}$ is independently selected from a $C_1$-$C_3$-haloalkyl- group, and a $C_1$-$C_3$-alkyl group which is unsubstituted or substituted with a hydroxy group, a $C_3$-$C_5$-cycloalkyl group, or a heterocyclyl group; or a tautomer, or a salt thereof, or a salt of a tautomer, or a mixture of same.

In other embodiments, $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a —$(CH_2)_2$-morpholino group, a —$(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, and a phenylmethyl group or a tautomer, or a salt thereof, or a salt of a tautomer, or a mixture of same.

In other embodiments, $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a —$(CH_2)_2$-morpholino group, a —$(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, and a phenylmethyl group or a tautomer, or a salt thereof, or a salt of a tautomer, or a mixture of same.

In other embodiments, $R^{22}$ is independently selected from a —$(CH_2)_2$-morpholino group, a —$(CH_2)_3$-morpholino group, a (3,3-difluoropyrrolidin-1-yl)ethyl group, a (3,3-difluoroazetidin-1-yl)ethyl group, a 3-fluoroazetidin-1-yl) ethyl group, a 2-(oxan-4-yl)ethyl group, a (4-methylpiperazin-1-yl)ethyl group, or a tautomer, or a salt thereof, or a salt of a tautomer, or a mixture of same.

In other embodiments, $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a cyclopropyl group, a phenyl group, and a phenylmethyl group or a tautomer, or a salt thereof, or a salt of a tautomer, or a mixture of same.

In other embodiments, $R^{22}$ is independently selected from a —$(CH_2)_2$-morpholino group, a —$(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, a phenylmethyl group or a tautomer, or a salt thereof, or a salt of a tautomer, or a mixture of same.

In other embodiments, $R^{22}$ is independently selected from a methyl group, an ethyl group, a hydroxyethyl group, a 2-hydroxy-2-methylpropyl group, a 3-hydroxy-3-methylbutyl group, a trifluoromethyl group, a methoxyethyl group, a 2-methoxy(methyl)amino group, a (dimethylamino)ethyl group, a —$(CH_2)_2$-morpholino group, a —$(CH_2)_3$-morpholino group, a (3,3-difluoropyrrolidin-1-yl)ethyl group, a (3,3-difluoroazetidin-1-yl)ethyl group, a 3-fluoroazetidin-1-yl)ethyl group, a 2-(oxan-4-yl)ethyl group, a (4-methylpiperazin-1-yl)ethyl group, a cyclopropyl group, a phenyl group, a phenylmethyl group and $R^{23}$ is hydrogen or a tautomer, or a salt thereof, or a salt of a tautomer, or a mixture of same.

In other embodiments, $R^{22}$ is a —$(CH_2)_2$-morpholino group or a tautomer, or a salt thereof, or a salt of a tautomer, or a mixture of same.

In other embodiments, $R^{22}$ is a —$(CH_2)_2$-morpholin-4-yl group or a tautomer, or a salt thereof, or a salt of a tautomer, or a mixture of same.

In other embodiments, $R^{22}$ is independently selected from a methyl group, an ethyl group, a hydroxyethyl group, a —$(CH_2)_2$-morpholino group, trifluoromethyl group and a cyclopropyl group; or a tautomer, or a salt thereof, or a salt of a tautomer, or a mixture of same.

In yet further embodiments, $R^{23}$ is a hydrogen atom, a salt thereof or a salt of a tautomer or a salt of an N-oxide or a mixture of same.

In further embodiments, the present invention includes compounds of formula (I), or a tautomer, an N-oxide, or a salt thereof or a salt of a tautomer or a salt of an N-oxide or a mixture of same.

In further embodiments, the present invention includes compounds of formula (I), or a tautomer, or a salt thereof, or a salt of a tautomer, or a mixture of same.

In yet further embodiments, the present invention includes compounds of formula (I), or a salt thereof or a mixture of same.

In further embodiments, the compounds are salts.

In further embodiments, the compounds are amine salts or salts with organic acids.

In further embodiments, the compounds are a tautomer, or a salt thereof or a salt of a tautomer or a mixture of same.

In further embodiments, the compounds are an N-oxide, or a salt thereof or a salt of an N-oxide or a mixture of same.

In further embodiments of the first aspect, the present invention provides combinations of two or more of the above mentioned embodiments under the heading "further embodiments of the first aspect of the present invention".

Furthermore it is understood that the invention includes any subcombination of the disclosed single embodiments herein for certain residues or combined with a subcombination of residues as outlined in the claims.

The present invention includes any sub-combination within any embodiments or aspects of the present invention supra.

The present invention includes any sub-combination within any embodiments or aspects of the present invention of compounds or intermediate compounds of general formula (I) or (II). The present invention includes corresponding methods relating to the compounds of general formula (I) which are disclosed in the Example Section of this text, infra.

Synthesis of compounds of formula (I) have been developed that require a two-step process for macrocyclization of the compound of formula (II). For example, intermediate A can be cyclized to provide intermediate C by first treating intermediate A with (2Z)-1,4-dichlorobut-2-ene for an extended period of time to afford macrocycle B and then hydrogenating the double bond using tris(triphenylphosphine) rhodium (I) chloride in a hydrogen atmosphere to produce compound C.

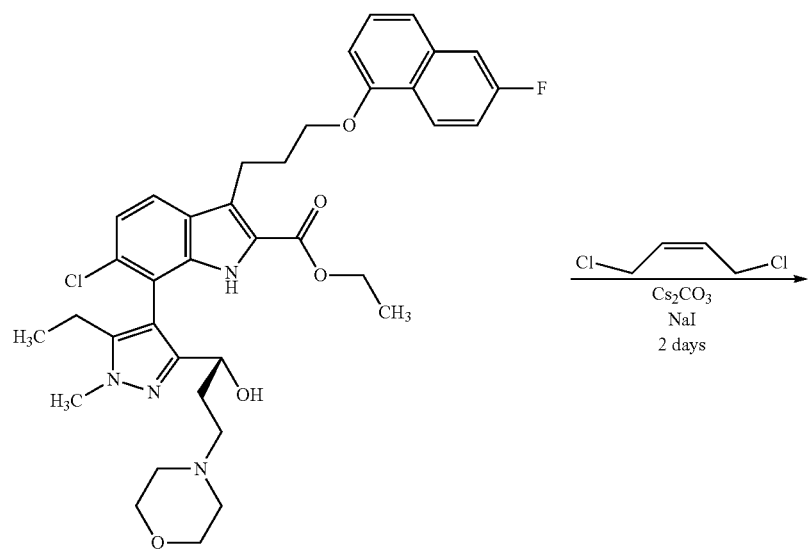

A

-continued
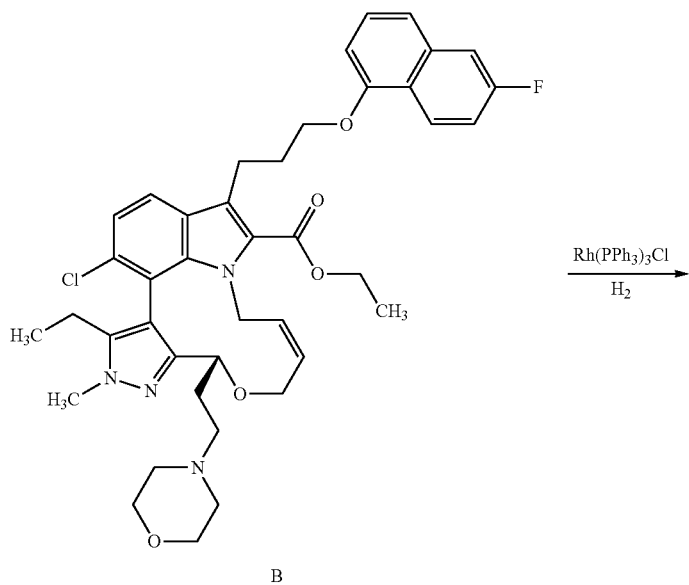
B
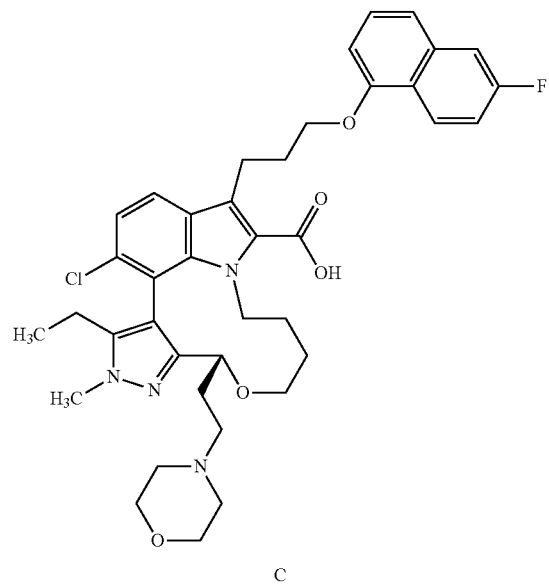 [SMILES: CCOC(=O)c1c(CCCOc2cccc3cc(F)ccc23)c2ccc(Cl)c3c2n1CCCCO[C@@H](CCN1CCOCC1)c1nn(C)c(CC)c1-3]
C
The reactivity of the chloroalkene coupled with the toxicity of the hydrogenation agent result in moderate yields of compounds of formula (I), such as compound C. Higher yields and greater time efficiency have been achieved in the disclosed methods that in one synthetic reaction transform intermediate A to compound C.

In some embodiments, a compound of formula (II):

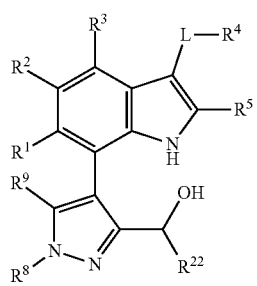

(II)

is contacted with a di-functionalized alkane

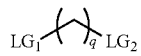

wherein
variables $R^1$, $R^2$, $R^3$, $R^4$, $R^8$, $R^9$, and $R^{22}$ are as defined above,
$R^5$ is —$CO_2(C_{1-6}alkyl)$ and
$LG^1$ and $LG^2$ are each independently selected from halo or sulfonate.

In some embodiments, $R^5$ is selected from a COO ($C_{1-6}$alkyl) group, such as $CO_2Me$ and $CO_2Et$, preferably $CO_2Et$. In some embodiments, when $R^5$ is a $COO(C_{1-6}alkyl)$ group, the reaction of the compound of formula (II) with the di-functionalized alkane is followed by contacting the resulting compound of formula (I) with a base, such as an inorganic base selected from LiOH, NaOH, KOH, $Mg(OH)_2$, $Li_2CO_3$, $Na_2CO_3$, $K_2CO_3$, $MgCO_3$, preferably LiOH. The solvent can be selected from ethers such as such as tetrahydrofuran (THF), methyltetrahydrofuran (preferably 2-methyltetrahydrofuran), 1,4-dioxane, cyclopropyl methyl ether, tert-butyl methyl ether, 1,2-dimethoxyethane, and bis-(2-methoxymethyl) ether; alcohols such as methanol, ethanol, n-propanol, isopropanol, n-butanol, 1,1,1-trifluoroethanol, n-amylalcohol, and 1-methoxy-2-propanol; and water, or any combinations thereof. In some embodiments, the solvent system for the hydrolysis reaction comprises THF, EtOH and water. The product of this hydrolysis reaction is a compound of formula (I) where $R^5$ is COOH.

$LG^1$ and $LG^2$ are leaving groups and can be the same or different. $LG^1$ and $LG^2$ can be selected from halo, such as chloro, bromo, or iodo, or a sulfonate, such as methanesulfonyl, trifluoromethylsulfonyl, toluenesulfonyl and nitrobenzenesulfonyl. In certain embodiments, $LG^1$ and $LG^2$ are each bromo. One of ordinary skill would be familiar with leaving groups known in the art and select an appropriate leaving group(s).

The disclosed one-step reaction is performed in a solvent, such as halogenated solvents. Exemplary solvents include, but are not limited to, halogenated solvents such as dichloromethane, trichloromethane, tetrachloromethane, 1,2-dichloroethane, 1,1,1-trichloroethane, 1,1,2-trichloroethane; and aliphatic and aromatic solvents, e.g. cyclohexane, methylcyclohexane, heptane, hexane, toluene, trifluoromethylbenzene, 4-chloro-trifluoromethylbenzene, chlorobenzene, 1,2-dichlorobenzene, 1,3-dichlorobenzene, and nitrobenzene. Other exemplary solvents include ethers such as tetrahydrofuran, methyltetrahydrofuran (preferably 2-methyltetrahydrofuran), 1,4-dioxane, cyclopropyl methyl ether, tert-butyl methyl ether, 1,2-dimethoxyethane, and bis-(2-methoxymethyl) ether. Further solvents can include nitriles such as acetonitrile, propionitrile, and butyronitrile; amides such as dimethylformamide (DMF) and N-methylpyridione (NMP); alcohols such as methanol, ethanol, n-propanol, isopropanol, n-butanol, 1,1,1-trifluoroethanol, n-amylalcohol, and 1-methoxy-2-propanol; ketones such as acetone and ethyl methyl ketone (MEK), and other polar solvents such as sulfolane, water, and any combination thereof. In preferred embodiments, the solvent comprises acetonitrile. In some embodiments, phase transfer catalysis conditions can be used such as tetrabutylammonium bromide, tetraoctylammoniumbromide, or triethylbenzylammonium chloride.

The disclosed macrocyclization is performed in the presence of a base. Preferred bases include, but are not limited to, alkali metal or alkaline earth metal acetates, phosphates, amides, carbonates, hydrogencarbonates, hydrides, hydroxides and alkoxides. Exemplary bases include, but are not limited to, sodium acetate, potassium acetate or calcium acetate, potassium phosphate, lithium amide, sodium amide, potassium amide or calcium amide, lithium carbonate, sodium carbonate, potassium carbonate, cesium carbonate or calcium carbonate, sodium hydrogencarbonate, potassium hydrogencarbonate or calcium hydrogencarbonate, lithium hydroxide, sodium hydroxide, potassium hydroxide, cesium hydroxide, or calcium hydride, n-butyllithium, sec-butyllithium, tert-butyllithium, lithium diisopropylamide, lithium or potassium bis(trimethylsilyl)amide, sodium methoxide, ethoxide, n- or i-propoxide, n-, i-, s- or t-butoxide, or potassium methoxide, ethoxide, n- or i-propoxide, n-, i-, s- or t-butoxide; and also basic organic nitrogen compounds, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN), diazabicyclo[5.4.0]-undec-7-ene (DBU), phosphazene bases such as N'''-tert-butyl-N,N',N''-tris[tris(dimethylamino)-lambda5-phosphanylidene]phosphorimidic triamide, fluorides, e.g., potassium fluoride, oxides, e.g, silver (II) oxide or any combination thereof. A preferred base is cesium carbonate.

In some embodiments, an additive is present in the reaction of the compound of formula (II) with the di-functionalized alkane. In certain embodiments, the additive is selected from an iodide source, such as sodium iodide, potassium iodide, and tetrabutylammonium iodide (TBAI). In preferred embodiments, an additive is not present in this reaction. Optionally, a phase transfer catalyst is present, such as tetrabutylammonium bromide, tetraoctylammoniumbromide, and triethylbenzylammonium chloride.

In some embodiments, the reaction of the compound of formula (II) with the di-functionalized alkane is performed at a concentration of the compound of formula (II) in the range of 1 µM to 2 M, preferably in the range of 0.01 M to 0.09 M. The amount of the di-functionalized alkane can be in the range from 0.5 to 5 molar equivalents, preferably in the range of 1.0 to 1.5 molar equivalents.

In some embodiments, the reaction of the compound of formula (II) with the di-functionalized alkane is preferably conducted in a single process in which the indole nitrogen and the hydroxyl groups of the compound of formula (II) are both alkylated with the di-functionalized alkane. In other embodiments, the indole nitrogen can be alkylated first and the intermediate isolated by purification of the resulting reaction mixture by known techniques, for example precipitation, recrystallization or chromatography. The ring closure at the hydroxyl group is carried out as a second step.

In some embodiments, the reaction of the compound of formula (II) with the di-functionalized alkane is performed at a temperature from about −10° C. to about 200° C. and a pressure of from about 0.5 to about 2 bar. In certain embodiments, the compound of formula (II) and the base are added to the reaction vessel, followed by the di-functionalized alkane. In some embodiments, the di-functionalized alkane is added at a low temperature, such as at about 0° C. to about 20° C. Then, the reaction can be warmed to about 30° C. to about 150° C. for about 2 h to about 24 h, preferably about 50° C. to about 100° C.

Upon completion of the reaction, the reaction mixture can be diluted by addition of an organic solvent, preferably ethyl acetate, and the combined organic phases can be washed, preferably with water, dried, preferably over magnesium sulfate, and filtered. The product obtained by evaporation of the organic solvent and other volatile components, preferably under reduced pressure, can be purified by known techniques, for example precipitation, recrystallization or chromatography. Preferably, flash chromatography is applied using consecutively silica gel and amino bonded silica gel as stationary phase to afford the compound of formula (I).

Experimental Section

Experimental Section—NMR Spectra

To the extent NMR peak forms and multiplicities are specified, they are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_i$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Experimental Section—Abbreviations

The following table lists the abbreviations used in this paragraph and in the Intermediates and Examples section as far as they are not explained within the text body. Other abbreviations have their meanings customary per se to the skilled person. A comprehensive list of the abbreviations utilized by organic chemists of ordinary skill in the art appears presented in the first issue of each volume of the Journal of Organic Chemistry; this list is typically presented in a table titled "Standard List of Abbreviations". In case of doubt, the abbreviations and/or their meaning according to the following table shall prevail.

TABLE 1

Abbreviations

| Abbreviation | Meaning |
|---|---|
| br. | broad signal (NMR) |
| BPR | Back Pressure Regulator |
| d | doublet (NMR) |
| DAD | Diode array detector |
| dd | doublet of doublet (NMR) |
| dt | doublet of triplet (NMR) |
| DMF | N,N-Dimethylformamide |
| DMSO | dimethylsulfoxide |
| EDC | N-[3-(dimethylamino)propyl]-N'-ethylcarbodiimide hydrochloride |
| EDTA | ethylenediaminetetraacetic acid |
| ee | enantiomeric excess |
| ESI | electrospray (ES) ionisation |
| h, hr (hours) | hour(s) |
| HCl | hydrogen chloride, hydrochloric acid |
| HMBC | heteronuclear multiple bond correlation |
| HOBt | Benzotriazol-1-ol |
| HPLC | high performance liquid chromatography |
| HRP | horseradish peroxidase |
| HSQC | Heteronuclear Single Quantum Coherence |
| LC-MS | liquid chromatography-mass spectrometry |
| m | multiplet (NMR) |
| Min | minute(s) |
| MS | mass spectrometry |
| MTP | microtiter plate |
| MWD | Multiple wavelength detector |
| Na—K-tartrate | Sodium potassium tartrate |
| NHS | N-hydroxysuccinimide |
| NMR | nuclear magnetic resonance spectroscopy: chemical shifts (δ) are given in ppm. The chemical shifts were corrected by setting the DMSO signal to 2.50 ppm using dmso-d6 unless otherwise stated. |
| NAD$^+$ | nicotinamide adenine dinucleotide |
| PBS | phosphate buffered saline |
| Pd(dppf)Cl$_2$x CH$_2$Cl$_2$ | [1,1'-Bis-(diphenylphosphino)-ferrocen]-dichloropalladium(II), complex with dichloromethane |
| q | quartet (NMR) |
| quin | quintet (NMR) |
| R$_f$ | Retardation factor in thin layer chromatography |
| rt, RT | room temperature |
| R$_t$, Rt | retention time |
| RuPhos Pd G3 | (2'-aminobiphenyl-2-yl)(methanesulfonato-kappaO)palladium-[2',6'-bis(propan-2-yloxy)biphenyl-2-yl](dicyclohexyl)phosphane (1:1) |

TABLE 1-continued

Abbreviations

| Abbreviation | Meaning |
|---|---|
| | (Cas No: 1445085-77-7) |
| s | singulet (NMR) |
| SFC | Supercritical Fluid Chromatography |
| SPA | Scintillation proximity assay |
| t | triplet (NMR) |
| td | triplet of doublet (NMR) |
| TFA | trifluoroacetic acid |
| THF | tetrahydrofuran |
| DCM | dichloromethane |
| EA | ethyl acetate |
| PE | petroleum ether |
| MTBE | methyl tert-butyl ether |
| DMF | dimethyl formamide |
| TLC | thin layer chromatography |
| UPLC | ultra performance liquid chromatography |
| UV | ultraviolet |
| wt-% | percent of weight |
| [$^3$H]- | tritium |
| δ | chemical shift |
| XPhos Pd G2 | Chloro(2-dicyclohexylphosphino-2',4',6'-triisopropyl-1,1'-biphenyl)[2-(2'-amino-1,1'-biphenyl)]palladium(II) (Cas No: 1310584-14-5) |
| XPhos Pd G3 | (2-Dicyclohexylphosphino-2',4',6''-triisopropyl-1,1'-biphenyl)[2-(2'-amino-1,1'-biphenyl)]palladium(II) methanesulfonate (Cas No: 1445085-55-1) |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. Reactions were set up and started, e.g. by the addition of reagents, at temperatures as specified in the protocols; if no temperature is specified, the respective working step was performed at ambient temperature, i.e. between 18 and 25° C.

"Silicone filter" or "water resistant filter" refers to filter papers which are made hydrophobic (impermeable to water) by impregnation with a silicone. With the aid of these filters, water can be separated from water-immiscible organic solvents by means of a filtration (i.e. filter paper type MN 617 WA, Macherey-Nagel).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent or solvent mixture. In some cases, the compounds may be purified by chromatography, preferably flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or dichloromethane/ethanol. In flash column chromatography, unmodified ("regular") silica gel may be used as well as aminophase functionalized silica gel. As used herein, "Biotage SNAP cartridge silica" refers to the use of regular silica gel; "Biotage SNAP cartridge NH$_2$ silica" refers to the use of aminophase functionalized silica gel. If reference is made to flash column chromatography or to flash chromatography in the experimental section without specification of a stationary phase, regular silica gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid, diethylamine or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Exemplary LC-MS or HPLC Methods

Method 1:

LCMS instrument type: Agilent 1200\G6110A; column: Kinetex@ 5 um EVO C18 30*2.1 mm; mobile phase A: 0.0375% TFA in water (V/V), B: 0.0188% TFA in Acetonitrile (V/V); gradient: 0.01 min 5% B→0.8 min 95% B→1.2 min 95% B→1.21 min 95% B→1.5 min 5% B; flow rate: 1.5 mL/min; Column temperature: 50° C.; UV detection: 220 nm & 254 nm.

Method 2:

LCMS instrument type: SHIMADZU LCMS-2020; column: Kinetex EVO C18 2.1×30 mm, 5 um; mobile phase A: 0.0375% TFA in water (v/v), B: 0.01875% TFA in Acetonitrile (v/v); gradient: 0.00 min 5% B→0.8 min 95% B→1.2 min 95% B→1.21 min 5% B→1.5 min 5% B; flow rate: 1.5 mL/min; Column temperature: 50° C.; UV detection: 220 nm & 254 nm.

Method 3:

LCMS instrument type: Agilent 1200\G6110A; column: XBridge C18 2.1*50 mm, 5 um; mobile phase A: 0.025% NH$_3$·H$_2$O in water (v/v, B: Acetonitrile; gradient: 0.00 min 10% B→1.20 min 80% B→1.60 min 80% B→1.60 min 80% B→1.61 min 10% B→2.00 min 10% B; flow rate: 1.2 mL/min; Column temperature: 40° C.; UV detection: 220 nm & 254 nm.

Method 4:

HPLC instrument type: SHIMADZU LC-20AB; column: Kinetex C18 4.6*50 mm*5 um; mobile phase A: 0.0375% TFA in water (v/v), B: 0.01875% TFA in Acetonitrile (v/v); gradient: 0.00 min 10% B→2.40 min 80% B→3.70 min 80% B→3.71 min 10% B→4.00 min 10% B; flow rate: 1.5 mL/min; Column temperature: 50° C.; UV detection: PDA (220 nm&215 nm&254 nm).

Method 5:
LCMS instrument type: SHIMADZU LCMS-2020; column: Kinetex EVO C18 2.1×30 mm, 5 um; mobile phase A: 0.0375% TFA in water (v/v), B: 0.01875% TFA in Acetonitrile (v/v); gradient: 0.00 min 50% B→0.8 min 100% B→1.2 min 100% B→1.21 min 50% B→1.5 min 50% B; flow rate: 1.5 mL/min; Column temperature: 50° C.; UV detection: 220 nm & 254 nm.

Method 6:
HPLC instrument type: SHIMADZU LC-20AB; column: Kinetex C18 4.6*50 mm*5 um; mobile phase A: 0.0375% TFA in water (v/v), B: 0.01875% TFA in Acetonitrile (v/v); gradient: 0.00 min 50% B→2.40 min 100% B→3.70 min 100% B→3.71 min 50% B→4.00 min 50% B; flow rate: 1.5 mL/min; Column Temperature: 50° C.; UV detection: PDA (220 nm&215 nm&254 nm).

Method 7:
HPLC instrument type: SHIMADZU LC-20AB; column: Kinetex C18 4.6*50 mm*5 um; mobile phase A: 0.0375% TFA in water (v/v), B: 0.01875% TFA in Acetonitrile (v/v); gradient: 0.00 min 10% B→4.20 min 80% B→5.30 min 80% B→5.31 min 10% B→6.00 min 10% B; flow rate: 1.5 mL/min; Column temperature: 50° C.; UV detection: PDA (220 nm&215 nm&254 nm).

Method 8:
LCMS instrument type: SHIMADZU LCMS-2020; column: Kinetex EVO C18 2.1×30 mm, 5 um; mobile phase A: 0.0375% TFA in water (v/v), B: 0.01875% TFA in Acetonitrile (v/v); gradient: 0.00 min 5% B→3.00 min 95% B→3.50 min 95% B→3.51 min 5% B→4.00 min 5% B; flow rate: 0.8 mL/min; Column temperature: 50° C.; UV detection: 220 nm & 254 nm.

Method 9:
HPLC instrument type: SHIMADZU LC-20AB; column: Kinetex C18 2.1*50 mm*5 um; mobile phase A: 0.025% $NH_3·H_2O$ in water (v/v), B: Acetonitrile (v/v); gradient: 0.00 min 10% B→2.40 min 80% B→3.20 min 80% B→3.31 min 10% B→4.00 min 10% B; flow rate: 0.8 mL/min; Column temperature: 40° C.; UV detection: PDA (220 nm&215 nm&254 nm).

Method 10:
HPLC instrument type: SHIMADZU LC-2020; column: Kinetex C18 2.1*30 mm*5 um; mobile phase A: 0.025% $NH_3·H_2O$ in water (v/v), B: Acetonitrile (v/v); gradient: 0.00 min 5% B→0.80 min 95% B→1.20 min 80% B→1.21 min 5% B→1.55 min 5% B; flow rate: 1.5 mL/min; Column temperature: 40° C.; UV detection: PDA (220 nm&254 nm).

General Scheme 1

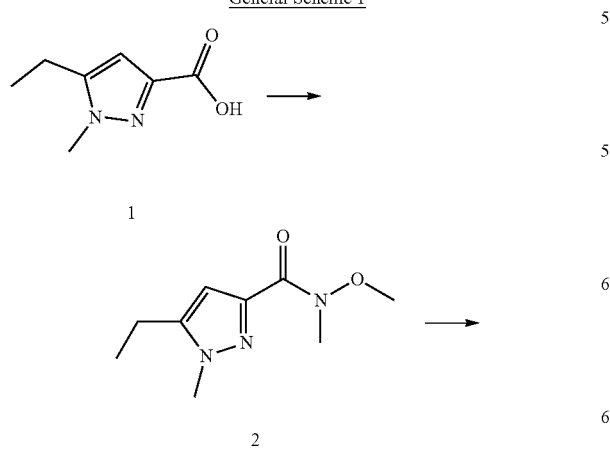

General Scheme 2

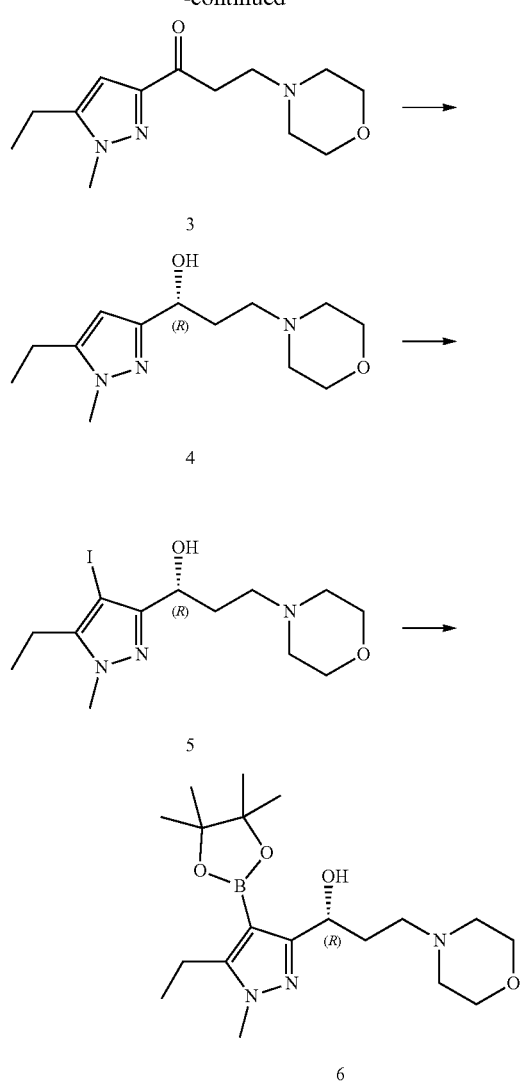

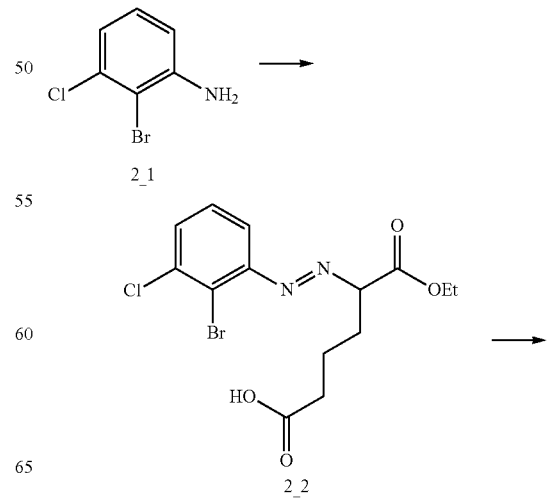

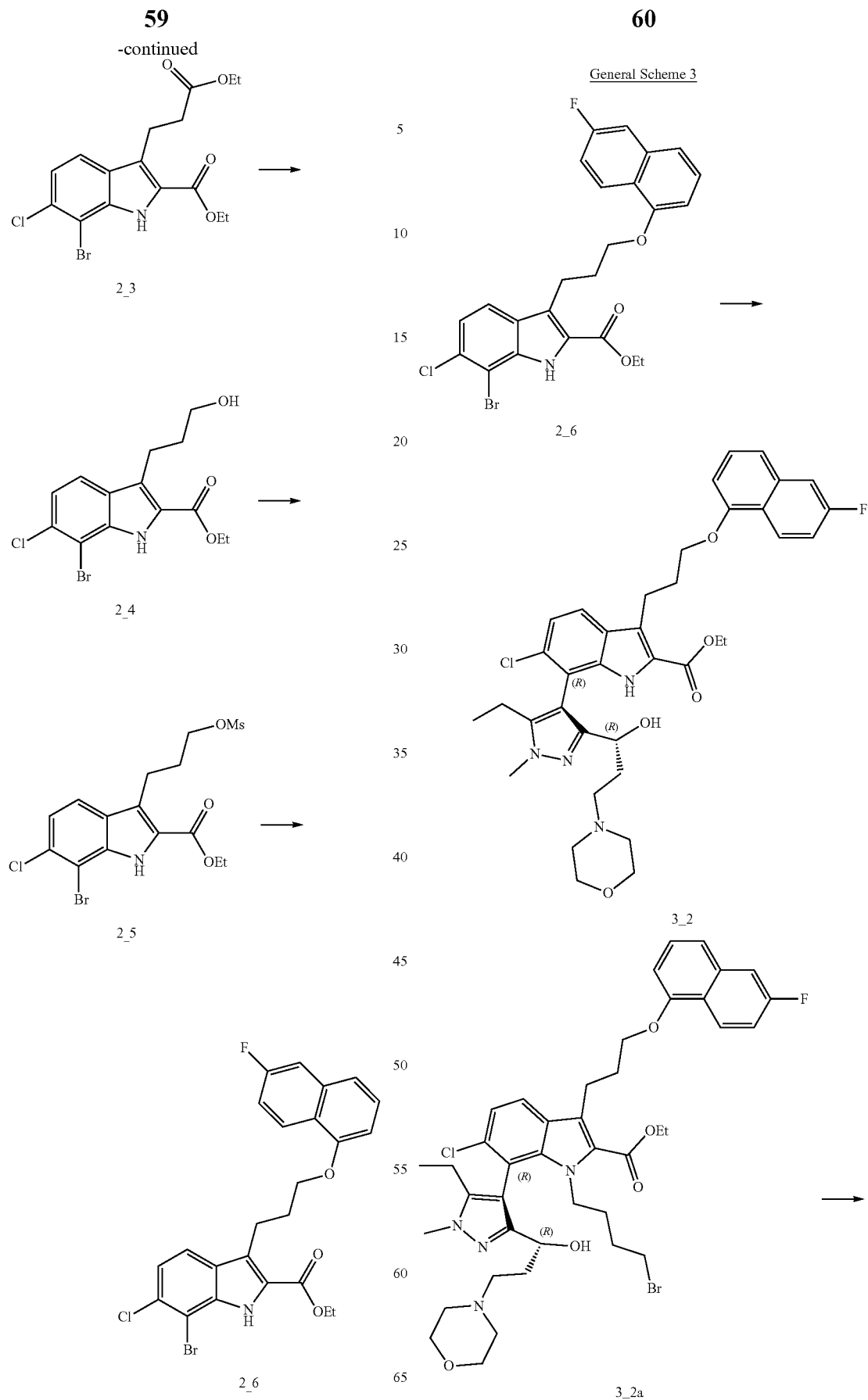

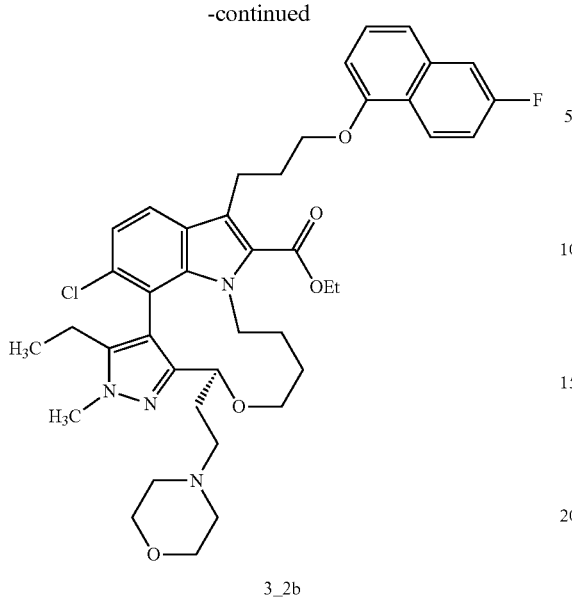

3_2b

Example 1

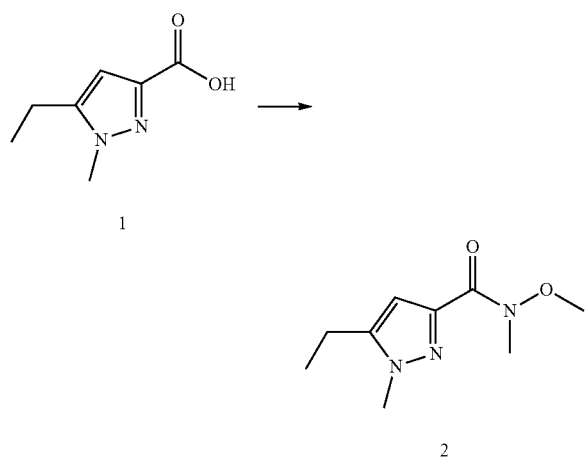

The reactions were performed as two batches in parallel:

To a solution of Compound 1 (2.00 Kg, 12.97 mol) in DCM (20.0 L) was added DMF (284 g, 3.89 mol) with stirring, then oxalyl dichloride (2.64 kg, 20.79 mol) was added to the mixture at 15-25° C. over 2 hrs under $N_2$. Then the mixture was stirred at 15-25° C. for another 1 hr. $Et_3N$ (3.97 kg, 39.28 mol) was added into the mixture at 15~25° C. for 2 hrs. After the addition, N-methoxymethanamine; hydrochloride (1.33 kg, 13.62 mol) was added to the mixture, and the mixture was stirred at 25° C. for 12 hrs. TLC (PE/EA=1/1) indicated the reaction was completed. The combined reaction mixture (2 batches) was diluted with water (40 L). Then the solution was partitioned. The organic phase was collected and the aqueous phase was extracted with DCM (10 L×2). The combined organic layer was washed with brine (10 L×2), dried over $Na_2SO_4$, filtered, the filtrate was concentrated to give the residue of Compound 2 (4.00 kg, 20.28 mol, 78.16% yield) as a brown oil.

$^1$H NMR: 400 MHZ CDCl$_3$

δ 6.49 (s, 1H), 3.79 (s, 3H), 3.72 (s, 3H), 3.39 (s, 3H), 2.61-2.55 (q, J=7.6 Hz, 2H), 1.26-1.22 (t, J=7.6 Hz, 3H)

Example 2

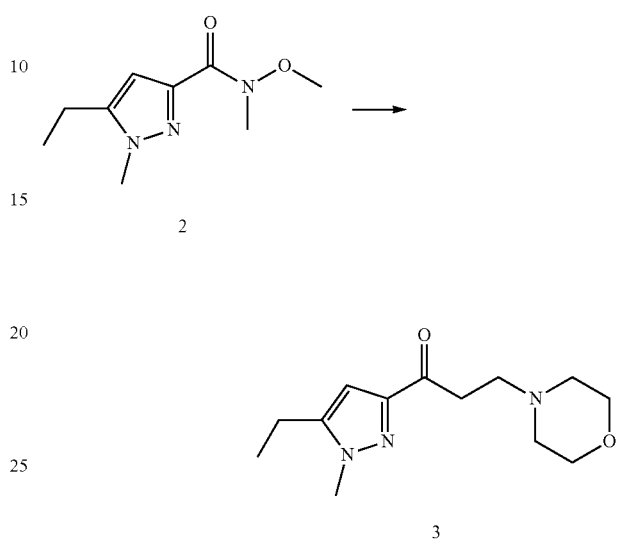

To a solution of Compound 2 (1.80 Kg, 9.13 mol, 1 eq) in THF (9.00 L) at 0° C. was added chloro(vinyl)magnesium (2 Min THF, 8.40 L) within 2 hrs. After addition, the reaction mixture was allowed to stir at ambient temperature (28° C.) for 2.5 hrs. Then to the mixture was added morpholine (2.39 kg, 27.41 mol) and followed by $H_2O$ (3.15 L) at 28-40° C. in one portion, the mixture was stirred at 28° C. for another 0.5 hr. TLC (PE/EA=1/1) showed the reaction was completed. The combined reaction mixture (2 batches) was diluted with water (6.0 L). Then the solution was partitioned, the organic phase was collected and the aqueous phase was extracted with EA (2000 mL×2). The combined organic layer was washed with brine (3.0 L×2), dried over $Na_2SO_4$, filtered, the filtrate was concentrated to give the Compound 3 (3.3 kg, 13.13 mol, 71.94% yield) as a brown oil.

$^1$H NMR: 400 MHz CDCl$_3$

δ 6.52 (s, 1H), 3.79 (s, 3H), 3.66-3.64 (t, J=5.8 Hz, 4H), 3.15-3.11 (t, J=7.6 Hz, 2H), 2.79-2.76 (t, J=6.8 Hz, 2H), 2.61-2.55 (q, J=7.6 Hz, 2H), 2.48-2.45 (m, J=4.4 Hz, 4H), 1.26-1.23 (t, J=8.2 Hz, 3H)

LC-MS: (Method 1), RT=0.772 min, MS+1=252.2

Example 3

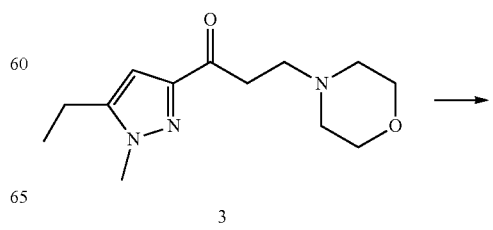

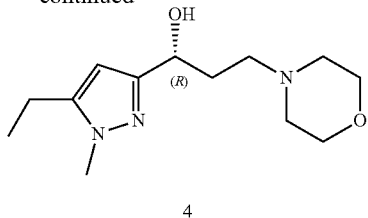

4

To a solution of Compound 3 (587 g, 2.34 mol, 1 eq) in DCM (3250 mL) was added TEA (472.71 g, 4.67 mol), HCOOH (448.47 g, 9.34 mol) −0-5° C., and [[(1R,2R)-2-amino-1,2-diphenyl-ethyl]-(p-tolylsulfonyl)amino]-chloro-ruthenium; 1-isopropyl-4-methyl-benzene (29.72 g, 46.71 mmol) with stirring at −0~5° C. The mixture was stirred for 70 hrs at 25° C. under $N_2$. (LCMS: detected major 4 formed.) The combined reaction mixture (8 batches) was concentrated by evaporator under reduced pressure at 40° C. The residue was dissolved in 10.0 L of water. The resulting mixture was filtered and the filtrate was washed with MTBE (4.0 L×3). The water phase was adjusted pH=~11 with 2M aq. sat. NaOH. Then the resulting mixture was extracted with DCM (4.0 L×3). The combined organic phase was concentrated by evaporator under reduced pressure to afford Compound 4 (3.2 Kg, 12.63 mol, 67.60% yield) as a black brown oil (SFC: Column: Chiralpak AD-3 50×4.6 mm I.D., 3 um; Mobile phase: Phase A for $CO_2$, and Phase B for MeOH (0.05% DEA); Gradient elution: B in A from 5% to 40%; Flow rate: 3 mL/min; Detector: DAD; Column Temp: 350° C.; Back Pressure: 100 Bar), which was used directed without further purification.

$^1$H NMR: 400 MHz $CDCl_3$
δ 5.99 (s, 1H), 4.89-4.86 (m, 1H), 3.71-3.64 (m, 7H), 2.69-2.66 (m, 4H), 2.57-2.51 (q, J=7.6 Hz, 2H), 2.50-2.44 (br, 2H), 1.99-1.88 (m, 2H), 1.23-1.20 (t, J=8.2 Hz, 3H)
LC-MS: (Method 1), RT=0.753 min, MS+1=254.1
HPLC: (Method 9), RT=1.346 min
SFC: Peak 1=0.991 min Peak 2=1.126 min, EE=91.9%

Example 4

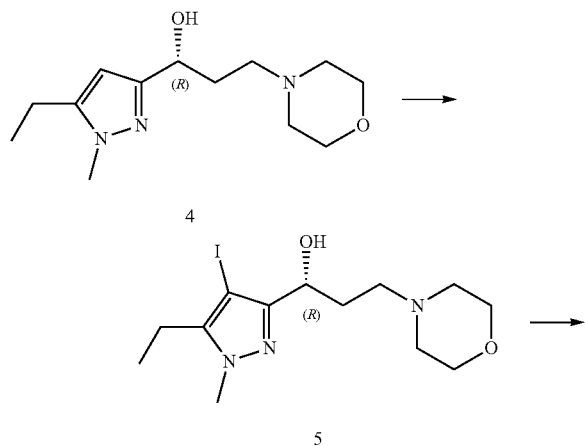

To a solution of Compound 4 (3.20 g, 12.63 mol) in DCM (20 L) was added to TFA (2.88 kg, 25.26 mol) at −5° C. to 0° C., then NIS (3.27 kg, 14.53 mol) was added to the mixture in small portions at 0° C. The solution was then stirred at 0° C. for 1.5 hrs. TLC (DCM/MeOH=15/1) indicated the reaction was complete. The reaction mixture was extracted with $H_2O$ (3.0 L×6) and the combined water phase was adjusted with solid $K_2CO_3$ until pH reached 9-10. Then the resulting mixture was extracted with DCM (3.0 L×3), the combined organic layer was washed with brine (3.0 L×2), dried over $Na_2SO_4$, filtered, and concentrated by evaporator under reduced pressure to give Compound 5 (850 g, 2.24 mol, 69.25% yield) as a yellow oil (SFC: Column: Chiralpak IC-3 50×4.6 mm I.D., 3 um; Mobile phase: Phase A for $CO_2$, and Phase B for MeOH (0.05% DEA); Gradient elution: B in A from 5% to 40%; Flow rate: 3 mL/min; Detector: DAD; Column Temp: 35° C.; Back Pressure: 100 Bar).

$^1$H NMR: 400 MHz $CDCl_3$
δ4.89-4.86 (dd, 1H), 3.80 (s, 3H), 3.70-3.67 (m, 4H), 2.68-2.64 (m, 6H), 2.44 (brs, 2H), 2.15-2.06 (m, 1H), 1.82-1.75 (m, 1H), 1.11-1.08 (t, J=7.6 Hz, 3H).
LC-MS: (Method 1), RT=0.784 min, MS+1=380.1
HPLC: (Method 6), RT=1.093 min
SFC: Peak 1=1.835 min, Peak 2=2.076 min, EE=97.1%

Example 5

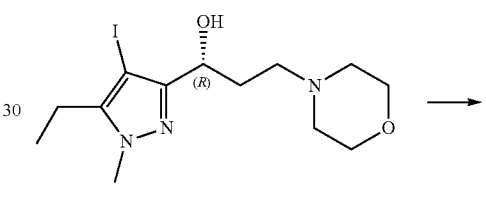

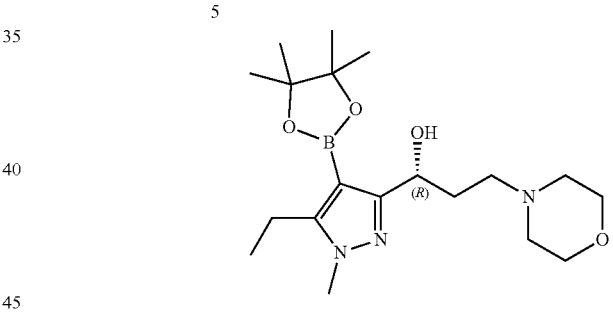

To a solution of Compound 5 (1.75 Kg, 4.61 mol) in THF (8.75 L) was added 2-isopropoxy-4,4,5,5-tetramethyl-1,3,2-dioxaborolane (2.58 kg, 13.84 mol,) at 28° C., then to the mixture was added i-PrMgCl (2 M in THF, 10.50 L) at −5-0° C. under $N_2$ for 3 hrs. The mixture was stirred for 2 hrs at 28° C. under $N_2$. LC-MS indicated the reaction was complete. The combined reaction mixture (2 batches) was poured into $NH_4Cl$ (30 L) and the mixture was extracted with EA (6 L×4). The combined organic layer was washed with brine (1 L×3), dried over $Na_2SO_4$, filtered, and concentrated by evaporator under reduced pressure to give Compound 6 (3.2 kg, crude used directly) as a brown oil.

$^1$H NMR: 400 MHz $CDCl_3$
δ 4.91-4.88 (m, 1H), 3.73-3.69 (m, 7H), 2.82-2.79 (m, 2H), 2.63-2.52 (m, 2H), 2.51-2.43 (m, 4H), 1.97-1.93 (m, 2H), 1.29 (s, 12H), 1.14-1.10 (t, J=7.6 Hz, 3H).
LC-MS: (Method 1), RT=0.946 min, MS+1=380.3
LC-MS: (Method 10), RT=0.923 min, MS+1=380.3
HPLC: (Method 9), RT=2.160 min

Example 6

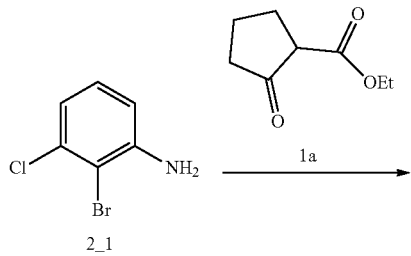

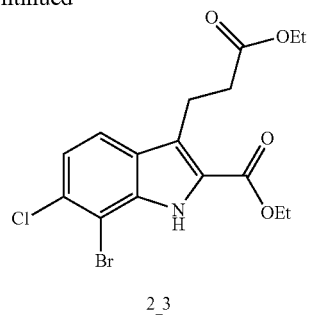

To a solution of Compound 2_1 (1.80 kg, 8.72 mol) in aq. HCl (1.60 M, 16.4 L) was added NaNO$_2$ (2.5 M, 3.49 L) in portions at 0~5° C. under N$_2$. After stirred at 0° C. for 30 min, aq. NaOAc (4.5 M, 10.9 L) and 1a (1.36 kg, 8.72 mol, 1.30 L) were added to the mixture, then the mixture was stirred at 0° C. for another 1 hr. PLC indicated Compound 2_1 was consumed. The mixture was extracted with EA (15.0 L), the combined organic phases (2 batches) was washed with brine (5.00 L), then concentrated in vacuum to give the Compound 2_2 (14.4 kg, crude) as a brown oil, which was used to next step without further purification.

HPLC: (method 4) product: RT=2.442 min

Example 7

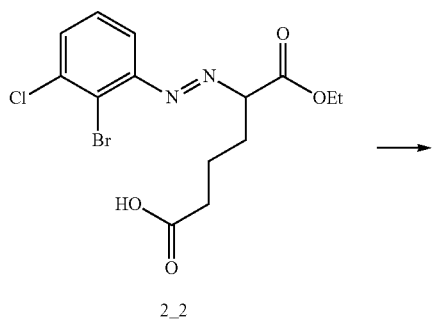

To a solution of Compound 2_2 (6.82 kg, 17.4 mol, 1.00 eq) in EtOH (15.6 L) was added conc. H$_2$SO$_4$ (7.58 L, 98% purity) drop-wise at 20-75° C. over 1 hr, Then the mixture was stirred at reflux for 18 hrs. HPLC indicated Compound 2_2 was consumed. The mixture was cooled to 50° C. and added to ice-water (40.0 L) drop-wise with black precipitates formed. The reaction mixture was stirred at 10° C. for 2 hrs and the precipitates were filtered and washed with water (2.00 L) to give a crude product. The crude was combined and purified by column chromatography (SiO$_2$, PE/DCM=3/1 to 1/1) to afford a crude product, which was triturated with PE/EA (30 L/3 L) at 20° C. for 10 hr to afford Compound 2_3 (6.50 kg, 15.6 mol, 96.4% purity) as a black solid.

1HNMR: (400 MHZ,CDCl$_3$)
δ=8.85 (br s, 1H), 7.61 (d, J=8.8 Hz, 1H), 7.22 (d, J=8.8 Hz, 1H), 4.45 (q, J=7.2 Hz, 2H), 4.09 (q, J=7.2 Hz, 2H), 3.36 (t, J=7.6 Hz, 2H), 2.67 (t, J=7.6 Hz, 2H), 1.45 (t, J=7.2 Hz, 3H), 1.20 (t, J=7.2 Hz, 3H)

LC-MS: (method 2) product: RT=1.073 min, MS+1=402.0

HPLC: (method 4) product: RT=2.580 min, (method 4) product: RT=2.552 min

Example 8

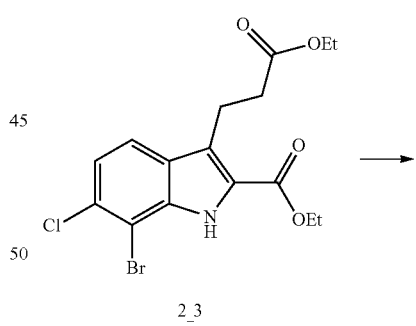

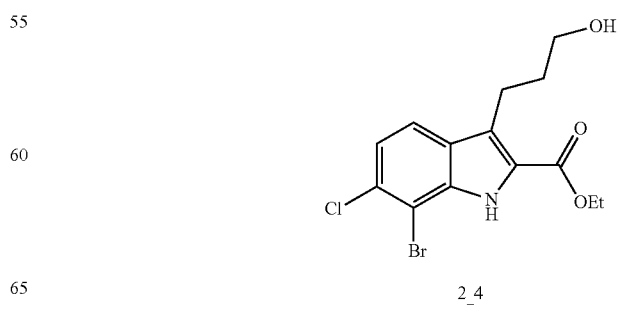

To a solution of Compound 2_3 (3.25 kg, 8.07 mol) in 2-methyltetrahydrofuran (15 L) was added BH3-Me2S (10.0M, 968 mL) by drop-wise at 50-60° while covered for 1 hr. The mixture was stirred at 55° C. for 18 hrs. HPLC showed Compound 2_3 (Rt=2.552 min) was consumed. The reaction mixture was quenched with MeOH (2.00 L) at 20-25° C. The reaction mixture was stirred at 20° C. for another 2 hrs. The two batches mixture was combined, then washed with water (10 L) and brine (6 L×2), and concentrated to give a residue. The residue was triturated with PE/EA (20 L/4 L) at 20° C. for 2 hrs to give Compound2_4 (4.62 kg, 11.5 mol, 71.3% yield) as an off-white solid.

$^1$HNMR: (400 MHZ,CDCl$_3$)

δ=8.77 (br s, 1H), 7.58 (d, J=8.8 Hz, 1H), 7.23 (d, J=8.8 Hz, 1H), 4.46 (q, J=7.2 Hz, 2H), 3.58 (t, J=6.0 Hz, 2H), 3.21 (t, J=7.2 Hz, 2H), 1.93 (dt, J=12.8, 6.6 Hz, 2H), 1.46 (t, J=7.2 Hz, 3H)

LC-MS: (method 2) product: RT=0.964 min, MS+1=361.9

HPLC: (method 4) product: RT=2.211 min, (method 4) product: RT=2.197 min

Example 9

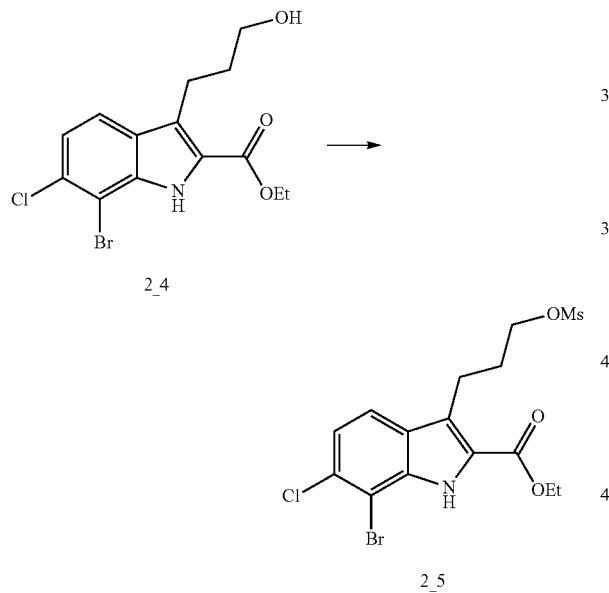

To a solution of Compound 2_4 (4.62 kg, 12.8 mol) and TEA (5.19 kg, 51.2 mol) in DCM (21.0 L) was added MsCl (3.30 kg, 28.83 mol) at 0-10° C. under N$_2$ over 1 hr. The mixture was stirred at 25° C. for 16 hrs. After an additional batch of TEA (1.30 kg, 12.8 mol) and MsCl (1.01 kg, 8.84 mol) were added, the mixture was stirred at 25° C. for another 1 hr. HPLC showed Compound 2_4 (Rt=2.197 min) was consumed. The mixture was washed with water (10.0 L) brine (10.0 L), and concentrated in vacuo to give the crude product. The crude product was triturated with PE/EA (25 L/5 L) at 20° C. for 1 hr. Compound 2_5 (4.86 kg, 8.37 mol, 65.4% yield) was obtained as a yellow solid.

$^1$HNMR: 400 MHZ, CDCl$_3$

δ=8.83 (br s, 1H), 7.56 (d, J=8.8 Hz, 1H), 7.25 (d, J=8.8 Hz, 1H), 4.46 (q, J=7.2 Hz, 2H), 4.25 (t, J=6.4 Hz, 2H), 3.21 (t, J=8.0 Hz, 2H), 3.00 (s, 3H), 2.09-2.23 (m, 2H), 1.46 (t, J=7.2 Hz, 3H)

LC-MS: (method 2) product: RT=1.006 min, MS+23=462.0

HPLC: (method 4) product: RT=2.647 min

HPLC: (method 4) product: RT=2.645 min

Example 10

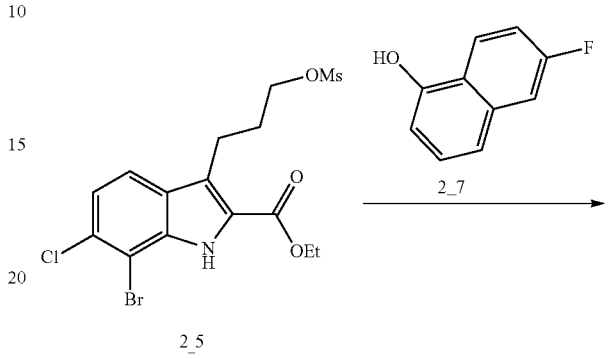

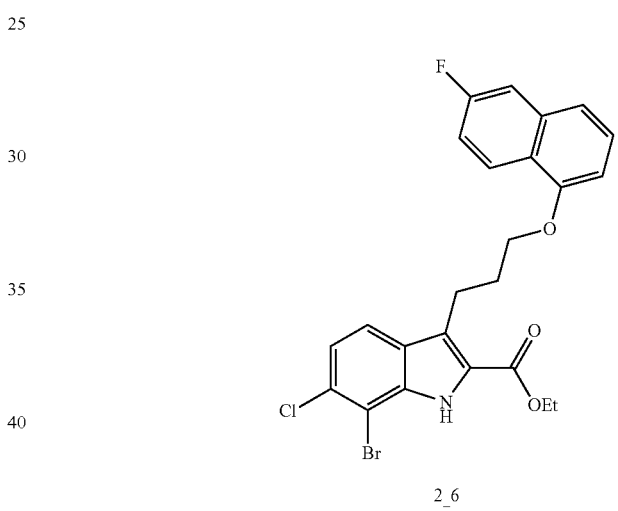

A mixture of Compound 2_5 (3.50 kg, 7.98 mol), Compound 2_7 (1.29 kg, 7.98 mol) and K$_2$CO$_3$ (2.21 kg, 15.96 mol) in MeCN (17.5 L) was stirred at 80° C. for 18 hrs. HPLC showed Compound 2_5 (Rt=2.645 min) was consumed. The reaction mixture was diluted with 2-methyltetrahydrofuran (30.0 L) and washed with brine (10.0 L). The organic layers were concentrated under reduced pressure to give a residue. The residue was triturated with EtOH (15.0 L) at 20° C. for 15 hrs. Compound 2_6 (3.10 kg, 5.56 mol, 61.2% yield, 90.6% purity) was obtained as a brown solid.

$^1$HNMR: 400 MHZ,CDCl$_3$

δ=8.81 (br s, 1H), 8.20 (dd, J=5.6, 9.2 Hz, 1H), 7.51 (d, J=8.8 Hz, 1H), 7.40 (dd, J=2.4, 10.0 Hz, 1H), 7.36-7.31 (m, 2H), 7.21 (dt, J=2.4, 8.8 Hz, 1H), 7.10 (d, J=8.4 Hz, 1H), 6.66 (dd, J=2.8, 5.6 Hz, 1H), 4.39 (q, J=7.2 Hz, 2H), 4.15 (t, J=6.0 Hz, 2H), 3.36 (t, J=7.2 Hz, 2H), 2.31 (quin, J=6.8 Hz, 2H), 1.39 (t, J=7.2 Hz, 3H)

LC-MS: (method 5) product: RT=0.721 min, MS+1=505.9

HPLC: (method 4) product: RT=3.150 min, (method 6) product: RT=1.888 min

Example 11

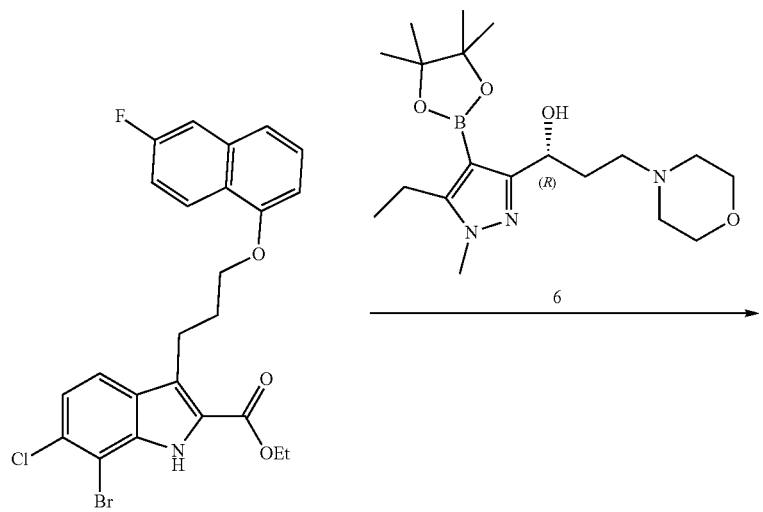

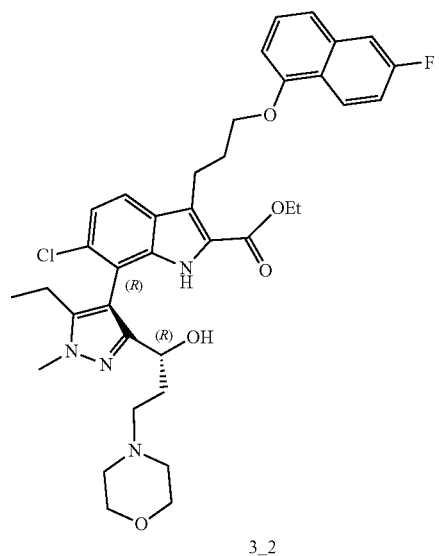

The mixture of Compound 2_8 (300 g, 594 mmol, 1.00 eq), Compound 6 (338 g, 891 mmol, 1.50 eq), RuPhos Pd G3 (49.7 g, 59.4 mmol, 0.10 eq), RuPhos (27.7 g, 59.4 mmol, 0.10 eq) and $K_3PO_4$ (252 g, 1.19 mol, 2.00 eq) in dioxane (2.10 L) and water (520 mL) was stirred at 140° C. for 14 hrs under $N_2$. TLC (EA: MeOH=10/1) indicated Compound 2_8 (Rf=0.9) was consumed and a new spot (Rf=0.3) was detected. The mixture was combined and diluted with EA (10 L), then the mixture was washed with brine (10 L) and concentrated to give a residue. The residue was purified by column chromatography ($SiO_2$, EA/MeOH=1/0 to 10/1) to give Compound3_2 (2.60 kg, 3.57 mol, 60.0% yield, 92.9% purity) as a brown gum.

$^1$HNMR: 400 MHZ,$CDCl_3$

δ=10.69 (s, 1H), 8.27 (dd, J=9.2, 5.6 Hz, 1H), 7.62-7.76 (m, 2H), 7.36-7.50 (m, 3H), 7.13-7.21 (m, 1H), 6.90 (dd, J=5.6, 3.2 Hz, 1H), 4.82-4.93 (m, 1H), 4.14-4.32 (m, 5H), 3.81-3.89 (m, 3H), 3.37-3.46 (m, 3H), 3.25-3.33 (m, 3H), 2.12-2.41 (m, 10H), 1.76 (s, 2H), 1.26 (t, J=7.2 Hz, 3H), 0.88 (t, J=7.2 Hz, 3H)

LC-MS: (method 2) product: RT=0.989 min, MS+1=677.3

HPLC: (method 7) product: RT=3.378 min

Example 12

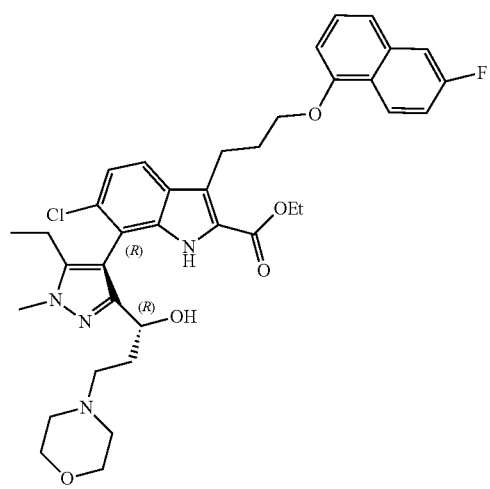

3_2

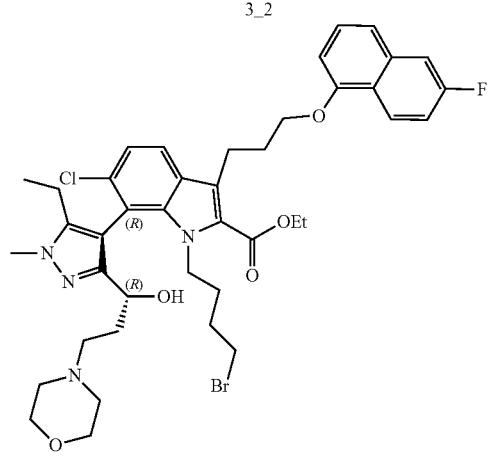

3_2a

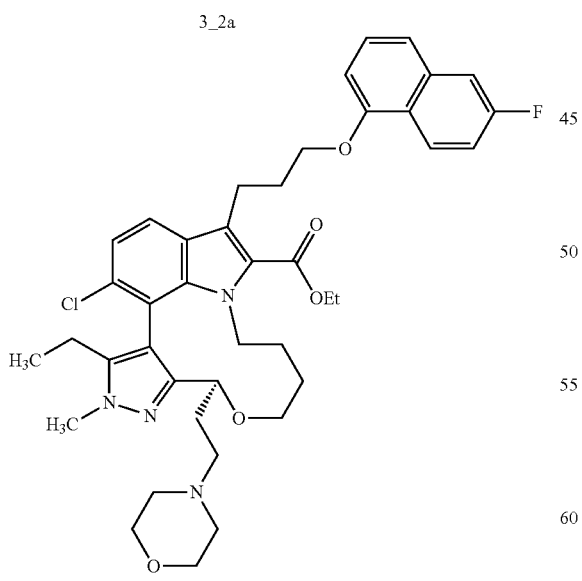

3_2b

To a mixture of Compound 3_2 (1.00 kg, 1.48 mol), 1,4-dibromobutane (957 g, 4.43 mol, 534 mL), 4A molecular sieves (500 g) and $Cs_2CO_3$ (1.92 kg, 5.90 mol) in MeCN (30.0 L) was stirred at 40° C. for 12 hrs. TLC (PE/EA=3/1) indicated Compound3_2 was consumed and Compound 3_2a formed. Then the mixture was stirred at 110° C. for another 15 hrs. LC-MS showed Compound 3_2 was consumed and ~58.3% of peak with desired MS (Rt=2.557 min) formed. HPLC showed Compound3_2 was consumed and ~44.0% of desired compound (Rt=3.602 min) formed. The combined reaction mixture (2 batches) was filtered and the filtrate was concentrated by evaporator under reduced pressure, the residue was combined with a second reaction batch (600 g) to give crude 3_2b (4.00 kg, crude) as a brown gum.

The crude 3_2b (3000 g) was purified by column chromatography ($SiO_2$, PE/EA=10/1 to EA/MeOH=4/1 (eluent containing 0.1% of $NH_3·H_2O$)) to give pure 3_2b (610 g) as a brown oil, which was combined with another batch of pure 3_2b to give total 3_2b (810 g, 1.11 mol) as a brown oil.

$^1$H NMR: 400 MHZ $CDCl_3$

δ 8.24-8.21 (dd, 1H), 7.78-7.68 (d, J=8.4 Hz, 1H), 7.67-7.64 (dd, 1H), 7.44-7.37 (m, 3H), 7.24-7.22 (d, J=8.4 Hz, 1H), 6.87-6.85 (dd, 1H), 4.45-4.41 (t, J=6.4 Hz, 1H), 4.33-4.18 (m, 5H), 3.98-3.91 (m, 1H), 3.86 (s, 1H), 3.31-3.36 (s, 1H), 3.08-3.03 (m, 1H), 2.33-2.16 (m, 10H), 2.09-1.99 (m, 1H), 1.76 (s, 1H), 1.28-1.25 (t, J=6.8 Hz, 4H), 1.12-1.02 (m, 3H), 0.82-0.79 (t, J=7.6 Hz, 3H).

LC-MS: (method 1), RT=0.981 min, MS+1=731.3, (method 8) product: RT=2.557 min, MS+1=731.4

HPLC: (method 4),RT=3.403 min, (method 7) product: RT=3.602 min

Intermediate 1

Ethyl 6-chloro-7-{5-ethyl-3-[(1R)-hydroxy-3-(morpholin-4-yl) propyl]-1-methyl-1H-pyrazol-4-yl}-3-{3-[(6-fluoronaphthalen-1-yl)oxy]propyl}-1H-indole-2-carboxylate

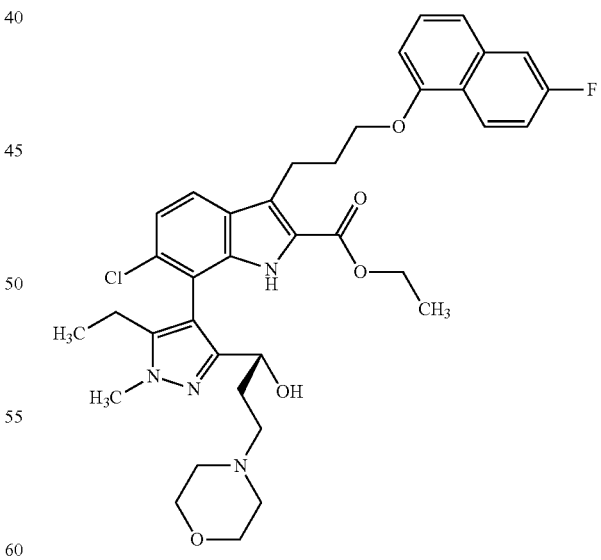

50.0 g (89.2 mmol) of ethyl 7-bromo-6-chloro-3-{3-[(6-fluoro-1-naphthyl)oxy]propyl}-1H-indole-2-carboxylate and 42.7 g (107 mmol) of (1R)-1-[5-ethyl-1-methyl-4-(4,4,5,5-tetramethyl-1,3,2-dioxaborolan-2-yl)-1H-pyrazol-3-yl]-3-(morpholin-4-yl)propan-1-ol were dissolved in 360 mL of 1,4-dioxane and 90 mL of water. 37.9 g (178 mmol) of potassium phosphate tribasic monohydrate were added. After three evacuate-refill cycles with argon 7.46 g (8.92 mmol) of methanesulfonato (2-dicyclohexyphosphino-2',6'-di-i-propoxy-1,1'-biphenyl) (2'-amino-1,1'-biphenyl-2-yl)palladium(II) (RuPhos Pd G3, Cas No: 1445085-77-7) were added and the flask was put into a preheated (150° C.) Radleys Heat-On aluminium block. Under argon the reaction mixture was stirred for 4 h at 100° C. The reaction mixture was filtered using a water resistant filter and the filter cake was washed with ethyl acetate. The filtrate was concentrated under vacuum and the remaining residue was triturated three times with each 200 mL of n-hexane and once with 200 mL of a mixture of n-hexane/cyclohexane (1:1) to obtain 78.0 g of an oily residue. In a second preparation 87.0 g (155 mmol) of ethyl 7-bromo-6-chloro-3-{3-[(6-fluoro-1-naphthyl)oxy]propyl}-1H-indole-2-carboxylate and 74.3 g (186 mmol) of (1R)-1-[5-ethyl-1-methyl-4-(4,4,5,5-tetramethyl-1,3,2-dioxaborolan-2-yl)-1H-pyrazol-3-yl]-3-(morpholin-4-yl)propan-1-ol were dissolved in 626 mL of 1,4-dioxane and 157 mL of water. 65.9 g (310 mmol) of potassium phosphate tribasic monohydrate were added. After three evacuate-refill cycles with argon 13.0 g (15.5 mmol) of methanesulfonato (2-dicyclohexyphosphino-2',6'-di-i-propoxy-1,1'-biphenyl) (2'-amino-1,1'-biphenyl-2-yl)palladium(II) (RuPhos Pd G3, Cas No: 1445085-77-7) were added and the flask was put into a preheated (150° C.) Radleys Heat-On aluminium block. Under argon the reaction mixture was stirred for 4 h at 100° C. The reaction mixture was filtered using a water resistant filter and the filter cake was washed with ethyl acetate. The filtrate was concentrated under vacuum and the remaining residue was triturated three times with each 500 mL of n-hexane and once with 200 mL of a mixture of n-hexane/cyclohexane (1:1) to obtain 190 g of an oily residue. The combined oily residues were purified via column chromatography (Biotage autopurifier system (Isolera LS®), 1500 g Biotage SNAP cartridge KP-Sil®, DCM/EtOH, 0-20% EtOH) to obtain 120 g of the title compound (73% theoretical yield, ratio of atropisomers approximately 4.5:1.0 determined by NMR).

Analytical HPLC Method:

Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

LC-MS: Rt=1.64 min; MS (ESIpos): m/z=677 [M+H]+

1H-NMR (400 MHZ, DMSO-d6) δ [ppm]: 0.831 (0.32), 0.851 (2.03), 0.870 (3.62), 0.889 (1.56), 1.036 (0.60), 1.054 (1.16), 1.068 (16.00), 1.154 (0.19), 1.188 (0.31), 1.206 (0.17), 1.229 (2.42), 1.246 (5.39), 1.264 (2.48), 1.483 (0.16), 1.762 (0.23), 1.781 (0.37), 1.797 (0.38), 1.801 (0.38), 1.807 (0.39), 1.821 (0.40), 1.839 (0.24), 1.989 (0.29), 2.145 (1.23), 2.157 (1.12), 2.176 (0.85), 2.194 (1.01), 2.211 (0.86), 2.232 (0.57), 2.254 (0.51), 2.266 (0.25), 2.272 (0.28), 2.284 (0.28), 2.323 (0.17), 2.328 (0.24), 2.347 (0.47), 2.355 (0.36), 2.365 (0.82), 2.374 (0.67), 2.384 (0.67), 2.393 (0.65), 2.403 (0.23), 2.411 (0.29), 2.518 (0.36), 2.523 (0.24), 3.294 (0.55), 3.313 (0.86), 3.382 (1.36), 3.393 (1.40), 3.404 (0.74), 3.419 (0.30), 3.424 (0.43), 3.436 (0.32), 3.442 (0.29), 3.454 (0.27), 3.564 (0.24), 3.813 (0.78), 3.817 (1.44), 3.839 (6.84), 3.939 (2.82), 4.200 (1.00), 4.214 (1.50), 4.222 (1.03), 4.229 (0.73), 4.240 (1.97), 4.258 (1.80), 4.275 (0.55), 4.346 (0.16), 4.358 (0.31), 4.869 (0.39), 4.880 (0.43), 5.758 (3.00), 6.879 (0.58), 6.886 (0.63), 6.893 (0.52), 6.901 (0.59), 7.155 (1.68), 7.167 (0.38), 7.176 (1.76), 7.189 (0.35), 7.376 (0.42), 7.382 (0.47), 7.397 (0.65), 7.404 (0.72), 7.412 (0.27), 7.420 (0.47), 7.427 (0.58), 7.433 (1.22), 7.440 (1.41), 7.447 (2.91), 7.461 (0.22), 7.645 (0.78), 7.652 (0.80), 7.671 (0.80), 7.678 (0.80), 7.691 (1.25), 7.713 (1.12), 8.247 (0.58), 8.261 (0.71), 8.270 (0.61), 8.284 (0.66), 10.715 (1.38).

Example 13

Ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10] [1,6]oxazacycloundecino[8,7,6-hi]indole-8-carboxylate

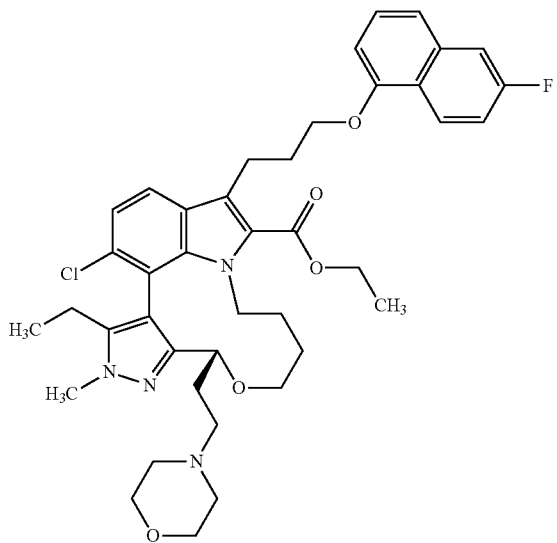 [SMILES: CCOC(=O)c1c(CCCOc2cccc3cc(F)ccc23)c2ccc(Cl)c3c2n1CCCCO[C@H](CCN1CCOCC1)c1nn(C)c(CC)c1-3]

10.0 g (13.3 mmol) of ethyl 6-chloro-7-{5-ethyl-3-[(1R)-hydroxy-3-(morpholin-4-yl) propyl]-1-methyl-1H-pyrazol-4-yl}-3-{3-[(6-fluoronaphthalen-1-yl)oxy]propyl}-1H-indole-2-carboxylate (ratio of atropisomers: 6.6:1) (Intermediate 1) were dissolved in 300 mL of acetonitrile and 17.3 g (53.2 mmol) of cesium carbonate and 3.44 g (16.0 mmol) of 1,4-dibromobutane were added at room temperature. The reaction mixture was stirred for 16 h at 100° C. (Radleys Heat-On aluminium block). After cooling to room temperature, 1000 mL of ethyl acetate were added and the organic phase was extracted twice with water. After drying over magnesium sulfate and evaporation of the organic phase the material was purified via column chromatography A followed by a second column chromatography B (A: Biotage autopurifier system (Isolera LS®), 340 g Biotage SNAP cartridge KP-Sil® ultra column, n-hexane/ethyl acetate: 10-100% ethyl acetate→ethyl acetate/MeOH 0-10%. B: Biotage autopurifier system (Isolera LS®), 110 g Biotage SNAP cartridge KP-NH®, n-hexane/ethyl acetate: 0-50% ethyl acetate) to obtain 5.50 g of the title compound (57% theoretical yield).

Analytical HPLC Method:

Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

LC-MS: Rt=1.75 min; MS (ESIpos): m/z=731 [M+H]+

1H-NMR (400 MHZ, DMSO-d6) δ[ppm]: 0.787 (3.17), 0.806 (7.48), 0.825 (3.35), 1.034 (0.91), 1.066 (2.21), 1.083 (0.52), 1.088 (0.48), 1.154 (1.28), 1.159 (0.18), 1.171 (2.78), 1.189 (1.50), 1.248 (5.33), 1.265 (11.23), 1.283 (5.17), 1.308 (0.17), 1.333 (0.20), 1.338 (0.25), 1.986 (4.92), 2.026 (0.44), 2.052 (1.06), 2.068 (1.25), 2.085 (0.65), 2.104 (0.18), 2.141 (0.25), 2.159 (0.72), 2.178 (1.72), 2.184 (1.81), 2.197 (2.07), 2.203 (2.31), 2.214 (1.46), 2.221 (1.40), 2.240 (0.68), 2.250 (0.78), 2.298 (3.21), 2.326 (1.74), 2.336 (0.81), 2.345 (0.73), 2.355 (0.51), 2.375 (0.21), 2.518 (1.49), 2.523 (1.03), 2.664 (0.31), 2.669 (0.43), 2.673 (0.31), 3.022 (0.41), 3.034 (0.49), 3.045 (0.54), 3.072 (0.30), 3.204 (0.20), 3.221 (0.37), 3.237 (0.60), 3.254 (0.87), 3.274 (1.09), 3.292 (1.29), 3.309 (1.09), 3.506 (3.51), 3.533 (0.39), 3.644 (0.21), 3.814 (0.18), 3.823 (0.23), 3.860 (16.00), 3.903 (0.27), 3.920 (0.51), 3.938 (0.85), 3.955 (0.60), 3.999 (0.37), 4.017 (1.09), 4.034 (1.13), 4.052 (0.37), 4.177 (0.64), 4.187 (0.81), 4.195 (1.95), 4.202 (1.75), 4.213 (2.29), 4.222 (2.47), 4.230 (1.23), 4.240 (2.16), 4.249 (0.68), 4.258 (0.84), 4.262 (0.94), 4.280 (1.95), 4.288 (0.42), 4.297 (1.65), 4.306 (0.98), 4.315 (0.48), 4.324 (1.01), 4.342 (0.31), 4.411 (0.89), 4.426 (1.47), 4.445 (0.84), 5.758 (1.49), 6.858 (1.26), 6.864 (1.33), 6.873 (1.14), 6.879 (1.36), 7.223 (4.25), 7.245 (4.36), 7.369 (0.89), 7.375 (1.01), 7.392 (1.26), 7.398 (1.42), 7.407 (0.57), 7.413 (0.94), 7.420 (1.11), 7.428 (2.28), 7.438 (2.57), 7.444 (5.72), 7.458 (0.47), 7.645 (1.53), 7.651 (1.58), 7.671 (1.53), 7.677 (1.54), 7.769 (3.64), 7.791 (3.20), 8.205 (1.30), 8.220 (1.37), 8.228 (1.35), 8.243 (1.28).

Example 14

Ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10] [1,6]oxazacycloundecino[8,7,6-hi]indole-8-carboxylate

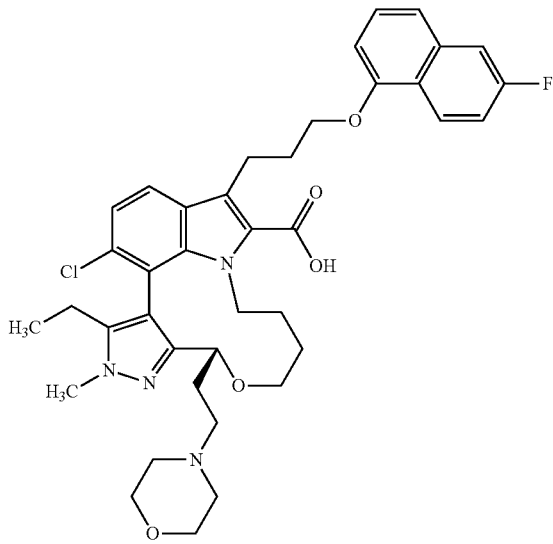 [SMILES: CCc1c2c(nn1C)[C@@H](CCN1CCOCC1)OCCCCn1c(C(=O)O)c(CCCOc3cccc4cc(F)ccc34)c3ccc(Cl)c-2c31]

5.50 g (7.52 mmol) of ethyl 4-chloro-3-ethyl-7-{3-[(6-fluoronaphthalen-1-yl)oxy]propyl}-2-methyl-(15R)-[2-(morpholin-4-yl)ethyl]-2,10,11,12,13,15-hexahydropyrazolo[4',3':9,10] [1,6]oxazacycloundecino[8,7,6-hi]indole-8-carboxylate (Example 1) were dissolved in 64 mL of tetrahydrofuran and 32 mL of ethanol, 900 mg (37.6 mmol) of lithium hydroxide dissolved in 18.8 mL of water were added and the reaction mixture was stirred for 16 h at 70° C. 2.69 g (12.8 mmol) of citric acid were added and the reaction mixture was stirred for 1 h at room temperature. 500 mL of water were added and the mixture was extracted twice with 300 mL of dichloromethane/methanol (10:1). After drying of the combined organic layers over magnesium sulfate and evaporation of the organic phase the material was purified via column chromatography (Biotage autopurifier system (Isolera LS®), 100 g Biotage SNAP cartridge KP-Sil®, DCM/MeOH, 0-30% MeOH or DCM/EtOH, 0-50% EtOH) to obtain 5.20 g of the title compound (98% theoretical yield).

If the product contained small amounts of solvents after chromatography, the residue was dissolved in warm methanol and the solution was poured in water at room temperature. The white precipitate was filtered and the filter cake was washed with water. The resulting material was dried at 50° C.

Analytical HPLC Method:
Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.;
DAD scan: 200-400 nm.
LC-MS: Rt=0.95 min; MS (ESIpos): m/z=703 [M+H]+
1H-NMR (400 MHZ, DMSO-d6) δ[ppm]: 0.790 (1.77), 0.809 (4.19), 0.828 (1.86), 1.026 (0.49), 1.148 (0.24), 1.257 (0.27), 2.042 (0.28), 2.060 (0.79), 2.077 (0.91), 2.095 (0.41), 2.139 (0.18), 2.157 (0.40), 2.175 (0.93), 2.187 (1.17), 2.194 (1.10), 2.206 (1.27), 2.224 (0.69), 2.243 (0.25), 2.327 (1.35), 2.332 (1.42), 2.343 (1.77), 2.518 (0.89), 2.522 (0.64), 2.664 (0.17), 2.668 (0.24), 2.673 (0.17), 3.007 (0.16), 3.032 (0.30), 3.049 (0.31), 3.071 (0.17), 3.240 (0.25), 3.256 (0.47), 3.273 (0.98), 3.288 (1.10), 3.321 (0.51), 3.859 (9.43), 3.882 (0.35), 3.898 (0.35), 3.916 (0.37), 3.933 (0.17), 4.169 (0.66), 4.185 (1.37), 4.200 (0.67), 4.316 (0.29), 4:332 (0.28), 4.351 (0.27), 4.402 (0.49), 4.418 (0.96), 4.436 (0.47), 5.758 (16.00), 6.838 (0.70), 6.845 (0.73), 6.854 (0.66), 6.860 (0.75), 7.193 (2.03), 7.214 (1.94), 7.348 (0.49), 7.355 (0.54), 7.371 (0.72), 7.378 (0.80), 7.393 (0.51), 7.400 (0.68), 7.419 (1.24), 7.429 (1.46), 7.434 (3.09), 7.449 (0.27), 7.637 (0.87), 7.643 (0.90), 7.663 (0.88), 7.669 (0.87), 7.732 (1.60), 7.754 (1.44), 8.219 (0.75), 8.233 (0.79), 8.241 (0.77), 8.257 (0.72).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below.

The full scope of the invention should be determined by reference to the claims, along with their full scope of equivalents, and the specification, along with such variations.

We claim:
1. A method for preparing a compound of Formula (I):

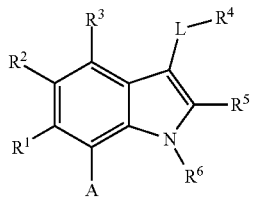

wherein
A is

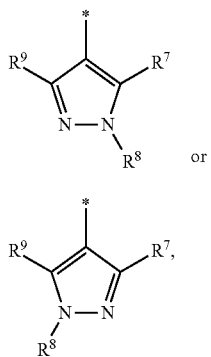

wherein $R^6$ and $R^7$, together with two carbon atoms of the pyrazole ring, two carbon atoms of the indole moiety and the nitrogen atom to which $R^6$ is attached, form a 9-membered to 16-membered ring, and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a $(C_1$-$C_3$-alkyl)-S(O)— group, a $(C_1$-$C_3$-alkyl)-S(O)$_2$— group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a $(C_1$-$C_3)$-haloalkyl-S— group and a $C_3$-$C_5$-cycloalkyl group;

L is a group —(CH$_2$)$_m$-E- wherein each CH$_2$ group is independently unsubstituted or substituted with one or two substituents and each substituent is independently selected from a halogen atom, a cyano group, a hydroxy group, a $C_1$-$C_3$-alkyl group and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$;

m is 2, 3, or 4;

$R^5$ is selected from a COOH group, a COO($C_1$-$C_6$-alkyl) group, a

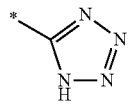

group, a —C(O)—NHS(O)$_2$($C_1$-$C_6$-alkyl) group, a —C(O)—NHS(O)$_2$($C_3$-$C_6$-cycloalkyl) group, and a —C(O)—NHS(O)$_2$(aryl) group;

—$R^6$-$R^7$— is $^\#$—(CH$_2$)$_n$—(B)$_t$—CR$^{22}$R$^{23}$—$^{\#\#}$,
wherein $^\#$ is the point of attachment with the indole nitrogen atom and $^{\#\#}$ is the point of attachment with the pyrazole carbon atom bearing the $R^7$ substituent; and wherein each —CH$_2$— group is independently unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group and a (heterocycloalkyl)-($C_1$-$C_3$-alkylene)- group;

n is 2, 3, 4, 5, or 6;
t is 1;
where the integers selected for variables n and t, together with the methylene group CR$^{22}$R$^{23}$ and the other non-variable atoms of the pyrazole and the indole moiety result in forming a 9-membered to 13-membered ring independently from the selection of variable A1 or A2;

B is —O—;
$R^8$ is selected from a hydrogen atom,
A $C_1$-$C_6$-alkyl group, which is unsubstituted or substituted with one or more substituents Independently selected from
a halogen atom, a hydroxy group, a $C_1$-$C_3$-alkoxy group, a $C_1$-$C_3$-haloalkoxy group,
a $C_3$-$C_6$-cycloalkyl group, a heterocycloalkyl group and a NR$^{20}$R$^{21}$ group
a $C_1$-$C_3$-haloalkyl group,
a $C_3$-$C_6$-cycloalkyl group and
a $C_1$-$C_6$-alkyl group in which one or two not directly adjacent carbon atoms are independently replaced by a heteroatom selected from —O— and —NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a $(C_3$-$C_7)$-cycloalkyl group,
a $(C_3$-$C_7)$-cycloalkyl-O—($C_1$-$C_3$-alkylene)- group, a phenyl-O—(C$_1$-C$_3$-alkylene)- group,
a phenyl-(C$_1$-C$_3$-alkylene)-O—(C$_1$-C$_3$-alkylene)- group,
a R$^{18}$-(phenylene)-(C$_1$-C$_3$-alkylene)-O—(C$_1$-C$_3$-alkylene)- group,
a R$^{18}$-(phenylene)-O—(C$_1$-C$_3$-alkylene)- group,
a R$^{18}$-(phenylene)-(heteroarylene)-O—(C$_1$-C$_3$-alkylene)- group,
a (R$^{18}$)-(heterocycloalkylene)-(C$_1$-C$_3$-alkylene)- group,
a (R$^{18}$)-(heterocycloalkylene)-(phenylene)-O—(C$_1$-C$_3$-alkylene)- group,
a (heterocycloalkenyl)-(phenylene)-O—(C$_1$-C$_3$-alkylene)- group,
a (R$^{18}$)-(heteroarylene)-(C$_1$-C$_3$-alkylene)-O—(C$_1$-C$_3$-alkylene)- group,
a (R$^{18}$)-(heteroarylene)-(phenylene)-O—(C$_1$-C$_3$-alkylene)- group,
a (R$^{19}$)—S(O)$_2$-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—NH-(phenylene)-O—(C$_1$-C$_3$-alkylene)- group,
a (R$^{19}$)—S(O)$_2$—N(C$_1$-C$_6$-alkyl)-(phenylene)-O—(C$_1$-C$_3$-alkylene)- group,
a (R$^{19}$)—S(O)$_2$-(heterocycloalkylene)-(phenylene)-O—(C$_1$-C$_3$-alkylene)- group,
a (R$^{18}$)-(heterocycloalkylene)-(heteroarylene)-O—(C$_1$-C$_3$-alkylene)- group,
a (R$^{19}$)-(heteroarylene)-O—(C$_1$-C$_3$-alkylene)- group,
a (R$^{18}$)-(heteroarylene)-O—(C$_1$-C$_3$-alkylene)- group,
a (R$^{19}$)—S(O)$_2$-(heteroarylene)-O—(C$_1$-C$_3$-alkylene)- group,
a (R$^{19}$)—S(O)$_2$-(heterocycloalkylene)-(heteroarylene)-O—(C$_1$-C$_3$-alkylene)- group,
a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkyl)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-C(O)—NH—(C$_1$-C$_3$-alkylene)- group,
a

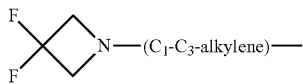

group and a

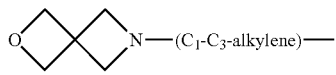

group,
where the phenyl ring is unsubstituted or substituted with a halogen atom, a hydroxy group or a C$_1$-C$_3$-alkoxy group and
the heterocycloalkyl group is unsubstituted or substituted with an oxo (=O) group or is unsubstituted or substituted with one or more substituents independently selected from a halogen atom, a hydroxy group, a C$_1$-C$_3$-alkyl group and a C$_1$-C$_3$-alkoxy group, or R$^8$ and R$^9$ together form a 5-membered or 6-membered ring optionally comprising one or two heteroatoms independently selected from —O— and —NR$^{14}$—;
R$^{14}$ is a hydrogen atom or a C$_1$-C$_3$-alkyl group;
R$^{16}$ and R$^{17}$ are each independently selected from a hydrogen atom, a C$_1$-C$_6$-alkyl group, a C$_1$-C$_6$-haloalkyl group, a C$_1$-C$_6$-alkoxy group, a C$_3$-C$_5$-cycloalkyl group, a C$_1$-C$_3$-alkyl-C(O)— group, a C$_1$-C$_3$-alkylS(O)$_2$— group and a C$_1$-C$_3$-alkyl-O—C(=O)— group;
R$^{18}$ is selected from a hydrogen atom, a hydroxy group, a cyano group, a C$_1$-C$_3$-alkyl group, a C$_1$-C$_6$-hydroxyalkyl group, a C$_1$-C$_3$-alkoxy group, a R$^{21}$OC(O)—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, a (C$_1$-C$_6$-alkyl)-C(O)— group and a C$_3$-C$_6$-cycloalkyl-C(O)— group;
R$^{19}$ is selected from a C$_1$-C$_3$-alkyl group, a C$_3$-C$_6$-cycloalkyl group and a NR$^{20}$R$^{21}$ group;
R$^{20}$ and R$^{21}$ are each independently selected from a hydrogen atom and a C$_1$-C$_6$-alkyl group;
R$^{22}$ is independently selected from,
a halogen atom selected from Cl, Br, and I,
a C$_2$-C$_6$-alkyl group
which is unsubstituted or substituted with one or more substituents selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a C$_3$-C$_6$-cycloalkyl group, a heterocycloalkyl group, an aryl group, a (R$^{18}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{19}$)S(O)$_2$-arylene-O— group, a (R$^{19}$)S(O)$_2$-heterocycloalkylene-arylene-O— group, an aryl-heteroarylene-O— group, an aryl-heteroarylene-O—(C$_1$-C$_3$-alkylene)- group, a heterocycloalkyl-(C$_1$-C$_3$-alkylene)-C(O)— group, a heterocycloalkyl-NH—C(O) group, an aryl-(C$_1$-C$_3$-alkylene)-NH—C(O)— group, a heterocycloalkylene-(C$_1$-C$_3$-alkylene)-S(O)$_2$— group and a heterocycloalkylene-heteroarylene-S(O)$_2$— group;
a C$_1$-C$_3$-alkyl-C(O)— group,
a C$_3$-C$_6$-cycloalkyl group,
an aryl group,
a heterocycloalkyl group and
a heteroaryl group;
whereby any heterocycloalkyl group of R$^{22}$ may optionally be itself further substituted with a C$_1$-C$_3$-alkyl group or one or two halogen atoms;
R$^{23}$ is a hydrogen atom;
comprising contacting a compound of formula (IIA) when A is A1, or formula (IIB) when A is A2:

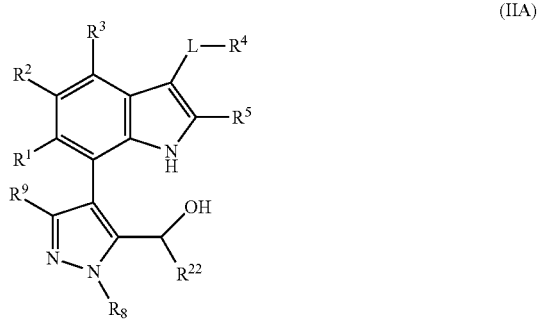

(IIA)

-continued (IIB)

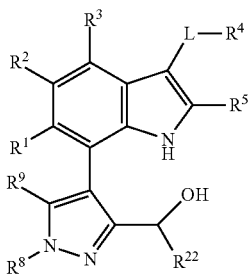

with a di-functionalized alkane

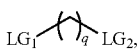

wherein
variables $R^1$, $R^2$, $R^3$, $R^4$, $R^8$, $R^9$, and $R^{22}$ are as defined above,
$R^5$ is selected from a COO($C_1$-$C_6$-alkyl) group, a

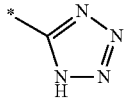

group, a —C(O)—NHS(O)$_2$($C_1$-$C_6$-alkyl) group, a —C(O)—NHS(O)$_2$($C_3$-$C_6$-cycloalkyl) group, and a —C(O)—NHS(O)$_2$(aryl) group;
q is 2, 3, 4, 5, or 6, and
$LG^1$ and $LG^2$ are each independently halo or sulfonate.

2. A method for preparing a compound of Formula (I):

(I)

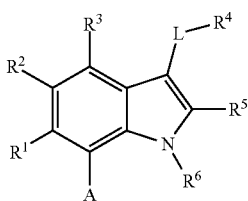

wherein
A is (A1)

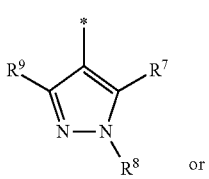

or (A2)

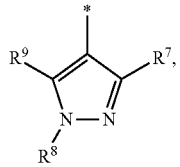

wherein $R^6$ and $R^7$, together with two carbon atoms of the pyrazole ring, two carbon atoms of the indole moiety and the nitrogen atom to which $R^6$ is attached, form a 9-membered to 13-membered ring, and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —(CH$_2$)$_m$-E- wherein each CH$_2$ group is independently unsubstituted or substituted with one or two substituents and each substituent is independently selected from a halogen atom, a cyano group, a hydroxy group, a $C_1$-$C_3$-alkyl group and a $C_1$-$C_3$-alkoxy group;

E is a bond, an oxygen atom, a sulfur atom, or a —NR$^{14}$— group and constitutes the connecting element to $R^4$;

m is 2, 3, or 4;

$R^5$ is selected from a —COOH group, a COO($C_1$-$C_6$-alkyl) group, and a

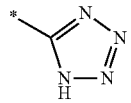

group;

—$R^6$-$R^7$— is $^{\#}$—(CH$_2$)$_n$—(B)$_t$—CR$^{22}$R$^{23}$—$^{\#\#\#}$,
wherein $^{\#}$ is the point of attachment with the indole nitrogen atom and $^{\#\#\#}$ is the point of attachment with the pyrazole carbon atom bearing the $R^7$ substituent; and wherein each —CH$_2$— group is independently unsubstituted or substituted with one or more substituents independently selected from a halogen atom, a hydroxy group, a NR$^{16}$R$^{17}$ group, a $C_1$-$C_3$-alkyl group, a $C_1$-$C_3$-haloalkyl group, a $C_1$-$C_3$-alkoxy group and a $C_1$-$C_3$-haloalkoxy group;

n is 2, 3, 4, 5 or 6;

t is 1;

where the integers selected for variables n and t, together with the methylene group CR$^{22}$R$^{23}$ and the other non-variable atoms of the pyrazole and the indole moiety result in forming a 9-membered to 13-membered ring independently from the selection of variable A1 or A2;

B is —O—;
R⁸ is selected from a hydrogen atom,
  a $C_1$-$C_6$-alkyl group, which is unsubstituted or substituted with one or more substituents independently selected from
    a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group and a $NR^{20}R^{21}$ group;
R⁹ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O— group,
  a $C_1$-$C_4$-haloalkoxy group,
  a $C_1$-$C_6$-alkyl-O—($C_1$-$C_3$-alkylene)- group,
  a ($C_1$-$C_3$-alkyl)-NH—($C_1$-$C_3$-alkylene)- group,
  a ($C_3$-$C_7$)-cycloalkyl group and
  a ($C_3$-$C_7$)-cycloalkyl-O—($C_1$-$C_3$-alkylene)- group;
$R^{14}$ is a hydrogen atom or a $C_1$-$C_3$-alkyl group;
$R^{16}$ and $R^{17}$ are each independently selected from a hydrogen atom, a $C_1$-$C_6$-alkyl group, a $C_1$-$C_6$-haloalkyl group, a $C_1$-$C_6$-alkoxy group, a $C_3$-$C_5$-cycloalkyl group, a $C_1$-$C_3$-alkyl-C(O)— group, a $C_1$-$C_3$-alkylS(O)_2$— group and a $C_1$-$C_3$-alkyl-O—C(=O)— group;
$R^{20}$ and $R^{21}$ are each independently selected from a hydrogen atom and a $C_1$-$C_6$-alkyl group;
$R^{22}$ is independently selected from
  a halogen atom selected from Cl, Br, and I,
  a $C_2$-$C_6$-alkyl group
    which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group;
  a $C_3$-$C_6$-cycloalkyl group,
  a phenyl group,
  whereby any heterocycloalkyl group of $R^{22}$ may optionally be itself further substituted with a $C_1$-$C_3$-alkyl group or one or two halogen atoms;
$R^{23}$ is a hydrogen atom;
comprising contacting a compound of formula (IIA) when A is A1, or formula (IIB) when A is A2:

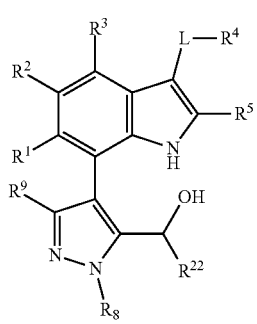
(IIA)

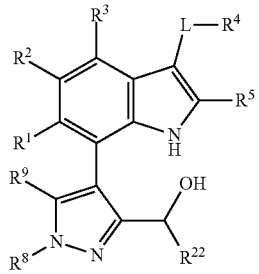
(IIB)

with a di-functionalized alkane

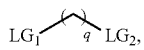

wherein
variables $R^1$, $R^2$, $R^3$, $R^4$, $R^8$, $R^9$, and $R^{22}$ are as defined above,
$R^5$ is a —COO($C_1$-$C_6$-alkyl) group or a

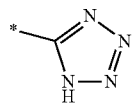

group,
q is 2, 3, 4, 5, and 6, and
$LG^1$ and $LG^2$ are each independently halo or sulfonate.

3. A method for preparing a compound of Formula (I):

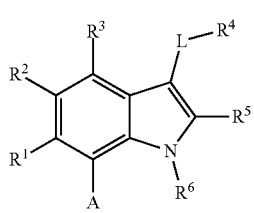
(I)

wherein
A is

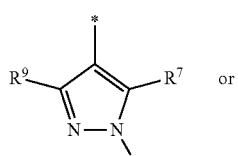
(A1)

or

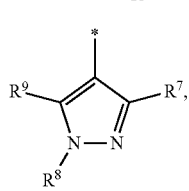
(A2)

wherein R⁶ and R⁷, together with two carbon atoms of the pyrazole ring, two carbon atoms of the indole moiety and the nitrogen atom to which R⁶ is attached, form a 10-membered to 12-membered ring, and * is the point of attachment of these moieties to the indole carbon atom bearing the A substituent;

R¹ and R² are each independently selected from a hydrogen atom and a halogen atom;

R³ is a hydrogen atom;

R⁴ is selected from an aryl group and a heteroaryl group, each of which is unsubstituted or substituted with one, two or three substituents and each substituent is independently selected from a halogen atom and a C₁-C₃-alkyl group;

L is a group —(CH₂)ₘ-E-;

E is a bond or an oxygen atom and constitutes the connecting element to R⁴;

m is 2, 3, or 4;

R⁵ is a —COOH group or a —COO(C₁-C₆-alkyl) group;

—R⁶-R⁷— is #—(CH₂)ₙ—(B)ₜ—CR²²R²³—##, wherein # is the point of attachment with the indole nitrogen atom and ## is the point of attachment with the pyrazole carbon atom bearing the R⁷ substituent; and wherein each —CH₂— group is independently unsubstituted or substituted with one or more substituents independently selected from a halogen atom, a hydroxy group, a NR¹⁶R¹⁷ group, a C₁-C₃-alkyl group, a C₁-C₃-haloalkyl group, a C₁-C₃-alkoxy group, a C₁-C₃-haloalkoxy group;

n is 3, 4 or 5;

t is 1;

where the integers selected for variables n and t together with the methylene group CR²²R²³ and the other non-variable atoms of the pyrazole and the indole moiety result in forming a 10-membered to 12-membered ring independently from the selection of variable A1 or A2;

B is —O—;

R⁸ is selected from a hydrogen atom and a C₁-C₄-alkyl group, which is unsubstituted or substituted with one or more substituents independently selected from a halogen atom, a hydroxy group, a C₃-C₆-cycloalkyl group and a heterocycloalkyl group;

R⁹ is selected from a C₁-C₄-alkyl group, a C₁-C₃-hydroxyalkyl group, a C₁-C₃-haloalkyl group, a C₁-C₃-alkyl-O— group, a C₁-C₃-haloalkoxy group, a C₁-C₃-alkyl-O—(C₁-C₃-alkylene)- group, a (C₃-C₆)-cycloalkyl group, a R¹⁹-(phenylene)-O—(C₁-C₃-alkylene)- group, a NR²⁰R²¹—(C₁-C₃-alkylene)- group and a (C₁-C₃-alkyl)-NH—(C₁-C₃-alkylene)- group;

R¹⁶ and R¹⁷ are each independently selected from a hydrogen atom, a C₁-C₆-alkyl group, a C₁-C₆-haloalkyl group and a C₁-C₆-alkoxy group;

R¹⁹ is selected from a C₁-C₃-alkyl group, a C₃-C₆-cycloalkyl group and a NR²⁰R²¹ group;

R²⁰ and R²¹ are each independently selected from a hydrogen atom and a C₁-C₃-alkyl group;

R²² is independently selected from a halogen atom selected from Cl, Br, and I, a C₂-C₅-alkyl group which is unsubstituted or substituted with a group selected from a hydroxy group, a NR¹⁶R¹⁷ group, a C₁-C₃-haloalkyl group, a C₁-C₃-hydroxyalkyl group, a C₁-C₃-alkoxy group, a C₃-C₆-cycloalkyl group, a heterocycloalkyl group, and a phenyl group;

a C₃-C₆-cycloalkyl group, and a phenyl group, whereby any heterocycloalkyl group of R²² may optionally be itself further substituted with a C₁-C₃-alkyl group or one or two halogen atoms;

R²³ is a hydrogen atom;

comprising contacting a compound of formula (IIA) when A is A1, or formula (IIB) when A is A2:

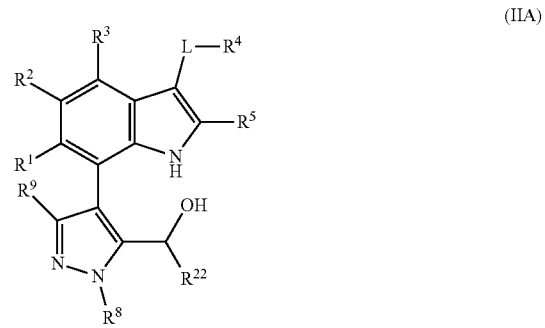

(IIA)

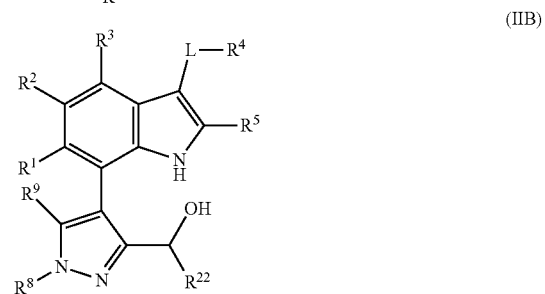

(IIB)

with a di-functionalized alkane

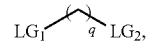

wherein variables R¹, R², R³, R⁴, R⁸, R⁹, and R²² are as defined above,

R⁵ is —CO₂(C₁₋₆alkyl), q is 3, 4, or 5, and

LG¹ and LG² are each independently halo or sulfonate.

4. The method of claim 1, wherein the method comprises preparing a compound of Formula (I):

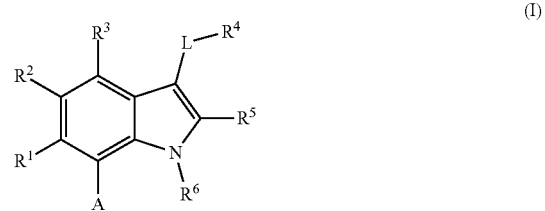

(I)

wherein
A is

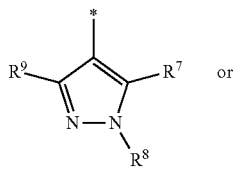 (A1)

or

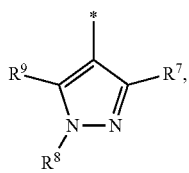 (A2)

wherein $R^6$ and $R^7$, together with two carbon atoms of the pyrazole ring, two carbon atoms of the indole moiety and the nitrogen atom to which $R^6$ is attached, form a 11-membered ring, and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one or two substituents and each substituent is independently selected from a halogen atom and a $C_1$-$C_3$-alkyl group;

L is a group —$(CH_2)_m$-E-;

E is an oxygen atom and constitutes the connecting element to $R^4$;

m is 3;

$R^5$ is a —COOH group or a —COO($C_1$-$C_6$-alkyl) group;

—$R^6$-$R^7$— is $^\#$—$(CH_2)_n$—(B)$_t$—$CR^{22}R^{23}$—$^{\#\#}$, wherein $^\#$ is the point of attachment with the indole nitrogen atom and $^{\#\#}$ is the point of attachment with the pyrazole carbon atom bearing the $R^7$ substituent;

n is 4;

t is 1;

where the integers selected for variables n and t together with the methylene group $CR^{22}R^{23}$ and the other non-variable atoms of the pyrazole and the indole moiety result in forming a 11-membered ring independently from the selection of variable A1 or A2;

B is —O—;

$R^8$ is selected from a hydrogen atom and
a $C_1$-$C_4$-alkyl group, which is unsubstituted or substituted with one or more substituents independently selected from a halogen atom, a hydroxy group, a $C_3$-$C_6$-cycloalkyl group and a heterocycloalkyl group;

$R^9$ is a $C_1$-$C_4$-alkyl group;

$R^{22}$ is independently selected from
a halogen atom selected from Cl, Br, and I,
a $C_3$-$C_6$-cycloalkyl group,
a phenyl group and
a $C_2$-$C_5$-alkyl group which is unsubstituted or substituted with a group selected from a hydroxy group, a $NR^{16}R^{17}$ group, a $C_1$-$C_3$-haloalkyl group, a $C_1$-$C_3$-alkoxy group, a $C_3$-$C_6$-cycloalkyl group, a heterocycloalkyl group, and a phenyl group;

whereby any heterocycloalkyl group of $R^{22}$ may optionally be itself further substituted with a $C_1$-$C_3$-alkyl group or one or two halogen atoms;

$R^{23}$ is a hydrogen atom;

comprising contacting a compound of formula (IIA) when A is A1, or formula (IIB) when A is A2:

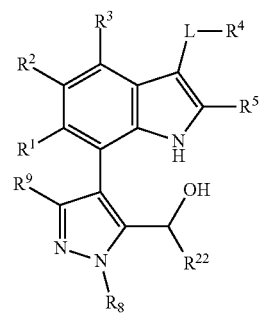 (IIA)

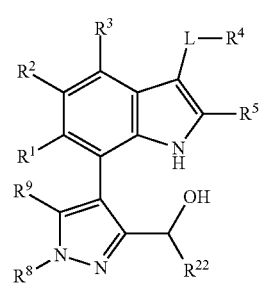 (IIB)

with a di-functionalized alkane

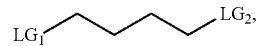

wherein
variables $R^1$, $R^2$, $R^3$, $R^4$, $R^8$, $R^9$, and $R^{22}$ are as defined above, $R^5$ is —$CO_2(C_{1-6}alkyl)$ and $LG^1$ and $LG^2$ are each independently halo or sulfonate.

5. The method of claim 1, wherein the method comprises a compound of Formula (I):

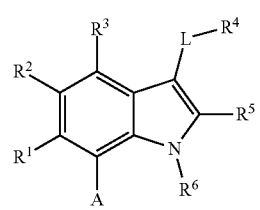 (I)

wherein
A is

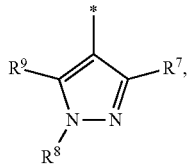

(A2)

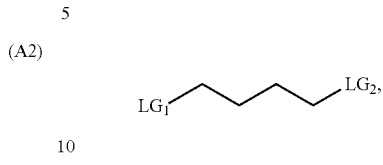

wherein R⁶ and R⁷, together with two carbon atoms of the pyrazole ring, two carbon atoms of the indole moiety and the nitrogen atom to which R⁶ is attached, form a 11-membered ring, and * is the point of attachment of these moieties to the indole carbon atom bearing the A substituent;

R¹ is selected from a hydrogen atom, a fluorine atom and a chlorine atom;

R² and R³ are each a hydrogen atom;

R⁴ is a naphthyl group which is unsubstituted or substituted with a fluorine atom;

L is —(CH₂)₃—O—;

R⁵ is a COOH group or a COO(C₁-C₆-alkyl) group;

—R⁶-R⁷— is #—(CH₂)₄—O—CR²²R²³—##, wherein # is the point of attachment with the indole nitrogen atom and ## is the point of attachment with the pyrazole carbon atom bearing the R⁷ substituent;

R⁸ is a C₁-C₃-alkyl group;

R⁹ is a C₁-C₃-alkyl group;

R²² is independently selected from
 a C₃-C₆-cycloalkyl group,
 a phenyl group and
 a C₂-C₅-alkyl group which is unsubstituted or substituted with a substituent selected from a hydroxy group, a NR¹⁶R¹⁷ group, a C₁-C₃-haloalkyl group, a C₁-C₃-alkoxy group, a C₃-C₆-cycloalkyl group, a heterocycloalkyl group, and a phenyl group;
 whereby any heterocycloalkyl group of R²² may optionally be itself further substituted with a C₁-C₃-alkyl group or one or two halogen atoms;

R²³ is a hydrogen atom;

comprising contacting a compound of formula (IIB):

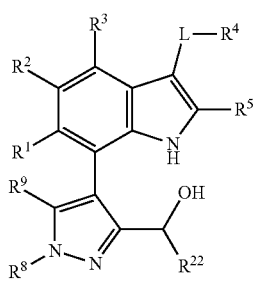

(IIB)

with a di-functionalized alkane wherein variables R¹, R², R³, R⁴, R⁸, R⁹, and R²² are as defined above, R⁵ is —CO₂(C₁₋₆alkyl) and LG¹ and LG² are each independently halo or sulfonate.

6. The method of claim 1, wherein R⁵ is —CO₂ (C₁₋₆alkyl).

7. The method of claim 1, wherein LG¹ and LG² are each halo.

8. The method of claim 1, wherein LG¹ and LG² are each sulfonate.

9. The method of claim 1, wherein the contacting occurs in a solvent selected from halogenated solvents, aliphatic and aromatic solvents, ethers, nitriles, amides, alcohols, ketones, water and any combination thereof.

10. The method of claim 1, wherein the contacting occurs in the presence of a base selected from alkali metal or alkaline earth metal acetates, phosphates, amides, carbonates, hydrogen carbonates, hydrides, hydroxides and alkoxides.

11. The method of claim 1, wherein the contacting occurs in the presence of a phase transfer catalyst selected from tetrabutylammonium bromide, tetraoctylammoniumbromide, or triethylbenzylammonium chloride.

12. The method of claim 1, wherein the contacting occurs in the presence of an additive selected from sodium iodide, potassium iodide, and tetrabutylammonium iodide (TBAI).

13. The method of claim 1, wherein the contacting occurs in the absence of iodide, e.g., in the absence of an additive selected from sodium iodide, potassium iodide, and tetrabutylammonium iodide (TBAI).

14. The method of claim 1, wherein the contacting comprises first alkylating the indole nitrogen of the compound of formula (II) and isolating the product, and second alkylating the hydroxyl group of the compound of formula (II) and isolating the compound of formula (I).

15. The method of claim 5, further comprising contacting the compound of formula (I) with a base to form a compound of formula (I) where R⁵ is COOH, and wherein the base is selected from LiOH, NaOH, KOH, Mg(OH)₂, Li₂CO₃, Na₂CO₃, K₂CO₃, and MgCO₃.

16. The method of claim 15, wherein the contacting occurs in a solvent selected from THF, EtOH and water, or any combinations thereof.

17. The method of claim 1, wherein A is A1.

18. The method of claim 1, wherein A is A2.

19. The method of claim 1, wherein the compound of formula (I) is
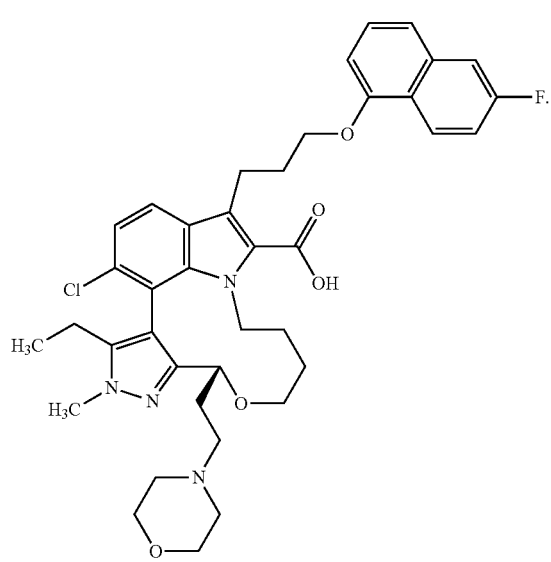 [SMILES: CCc1c2c(nn1C)[C@@H](CCN1CCOCC1)OCCCCn1c(C(=O)O)c(CCCOc3cccc4cc(F)ccc34)c3ccc(Cl)c-2c31]
20. The method of claim 1, wherein the compound of formula (II) is
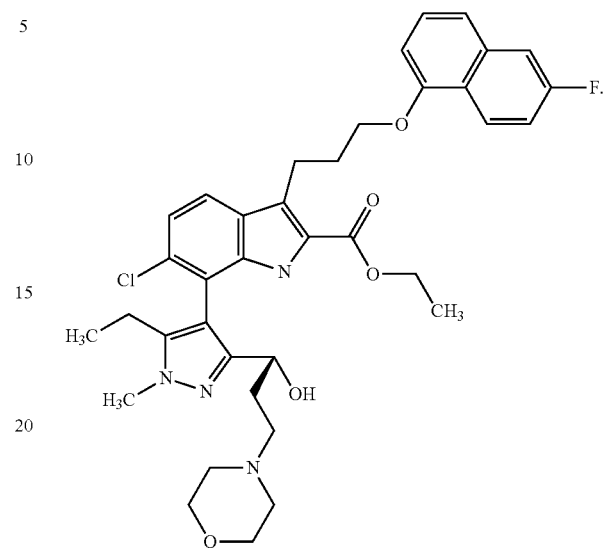
* * * * *